United States Patent
Pohl et al.

(10) Patent No.: US 11,059,865 B2
(45) Date of Patent: Jul. 13, 2021

(54) CATALYTICALLY ACTIVE PROTEIN AGGREGATES AND METHODS FOR PRODUCING THE SAME

(71) Applicants: evoxx technologies GmbH, Monheim am Rhein (DE); Forschungszentrum Jülich GmbH, Jülich (DE)

(72) Inventors: Martina Pohl, Aachen (DE); Karl-Erich Jaeger, Mülheim an der Ruhr (DE); Martin Diener, Aulendorf (DE); Ulrich Krauss, Aachen (DE)

(73) Assignee: evoxx technologies GmbH, Monheim am Rhein (DE)

( * ) Notice: Subject to any disclaimer, the term of this patent is extended or adjusted under 35 U.S.C. 154(b) by 387 days.

(21) Appl. No.: 15/746,315

(22) PCT Filed: Jul. 22, 2016

(86) PCT No.: PCT/EP2016/067571
§ 371 (c)(1),
(2) Date: Jan. 19, 2018

(87) PCT Pub. No.: WO2017/017028
PCT Pub. Date: Feb. 2, 2017

(65) Prior Publication Data
US 2020/0087355 A1    Mar. 19, 2020

(30) Foreign Application Priority Data

Jul. 24, 2015 (GB) .................................. 1513098

(51) Int. Cl.
*C12N 15/62* (2006.01)
*C07K 19/00* (2006.01)
*C07K 14/21* (2006.01)
*C07K 14/195* (2006.01)
*C07K 14/395* (2006.01)
*C12N 9/04* (2006.01)
*C12N 9/10* (2006.01)
*C12N 9/20* (2006.01)
*C12N 9/88* (2006.01)
*A61K 38/00* (2006.01)

(52) U.S. Cl.
CPC ............ *C07K 14/21* (2013.01); *C07K 14/195* (2013.01); *C07K 14/395* (2013.01); *C12N 9/0006* (2013.01); *C12N 9/1022* (2013.01); *C12N 9/20* (2013.01); *C12N 9/88* (2013.01); *C12N 15/62* (2013.01); *C12Y 101/01001* (2013.01); *C12Y 202/01009* (2013.01); *C12Y 301/01001* (2013.01); *C12Y 301/01074* (2013.01); *C12Y 401/0201* (2013.01); *C12Y 401/02038* (2013.01); *C07K 2319/73* (2013.01)

(58) Field of Classification Search
CPC .......................... C07K 2319/73; C12N 15/62
See application file for complete search history.

(56) References Cited

U.S. PATENT DOCUMENTS

| | | | | | |
|---|---|---|---|---|---|
| 2010/0267584 | A1* | 10/2010 | Bolotine | ............ | C12Q 1/6809 506/16 |
| 2014/0315765 | A1* | 10/2014 | McDaniel | ............ | C09K 8/582 507/201 |
| 2016/0346297 | A1* | 12/2016 | Sheehan | ............ | A61K 31/519 |

FOREIGN PATENT DOCUMENTS

| | | | |
|---|---|---|---|
| KR | 20130055480 A | 5/2013 | |
| WO | 9902707 A1 | 1/1999 | |
| WO | WO 99/02707 | 1/1999 | |
| WO | WO-2006112777 A2 * | 10/2006 | ............ A61K 47/62 |
| WO | 2008011204 A2 | 1/2008 | |
| WO | WO 2008/011204 | 1/2008 | |
| WO | 2008067591 A1 | 6/2008 | |
| WO | 2009015165 A1 | 1/2009 | |
| WO | 2010131117 A1 | 11/2010 | |

OTHER PUBLICATIONS

Wu et al. (2011) Active protein aggregates induced by terminally attached self-assembling peptide ELK16 in *Escherichia coli* Microb.; Cell Facteorie, vol. 10, No. 9, pp. 1-8.*
Diener M. (Sep. 2014) Dissertation "Von gezielter Oligomerisierung zu katalytisch aktiven inclusion bodies—Eine alternative Strategic zur Stabilisierung und Immobilisierung von Biokatalysatoren", pp. 1-153.*
Scholz et al. (2013) "Fusion of a Flavin-Based Fluorescent Protein to Hydroxynitrile Lyase from *Arabidopsis thaliana* Improves Enzyme Stability", Appl. Environ. Microbiol., vol. 79, pp. 4727-4733.*
Hernamdz et al. (2008) A new expression system for protein crystallization using trimeric coiled-coil adaptorsProtein Eng. Design Select, vol. 21, pp. 11-18.*
Ha et al. (J. Mol. Biol. (2006) Modular Enzyme Design: Regulation by Mutually Exclusive Protein Folding vol. 357, No. 4, pp. 1058-1062.*
Nahalka and Nidetsky: "Fusion to a Pull-Down Domain: A Novel Approach of Producing Trigonopsis variabilis D-Amino Acid Oxidase as Insoluble Enzyme Aggregates", Biotechnology & Bioengineering 97(3), (2007), pp. 454-461.

(Continued)

*Primary Examiner* — Scarlett Y Goon
*Assistant Examiner* — Samuel W Liu
(74) *Attorney, Agent, or Firm* — Norton Rose Fulbright US LLP; James R. Crawford

(57) ABSTRACT

Disclosed are catalytically active water-insoluble protein aggregates comprising fusion proteins which comprise a coiled-coil domain and a catalytic domain, methods of manufacturing such protein aggregates, and their use.

11 Claims, 6 Drawing Sheets
Specification includes a Sequence Listing.

(56) References Cited

OTHER PUBLICATIONS

Schmidt, et al.: "A Generic System for the Expression and Purificaiton of Soluble and Stable Influenza Neuraminidase", PLos One 6(2), (2011), pp. 1-13.

Wu, et al.: "Active protein aggregates induced by terminally attached self-assembling peptide ELK16 in *Escherichia coli*", Microbial Cell Factories 10:9 (2011), pp. 1-8.

Office Action issued in Corresponding Chinese Application No. 201680043588.6, dated Mar. 23, 2021 (No English Translation provided).

* cited by examiner

CATALYTICALLY ACTIVE PROTEIN AGGREGATES AND METHODS FOR PRODUCING THE SAME

This application is a § 371 of PCT/EP2016/067571 filed Jul. 22, 2016 and claims priority under § 119 from GB 1513098.2 filed Jul. 24, 2015, each of which is incorporated herein by reference in its entirety.

FIELD OF THE INVENTION

The invention relates in general to the field of industrial biotechnology, and more particularly to catalytically active protein aggregates, methods for producing catalytically active protein aggregates, and the use of catalytically active protein aggregates in biocatalytic processes.

BACKGROUND OF THE INVENTION

In industrial biotechnology, also known as white biotechnology, biotechnology is applied to industrial processes. For example, enzymes are used as catalysts either to produce valuable chemicals or to degrade hazardous or polluting chemicals. For use in industrial processes high performance enzymes are desired which are simple and cost efficient to produce, yet highly stable and active under the particular reaction conditions of the specific industrial process wherein performing their catalytic activity.

Usually an enzyme is optimized for the purpose of its specific use by protein engineering. Substituting, deleting or inserting one or more amino acids of an enzyme can render it performing its tasks better and/or can increase the enzymes stability in the reaction environment. Another approach of utilizing enzymes in industrial processes comprises the immobilization of the enzymes on solid surfaces such as beads. Such an immobilization not only improves utility of the enzymes, but can also improve their stability— and hence their performance.

Enzymes to be used in industrial processes are often purified from recombinant bacterial cells heterologously expressing said enzyme. However, expression of non-native proteins in bacteria leads to the formation of so-called inclusion bodies. Inclusion bodies almost exclusively contain the heterologous expressed protein, but contain very little host protein, ribosomal components or DNA/RNA fragments. It appears that formation of inclusion bodies occurs as a result of intracellular accumulation of only partially folded expressed proteins which aggregate through non-covalent hydrophobic or ionic interactions or a combination of both. Due to the inappropriate folding and aggregation of the heterologous proteins in the inclusion body, these proteins usually do not possess their native activity. The aggregation of proteins in inclusion bodies has been reported to be reversible, and it is necessary to re-solubilize enzymes from the inclusion bodies for obtaining catalytically active proteins which may then be employed in industrial processes. However, re-solubilization of proteins from inclusion bodies is not always possible, and any re-solubilization of enzymes from inclusion bodies is a tedious process.

Therefore, there is a need in industrial biotechnology for providing means which avoid the disadvantages that are associated with aggregation of heterologously expressed proteins and making them suitable for industrial processes.

Korean patent application KR 20130055480 A discloses active inclusion bodies including a fusion protein comprising a target polypeptide and the pyruvate dehydrogenase of Paenibacillus polymyxa. Said target polypeptide is either the green fluorescent protein (GFP) or amylase. Expression of a fusion gene containing the Paenibacillus polymyxa PoxB gene and either the gene encoding GFP or amylase lead to inclusion bodies which possess green fluorescence or amylase activity respectively.

The formation of active protein aggregates in cytoplasmic inclusion bodies of E. coli by attaching an ionic self-assembling peptide $(LELELKLK)_2$ to the carboxyl termini of amadorinase II, β-xylosidase or GFP has been reported by Wu et al. (Microbial Cell Factories 2011, 10:9).

However, no generally applicable tool for generating enzymatically active inclusion bodies have been disclosed, which is easy to be used and may be applied to a broad variety of enzymes being relevant in industrial biotechnology.

It has surprisingly been found by the inventors of the invention disclosed herein that fusion proteins comprising a coiled-coil domain and a catalytic domain not only retain the catalytic activity of their catalytic domain when aggregated in inclusion bodies, but that the catalytic activity is more resilient and sturdy compared to the catalytic activity of the corresponding enzyme lacking a coiled-coil domain.

SUMMARY OF INVENTION

In a first aspect, the invention provides protein aggregates, wherein said protein aggregates comprise a fusion protein, said fusion protein comprising a coiled-coil domain and a catalytic domain.

In a second aspect, the invention provides methods for producing protein aggregates comprising a fusion protein, said fusion protein comprising a coiled-coil domain and a catalytic domain.

In a third aspect, the invention provides the use of protein aggregates, wherein said protein aggregates comprise a fusion protein, said fusion protein comprising a coiled-coil domain and a catalytic domain, in a catalytic reaction.

In a further aspect, the invention provides the use of a protein aggregate comprising a fusion protein, wherein said fusion protein comprises a coiled-coil domain and a catalytic domain, for stabilizing a catalytic activity of said catalytic domain.

In a further aspect, the invention provides nucleic acid molecules encoding a fusion protein comprising a coiled-coil domain and a catalytic domain.

In yet another aspect, the invention provides a host cell comprising a nucleic acid molecule encoding a fusion protein comprising a coiled-coil domain and a catalytic domain.

In yet another aspect, the invention provides a host cell comprising a protein aggregate comprising a fusion protein, wherein said fusion protein comprises a coiled-coil domain and a catalytic domain.

DETAILED DESCRIPTION OF EMBODIMENTS

Figure 1:
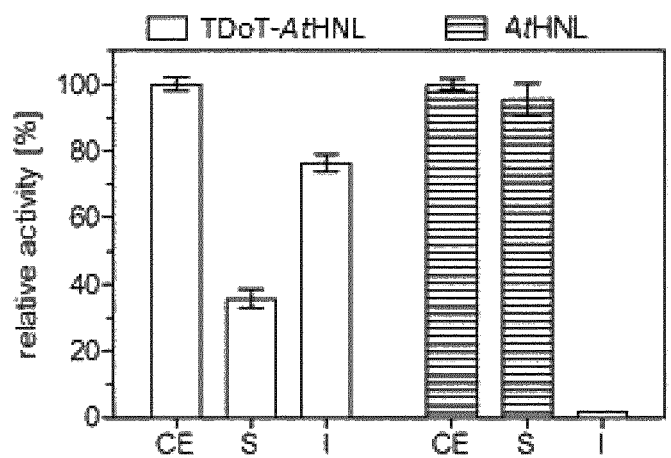
FIG. 1 shows the relative HNL activity of heterologously expressed TDoT-AtHNL fusion protein or heterologously expressed AtHNL, measured in different fractions (CE=crude cell extract, S=soluble fraction, and I=insoluble fraction) at pH 5.5 with a mandelonitrile end concentration of 13.4 mM. For the activity measurements the mandelonitrile cleavage assay was used in a continuous way, whereas suspensions containing the TDoT-AtHNL protein aggregates had to be assays in a discontinuous manner due to high particle densities. Error bars represent the standard deviation of the mean derived from three independent measurements.

The present invention will be described with respect to particular embodiments and/or reference to the figures, but the invention is not limited thereto but only by the claims. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

According to the first aspect, the invention provides protein aggregates, wherein said protein aggregates comprise a fusion protein, said fusion protein comprising a coiled-coil domain and a catalytic domain.

The term "fusion protein" in the context of the instant disclosure refers to a recombinant fusion protein. This is a protein created through genetic engineering of a fusion gene. This typically involves removing the stop codon from a nucleic acid sequence coding for a first protein, then appending the nucleic acid sequence encoding the second protein in frame. The resulting nucleic acid sequence will then be expressed by a cell as a single protein, the fusion protein. The fusion protein can be engineered to include the full amino acid sequence of both original proteins, or only a portion of either or both of the original protein's amino acid sequences. A portion of the amino acid sequence of the fusion protein originating from an original protein or a portion thereof is designated as domain. The domains of a fusion protein may be connected directly to one another or they may be connected by a linker. A linker is a short amino acid sequence within the fusion protein separating the domains from each other.

The term "coiled-coil domain" in the context of the instant disclosure refers to a structural motif in proteins in which 2 to 7 alpha-helices are coiled together like the strands of a rope. A coiled-coil domain is represented by an amino acid sequence comprising at least three heptad repeats, i.e. the repeated pattern, hxxhcxc, of hydrophobic (h) amino acid residues and charged (c) amino acid residues. This pattern is referred to as a heptad repeat. The positions in the heptad repeat are usually labeled abcdefg, where a and d are the hydrophobic positions, often being occupied by isoleucine, leucine, or valine. Alternatively and/or additionally a coiled-coil domain is defined in that the PCOILS webserver (http://toolkit.tuebingen.mpg.de/pcoils) predicts the heptad repeat pattern (hxxhcxc) in any of the 3 sequence windows (14, 21, 28 amino acids) with a score above 0.2 over 3 heptad repeats, using the MTIDK matrix. Alternatively and/or additionally a coiled-coil domain is defined in that the MARCOILS webserver http://toolkit.tuebingen.mpg.de/marcoil predicts at least 1 coiled-coil domain with a threshold of 1.0 within the sequence, using the 9FAM matrix. In the context of the instant disclosure, the term "coiled-coil domain" is additionally and/or alternatively defined in that the PCOILS webserver predicts a repeat pattern comprising two or more hydrophobic amino acid residues and two or more charged amino acid residues within a stretch of seven amino acid residues with a score above 0.2 over two repeats in any of the three sequence windows (14, 21, 28 amino acids).

Without wishing to be bound by theory, it is assumed that folding a polypeptide comprising an amino acid sequence with this heptad repeating pattern into an alpha-helical secondary structure causes the hydrophobic amino acid residues to be presented as a 'stripe' that coils gently around the helix in left-handed fashion, forming an amphipathic structure. The most favorable way for two such helices to arrange themselves in the water-filled environment of the cytoplasm is to wrap the hydrophobic strands against each other sandwiched between the hydrophilic amino acids. However, it appears that up to 7 polypeptides comprising a coiled-coil domain can wrap against each other.

The term "catalytic domain" in the context of the instant disclosure refers to the amino acid sequence within the fusion protein which originates from a protein or a fragment thereof which possesses enzymatic or catalytic activity at appropriate reaction conditions and in the presence of a substrate which is suitable for being converted to a product by the catalytic activity of said protein or fragment thereof.

The protein aggregate is a catalytically active protein aggregate. The term "catalytically active" in the context of the instant disclosure refers to the catalytic activity of an enzyme, a protein or a fragment thereof. I.e. "catalytically active" designates the capability of the enzyme, protein or fragment thereof for catalyzing a biochemical reaction provided that the reaction conditions are appropriate. The term "catalytically active" does not require that the protein aggregate, the fusion protein, domain, enzyme, protein or fragment thereof is possessing its catalytic activity at any time and under any condition. However, the protein aggregate, fusion protein, domain, enzyme, protein or fragment thereof is capable of possessing the catalytic activity in the presence of a substrate and under appropriate reaction conditions.

The protein aggregate is water-insoluble. That is, the protein aggregate does not dissolve in deionized water, distilled water or in a buffer at ambient temperature (i.e. at 21° C.) without additional means or supplements which are usually employed for dissolving protein aggregates in water, such as—for example—one or more detergents, one or more salts and/or one or more chaperones. Additionally and/or alternatively, insoluble protein aggregates are defined in that they do not dissolve in a cell lysis buffer, such as—for example—50 mM sodiumphosphate (pH 8.0) and 100 mM NaCl in deionized water, or 50 mM triethanolamine buffer (pH 8.0) containing 2 mM MgSO$_4$ and 0.1 mM thiaminediphosphate, and can be precipitated thereform by centrifugation for 20 min at 15,000×g.

In an embodiment, the fusion protein is an N-terminal fusion protein. The term "N-terminal fusion protein" in the context of the instant disclosure refers to fusion proteins wherein the coiled-coil domain is arranged at or in front of the amino terminal end of the catalytic domain. In the corresponding open reading frame encoding the N-terminal fusion protein, the nucleic acid sequence encoding the coiled-coil domain is arranged upstream or 5' of the nucleic acid sequence encoding the catalytic domain.

In another embodiment, the fusion protein is a C-terminal fusion protein. The term "C-terminal fusion protein" in the context of the instant disclosure refers to fusion proteins wherein the coiled-coil domain is arranged behind the carboxyl-terminal end of the catalytic domain. In the corresponding open reading frame encoding the C-terminal fusion protein, the nucleic acid sequence encoding the catalytic domain is arranged upstream or 5' of the nucleic acid sequence encoding the coiled-coil domain.

In an additional and/or alternative embodiment, the coiled-coil domain comprises at least three heptad repeats, the amino acid sequence of said heptad repeat being represented by hxxhcxc, wherein h represents a hydrophobic amino acid residue, c represents a charged amino acid residue, and x represents any amino acid residue. The hydrophobic amino acid residues may be based on an amino acid selected from the group consisting of alanine, isoleucine, leucine, valine, phenylalanine, tryptophan and tyrosine. The charged amino acid residue may be based on an amino acid selected from the group consisting of histidine, glutamic acid, aspartic acid, lysine and arginine. Alternatively and/or additionally the PCOILS webserver http://toolkit.tuebingen.mpg.de/pcoils predicts the heptad repeat pattern (hxxhcxc) in any of the 3 sequence windows (14, 21, 28 amino acids) with a score above 0.2 over 3 heptad repeats, using the MTIDK matrix. Alternatively and/or additionally the MARCOILS webserver http://toolkit.tuebingen.mpg.de/marcoil predicts at least 1 coiled-coil domain with a threshold of 1.0 within the sequence, using the 9FAM matrix.

In an additional and/or alternative embodiment, the coiled-coil domain is a domain comprising a repeat pattern comprising two or more hydrophobic amino acid residues and two or more charged amino acid residues within a stretch of seven amino acid residues, wherein the PCOILS webserver predicts the repeat pattern comprising two or more hydrophobic amino acid residues and two or more charged amino acid residues within a stretch of seven amino acid residues with a score above 0.2 over two repeats in any of the three sequence windows (14, 21, 28 amino acids).

In an additional and/or alternative embodiment, the coiled-coil domain is selected from the group of domains consisting of TDoT (SEQ ID NO: 1), 3HAMP (SEQ ID NO: 3), GCN4-P1 (SEQ ID NO: 5) and GCN4-pLI. (SEQ ID NO: 7).

In an additional and/or alternative embodiment, the catalytic domain originates from an enzyme or catalytically active protein or catalytically active fragment thereof which possesses the desired catalytic activity for a reaction of choice, preferably within a biotechnological or biochemical process for manufacturing a product or intermediate product.

In an additional and/or alternative embodiment, the fusion protein comprises a linker between the coiled-coil domain and the catalytic domain. Preferably, the linker is composed of a short amino acid sequence providing a flexible linkage between the coiled-coil domain and the catalytic domain. Thus, a preferred linker consists of an amino acid sequence which does not possess a rigid secondary structure such as a helix, coil or β-sheet.

In a preferred embodiment, the linker is composed of an amino acid sequence having 1 or at least 2, preferably at least 3, more preferably at least 5 amino acid residues, and not more than 25, preferably not more than 22 amino acid residues.

In an additional and/or alternative embodiment, the linker has an amino acid sequence selected from the group consisting of SEQ ID NO:15, SEQ ID NO:17 and SEQ ID NO:19.

In an additional and/or alternative embodiment, the fusion protein comprises a tag. The term "tag" in the context of the instant disclosure refers to a peptide sequence within the fusion protein. Such a peptide sequence is genetically grafted onto the recombinant fusion protein and may be used/present for various purposes. The tag may be selected from the group consisting of amino acid sequences represented by any one of SEQ ID NO: 21 to SEQ ID NO: 39.

TABLE 1

Overview of different tags that may be employed

| Name | Amino acid sequence | SEQ ID No. | Comment |
|---|---|---|---|
| AviTag | GLNDIFEAQKIEWHE | 21 | a peptide allowing biotinylation by the enzyme BirA and so the protein can be isolated by streptavidin |

TABLE 1-continued

Overview of different tags that may be employed

| Name | Amino acid sequence | SEQ ID No. | Comment |
|---|---|---|---|
| Calmodulin-tag | KRRWKKNFIAVSAANRFKKISSSGAL | 22 | a peptide bound by the protein calmodulin |
| polyglutamate tag | EEEEEE | 23 | a peptide binding efficiently to anion-exchange resin such as Mono-Q |
| E-tag | GAPVPYPDPLEPR | 24 | a peptide recognized by an antibody |
| FLAG-tag | DYKDDDDK | 25 | a peptide recognized by an antibody |
| HA-tag | YPYDVPDYA | 26 | a peptide recognized by an antibody |
| His-tag | HHHHHH | 27 | 5-10 histidines bound by a nickel or cobalt chelate; a preferred His-tag (Histidine-tag) has the amino acid sequence of SEQ ID No. 40. |
| Myc-tag | EQKLISEEDL | 28 | a short peptide recognized by an antibody |
| S-tag | KETAAAKFERQHMDS | 29 | |
| SBP-tag | MDEKTTGWRGGHVVEGLAGELEQLRARLEHHPQGQREP | 30 | a peptide which binds to streptavidin |
| Softag 1 | SLAELLNAGLGGS | 31 | for mammalian expression |
| Softag 3 | TQDPSRVG | 32 | for prokaryotic expression |
| Strep-tag | WSHPQFEK | 33 | a peptide which binds to streptavidin or the modified streptavidin called streptactin |
| TC tag | CCPGCC | 34 | a tetracysteine tag that is recognized by FlAsH and ReAsH biarsenical compounds |
| V5 tag | GKPIPNPLLGLDST | 35 | a peptide recognized by an antibody |
| VSV-tag | YTDIEMNRLGK | 36 | a peptide recognized by an antibody |
| Xpress-tag | DLYDDDDK | 37 | |
| Isopep-tag | TDKDMTITFTNKKDAE | 38 | a peptide which binds covalently to pilin-C protein |
| SpyTag | AHIVMVDAYKPTK | 39 | a peptide which binds covalently to SpyCatcher protein |

The fusion protein may comprise the tag at its N-terminal end and/or at its C-terminal end.

However, the fusion protein does not comprise a solubilization tag, i.e. a peptide or protein tag that is typically used to assist proper folding of recombinant proteins being expressed in bacterial host cells. The group of solubilization tags which are not suitable for being included in a fusion protein for providing the protein aggregate includes the chitin-binding protein, the maltose-binding protein, the glutathione-S-transferase, thioredoxin and poly(NANP).

In an additional and/or alternative embodiment, the fusion protein may comprise a peptide sequence providing a cleavage site for an endopeptidase such as for example the Tobacco Etch Virus protease (TEV cleavage site: ENLYFQS (SEQ ID NO: 69)), thrombin (thrombin cleavage site: LVPRGS (SEQ ID NO: 70)), Factor Xa (Factor Xa cleavage site: IEGR (SEQ ID NO: 71) and IDGR (SEQ ID NO: 72)) and the enteropeptidase (enteropeptidase cleavage site: DDDDK (SEQ ID NO: 73)). Such a peptide sequence can be provided in the fusion protein for removing the tag and/or for separating the coiled-coil domain and the catalytic domain from each other. Thus, the amino acid sequence for providing an endopeptidase cleavage site may be integral part of the linker sequence. The protein aggregate according to the first aspect is water-insoluble and capable of performing catalytic activity provided by the catalytic domain under appropriate reaction conditions. The protein aggregate can be easily produced in large quantities without the need of excessive purification and solubilization of the catalytic activity providing polypeptide. The catalytic activity of the protein aggregate is more stable than the catalytic activity of the original protein the catalytic domain of the fusion protein is obtained from. Thus, the yield of product obtainable by the reaction of the catalytic domain is better, in particular if the catalytic reaction is performed at non-optimal conditions leading to unfolding and/or denaturing of otherwise dissolved proteins in the reaction mixture.

According to the second aspect, a method for producing a protein aggregate comprising a fusion protein, wherein said fusion protein comprises a coiled-coil domain and a catalytic domain is provided.

In an embodiment, the method comprises expressing a gene fusion comprising an open reading frame encoding the fusion protein comprising a coiled-coil domain and a catalytic domain, and optionally a linker and/or a tag, heterogeneously in a host cell, lysing the host cell having said fusion protein expressed, and separating the protein aggregates from the water-soluble content of said host cell.

The host cell may be any cell useful in the recombinant production of a polypeptide of the present invention, e.g., a prokaryote or a eukaryote.

In an embodiment the host cell is a bacterial cell. Bacterial cells are simple to cultivate, can be propagated in high density in an appropriate broth or culture medium. Using appropriate expression vectors for heterologous expression of the recombinant fusion gene, the expression of said fusion gene can be induced at a desired point of time in that—for example an expression-inducing compound is added to the culture broth bearing the bacterial host cells. In a preferred embodiment, said bacterial host cell is selected from the group consisting of *Acinetobacter* sp., *Agrobacterium* sp., *Alcaligenes* sp., *Brevibacterium* sp., *Bacillus* sp. (e.g., *Bacillus subtilis, Bacillus megaterium, Bacillus licheniformis*, etc.), *Campylobacter* sp., *Clostridium* sp., *Corynebacterium* sp., *Deinococcus* sp., *Enterobacter* sp., *Enterococcus* sp., *Erwinia* sp., *Escherichia* sp. (e.g., *Escherichia coli*), *Flavobacterium* sp., *Fusobacterium* sp., *Geobacillus* sp., *Helicobacter* sp. *Ilyobacter* sp., *Klebsiella* sp., *Lactobacillus* sp., *Lactococcus* sp. (e.g., *L. lactis*), *Legionella* sp., *Mycobac-* terium sp., *Neisseria* sp., *Nitrosomonas* sp., *Novosphingobium* sp., *Oceanobacillus* sp., *Paracoccus* sp., *Proteus* sp. (e.g., *Proteus mirabilis*), *Pseudomonas* sp. (e.g., *P. fluorescens* or *P. stutzerei*), *Ralstonia* sp. (e.g., *Ralstonia eutropha*), *Rhodbacter* sp. (e.g. *Rhodobacter capsulatus*), *Rhodopseudomonas* sp., *Salmonella* sp., *Shigella* sp., *Staphylococcus* sp. (e.g., *S. carnosus*), *Streptococcus* sp., *Streptomyces* sp., *Thermus* sp., *Ureaplasma* sp., *Vibrio* sp.and *Zymomonas* sp.

In another embodiment, the host cell is an archaea. Preferably, the archaea host cell is selected from the group consisting of Aeropyrum sp., *Archaeoglobus* sp., *Halobacterium* sp., *Methanobacterium* sp., *Methanobrevibacter* sp., *Methanocaldococcus* sp., *Methanococcus* sp., *Methanopyrus* sp., *Methanosarcina* sp., *Methanosphaera* sp., *Pyrobaculum* sp. and *Thermoplasma* sp.

In another embodiment, the host cell is a fungus. Preferable fungi host cells are selected from the group consisting of *Acremonium* sp., *Aspergillus* sp., *Aureobasidium* sp., *Bjerkandera* sp., *Ceriporiopsis* sp., *Chrysosporium* sp., *Coprinus* sp., *Coriolus* sp., *Cryptococcus* sp., *Filibasidium* sp., *Fusarium* sp., *Humicola* sp., *Magnaporthe* sp., *Mucor* sp., *Myceliophthora* sp., *Neocallimastix* sp., *Neurospora* sp., *Paecilomyces* sp., *Penicillium* sp., *Phanerochaete* sp., *Phlebia* sp., *Piromyces* sp., *Pleurotus* sp., *Schizophyllum* sp., *Talaromyces* sp., *Thermoascus* sp., *Thielavia* sp., *Tolypocladium* sp., *Trametes* sp., and *Trichoderma* sp.

In another embodiment, the host cell is a yeast. Preferable yeast host cells are selected from the group consisting *Candida* sp., *Cytophagia* sp., *Hansenula* sp., *Humicola* sp., *Kluyveromyces* sp., *Mucor* sp., *Myceliophthora* sp., *Pichia* sp., *Rhizoctonia* sp., *Saccharomyces* sp., *Schizosaccharomyces* sp., and *Yarrowia* sp.

The protein aggregates are water insoluble and can be easily separated from the water soluble content of the host cell, for example by filtration and/or centrifugation.

According to the third aspect, the invention provides the use of the protein aggregates according to the first and/or second aspect in a catalytic reaction. Thus, in use the catalytic domain of the fusion protein catalyzes the chemical reaction in that the substrate of the chemical reaction is brought into contact with the protein aggregate in an appropriate reaction buffer and at appropriate reaction temperature. The catalytic reaction may be performed under agitation. The protein aggregates may be used in a continuously operating process or in a batch process.

Using the protein aggregates of the present invention in a catalytic reaction provides several advantages of using soluble or immobilized enzymes. The protein aggregates do not require adherence to any material, yet they can be easily removed from the reaction mixture due to their insolubility. Moreover, the stability of the catalytic activity of the protein aggregate is improved compared to solubilized fusion proteins and/or enzymes. Hence, the catalytic activity of the protein aggregates has a longer half-life than the catalytic activity of the corresponding native enzyme. In addition, the protein aggregates may be used in reaction conditions which are potentially harmful to the native enzyme, for example if organic solvents are included in the reaction mixture.

According to a further aspect, the present invention provides the use of a protein aggregate according to the first and/or second aspect for stabilizing the catalytic activity of the catalytic domain within the fusion protein of said protein aggregate. Stabilizing the catalytic activity of the catalytic domain is understood to be with respect to the catalytic activity of the corresponding native protein or enzyme, said catalytic domain is derived from.

According to a further aspect, the invention provides a nucleic acid molecule encoding a fusion protein, wherein said fusion protein comprises a coiled-coil domain and a catalytic domain.

The nucleic acid molecule comprises a nucleotide sequence representing an open reading frame which encodes the fusion protein comprising a coiled-coil domain and a catalytic domain. The expression "nucleic acid molecule comprising a nucleotide sequence" does not only refer to nucleic acid molecules consisting of said nucleotide sequence, but also refers to nucleic acid molecules having at least one additional nucleotide.

In an additional and/or alternative embodiment, the open reading frame comprises a nucleotide sequence encoding the coiled-coil domain of the fusion protein. The nucleotide sequence encoding the coiled-coil domain is selected from the group of nucleotide sequences encoding TDoT, 3HAMP, GCN4-p1 and GCN4-pLI. In an additional and/or alternative embodiment, the nucleotide sequence encoding the coiled-coil domain is selected from the group of nucleotide sequences encoding the amino acid sequences selected from the group consisting of SEQ ID NO: 1, SEQ ID NO: 3, SEQ ID NO: 5 and SEQ ID NO: 7. In an additional and/or alternative embodiment, the nucleotide sequence encoding the coiled-coil domain is selected from the group of nucleotide sequences consisting of SEQ ID NO: 2, SEQ ID NO: 4, SEQ ID NO: 6 and SEQ ID NO: 8. In an additional and/or alternative embodiment, the nucleotide sequence encoding the coiled-coil domain is selected from the group of nucleotide sequences having at least 80% identity, preferably at least 90% identity, more preferably at least 95% identity, and even more preferably at least 98% or 99% identity to a nucleotide sequence selected from the group of nucleotide sequences consisting to SEQ ID NO: 2, SEQ ID NO: 4, SEQ ID NO: 6 and SEQ ID NO: 8. In another and/or additional embodiment, the nucleotide sequence encoding the coiled-coiled domain is selected from the group consisting of nucleotide sequences encoding a homolog, analog or ortholog of coiled-coil domain selected from the group consisting of TDoT, 3HAMP, GCN4-p1 and GCN4-pLI.

The open reading frame further comprises a nucleotide sequence encoding the catalytic domain of the fusion protein.

In an embodiment, the catalytic domain originates, or is derived from, an enzyme belonging to the class EC 1, preferably EC 1.1 (subclass), more preferably EC 1.1.1 (sub-sub-class), and most preferably EC 1.1.1.1.

In an embodiment, the catalytic domain originates, or is derived from, an enzyme belonging to the class EC 2, preferably EC 2.2 (subclass), more preferably EC 2.2.1 (sub-sub-class), and most preferably EC 2.2.1.9.

In an embodiment, the catalytic domain originates, or is derived from, an enzyme belonging to the class EC 3, preferably EC 3.1 (subclass), more preferably EC 3.1.1 (sub-sub-class), and most preferably EC 3.1.1.1 or EC 3.1.1.74.

In an embodiment, the catalytic domain originates, or is derived from, an enzyme belonging to the class EC 4, preferably EC 4.1 (subclass), more preferably EC 4.1.2 (sub-sub-class), and most preferably EC 4.1.2.10 or EC 4.1.2.38.

In an embodiment, the nucleotide sequence encoding the catalytic domain is selected from the group of nucleotide sequences encoding AtHNL, MenD, BsLA, BtADH, LCC, PfBAL, and RADH. In an additional and/or alternative embodiment, the nucleotide sequence encoding the catalytic domain is selected from the group of nucleotide sequences encoding the amino acid sequences selected from the group consisting of SEQ ID NO: 9, SEQ ID NO: 11, SEQ ID NO: 13, SEQ ID NO: 74, SEQ ID NO: 78, SEQ ID NO: 82, and SEQ ID NO: 86. In an additional and/or alternative embodiment, the nucleotide sequence encoding the catalytic domain is selected from the group of nucleotide sequences selected from the group consisting of SEQ ID NO: 10, SEQ ID NO: 12, SEQ ID NO: 14, SEQ ID NO: 75, SEQ ID NO: 79, SEQ ID NO: 83, and SEQ ID NO: 87. In an additional and/or alternative embodiment, the nucleotide sequence encoding the catalytic domain is selected from the group of nucleotide sequences having at least 80% identity, preferably at least 90% identity, more preferably at least 95% identity, and even more preferably at least 98% or 99% identity to a nucleotide sequence selected from the group of nucleotide sequences consisting to SEQ ID NO: 10, SEQ ID NO: 12, SEQ ID NO: 14, SEQ ID NO: 75, SEQ ID NO: 79, SEQ ID NO: 83, and SEQ ID NO: 87. In another and/or additional embodiment, the nucleotide sequence encoding the catalytic domain is selected from the group consisting of nucleotide sequences encoding a homolog, analog or ortholog of catalytic domain selected from the group consisting of AtHNL, MenD, BsLA, BtADH, LCC, PfBAL, and RADH, or from the group consisting of nucleotide sequences encoding a homolog, analog or ortholog of SEQ ID NO: 10, SEQ ID NO: 12, SEQ ID NO: 14, SEQ ID NO: 75, SEQ ID NO: 79, SEQ ID NO: 83, and SEQ ID NO: 87.

In an additional and/or alternative embodiment, the open reading frame further comprises a nucleotide sequence encoding a linker. Said nucleotide sequence encoding the linker may be present between the nucleotide sequence encoding the coiled-coil domain and the nucleotide sequence encoding the catalytic domain. In an additional and/or alternative embodiment, the nucleotide sequence encoding the linker is a nucleotide sequence encoding one of the amino acid sequences set forth in the group consisting of SEQ ID NO: 15, SEQ ID NO: 17 and SEQ ID NO: 19. In an additional and/or alternative embodiment, the nucleotides sequence encoding the linker is selected from the group consisting of SEQ ID NO: 16, SEQ ID NO: 18 and SEQ ID NO: 20.

In an additional and/or alternative embodiment, the open reading frame further comprises a nucleotide sequence encoding a tag. In an additional and/or alternative embodiment the nucleotide sequence encoding a tag is selected from the nucleotides sequences encoding a tag comprising an amino acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38 and SEQ ID NO: 39.

In an additional and/or alternative embodiment, the nucleic acid molecule comprises a recombinant fusion gene, the recombinant fusion gene comprising an open reading frame comprising a nucleotide sequence encoding the fusion protein comprising a coiled-coil domain and a catalytic domain, and optionally a linker and/or a tag as described herein before. In said recombinant fusion gene, the open reading frame is operatively connected to at least one regulatory element.

The term "regulatory element" refers to a nucleotide sequence which is not part of the open reading frame encoding the fusion protein, but mediates and/or regulates expression of the protein coding open reading frame. Regulatory elements are, for example, promotors, cis-regulatory elements, enhancer, introns or terminators. Depending on the kind of regulatory element, it is located upstream (i.e. 5' of) or downstream (i.e. 3' of) the protein coding nucleotide sequence.

In an additional and/or alternative embodiment, said nucleic acid molecule is a vector or a mobile genetic element. A vector is understood to be a transport vehicle for the nucleotide sequence encoding the fusion protein or the recombinant gene comprising the nucleotide sequence encoding the fusion protein. Vectors comprise plasmids, cosmids, artificial bacterial chromosomes and phages. Mobile genetic elements are nucleotide sequences having alterable positions within the genome of an organism or cell. Mobile genetic elements are—for example—transposons, retroelements, inteins and inserting plasmids and some bacteriophages such as phage Mu.

According to yet another aspect, the present invention provides a host cell comprising a nucleic acid molecule encoding the fusion protein comprising a coiled-coil domain and a catalytic domain. According to still another aspect, the invention provides a host cell comprising protein aggregates comprising a fusion protein which comprises at least a coiled-coil domain and a catalytic domain.

In preferred embodiments, the nucleic acid molecule and/or the protein aggregate are selected from the group of nucleic acid molecules and protein aggregates as described herein before.

In a preferred embodiment, the host cell is a prokaryotic host cell. In an additional and/or alternative embodiment, the host cell is a unicellular host cell.

In an additional and/or alternative embodiment, the host cell is a bacterial cell selected from the group consisting of *Acinetobacter* sp., *Agrobacterium* sp., *Alcaligenes* sp., *Brevibacterium* sp., *Bacillus* sp. (e.g., *Bacillus subtilis, Bacillus megaterium, Bacillus licheniformis*, etc.), *Campylobacter* sp., *Clostridium* sp., *Corynebacterium* sp., *Deinococcus* sp., *Enterobacter* sp., *Enterococcus* sp., *Erwinia* sp., *Escherichia* sp. (e.g., *Escherichia coli*), *Flavobacterium* sp., *Fusobacterium* sp., *Geobacillus* sp., *Helicobacter* sp., *Ilyobacter* sp., *Klebsiella* sp., *Lactobacillus* sp., *Lactococcus* sp. (e.g., *L. lactis*), *Legionella* sp., *Mycobacterium* sp., *Neisseria* sp., *Nitrosomonas* sp., *Novosphingobium* sp., *Oceanobacillus* sp., *Paracoccus* sp., *Proteus* sp. (e.g., *Proteus mirabilis*), *Pseudomonas* sp. (e.g., *P. fluorescens* or *P. stutzerei*), *Ralstonia* sp. (e.g., *Ralstonia eutropha*), *Rhodobacter* sp. (e.g. *Rhodobacter capsulatus*), *Rhodopseudomonas* sp., *Salmonella* sp., *Shigella* sp., *Staphylococcus* sp. (e.g., *S. carnosus*), *Streptococcus* sp., *Streptomyces* sp., *Thermus* sp., *Ureaplasma* sp., *Vibrio* sp., and *Zymomonas* sp.

In an additional and/or alternative embodiment, the host cell is an archaea cell, preferably selected from the group consisting of Aeropyrum sp., *Archaeoglobus* sp., *Halobacterium* sp., *Methanobacterium* sp., *Methanobrevibacter* sp., *Methanocaldococcus* sp., *Methanococcus* sp., *Methanopyrus* sp., *Methanosarcina* sp., *Methanosphaera* sp., *Pyrobaculum* sp., and *Thermoplasma* sp.

In an alternative embodiment, the host cell is a eukaryotic host cell. In an additional and/or alternative embodiment, the host cell is a unicellular host cell.

In an additional and/or alternative embodiment, the host cell is a fungal cell, preferably selected from the group of fungi consisting of *Acremonium* sp., *Aspergillus* sp., *Aureobasidium* sp., *Bjerkandera* sp., *Ceriporiopsis* sp., *Chrysosporium* sp., *Coprinus* sp., *Coriolus* sp., *Cryptococcus* sp., *Filibasidium* sp., *Fusarium* sp., *Humicola* sp., *Magnaporthe* sp., *Mucor* sp., *Myceliophthora* sp., *Neocal-*

*limastix* sp., *Neurospora* sp., *Paecilomyces* sp., *Penicillium* sp., *Phanerochaete* sp., *Phlebia* sp., *Piromyces* sp., *Pleurotus* sp., *Schizophyllum* sp., *Talaromyces* sp., *Thermoascus* sp., *Thielavia* sp., *Tolypocladium* sp., *Trametes* sp., and *Trichoderma* sp.

In an additional and/or alternative embodiment, the host cell is a yeast cell, preferably selected from the group of yeasts consisting of *Candida, Cytophagia* sp., *Hansenula* sp., *Humicola* sp., *Kluyveromyces* sp., *Mucor* sp., *Myceliophthora* sp., *Pichia* sp., *Rhizoctonia* sp., *Saccharomyces* sp., *Schizosaccharomyces* sp., and *Yarrowia* sp.

EXAMPLES

Example 1: Selection of Coiled-Coil Domains

For producing fusion proteins, the following coiled coil domains were selected: TDoT: The coiled-coil domain designated "TDoT" is a short coiled-coil domain composed of 51 amino acids (SEQ ID NO: 1). It is based on the tetramerization domain of the protein tetrabrachion from the deep sea organism *Staphylothermus marinus*. The TDoT domain has been described to provide tetrameric coiled-coil structures. The nucleotide sequence encoding TDoT as used in the examples is set forth in SEQ ID NO: 2.

3HAMP: The coiled-coiled domain 3HAMP consists of the first 172 amino acids of the *Pseudomonas aeruginosa* Aer2 protein. The HAMP3 domain (SEQ ID NO: 3) has been described to generate a complex dimeric coiled-coil structure. The nucleotide sequence encoding 3HAMP as used in the examples is set forth in SEQ ID NO: 4.

GCN4-p1: The GCN-p1 domain consists of an amino acid sequence set forth in SEQ ID NO: 5. The GCN4-p1 domains consists of amino acid residues 1 to 34 of the *Saccharomyces cerevisiae* transcription factor GCN4. The GCN-p1 domain has been described to provide dimeric coiled-coil structures. The nucleotide sequence encoding GCN4-p1 as used in the examples is set forth in SEQ ID NO: 6.

GCN4-pLI: The GCN-pLI domain (SEQ ID NO: 7) is a variant of the GCN-p1 domain, wherein all a and d position residues of the heptad repeat were substituted against leucine and isoleucine, respectively. The GCN-pLI domains has been described to provide tetrameric coiled-coil structures. The nucleotide sequence encoding GCN4-pLI as used in the examples is set forth in SEQ ID NO: 8.

Example 2: Selection of Catalytic Domains

As catalytic domains, proteins of different complexity were chosen BsLA: The catalytic domain BsLA (SEQ ID NO: 13) is based on the Lipase A from *Bacillus subtilis*. The Enzyme classification is EC 3.1.1.1. The catalytic domain BsLA corresponds to the mature Lipase A, i.e. the mature enzyme without the leader sequence which is encoded by the *B. subtilis* lipase A gene but which is removed from the polypeptide upon its maturation and secretion. The nucleotide sequence encoding BsLA (bsla) as used in the examples is set forth in SEQ ID NO: 14.

AtHNL: The catalytic domain AtHNL (SEQ ID No. 9) is based on the hydroxynitril lyase of *Arabidopsis thaliana*. The Enzyme classification is EC 4.1.2.10. The native hydroxynitril lyase of *A. thaliana* is a dimer. The nucleotide sequence encoding AtHNL (athnl) as used in the examples is set forth in SEQ ID NO: 10.

MenD: The catalytic domain MenD (SEQ ID NO: 11) is based on the 2-succinyl-5-enolpyruvyl-6-hydroxy-3-cyclohexene-1-carboxylase synthase from *E. coli*. It is also designated EcMenD. The Enzyme classification is EC 2.2.1.9. The native MenD is an enzyme of high complexity. It is believed to be tetrameric and only catalytically active if it is present at least as a dimer due to the necessary cofactor thiamine diphosphate which binds at the interface between two monomers. The nucleotide sequence encoding MenD (mend) as used in the examples is set forth in SEQ ID NO: 12.

BtADH: The catalytic domain BtADH (SEQ ID NO: 74) is based on the Alcohol Dehydrogenase (ADH) from *Bacillus thuringiensis*. The Enzyme classification is EC 1.1.1.1. The nucleotide sequence encoding BtADH as used in the examples is set forth in SEQ ID NO: 75.

LCC: The catalytic domain LCC (SEQ ID NO: 78) is a LC Cutinase, a Cutinase from metagenomic origin (Sulaiman, S., Yamato, S., Kanaya, E., Kim, J. J., Koga, Y., Takano, K. and Kanaya, S. (2012) Isolation of a novel cutinase homolog with polyethylene terephthalate-degrading activity from leaf-branch compost by using a metagenomic approach. Appl. Environ. Microbiol. 78 (5), 1 556-1 562). The Enzyme classification is EC 3.1.1.74. The nucleotide sequence encoding LCC as used in the examples is set forth in SEQ ID NO: 79.

PfBAL: The catalytic domain PfBAL (SEQ ID NO: 82) is based on the Benzaldehyde Lyase from *Pseudomonas fluorescens*. The Enzyme classification is EC 4.1.2.38. The nucleotide sequence encoding PfBAL as used in the examples is set forth in SEQ ID NO: 83.

RADH: The catalytic domain RADH (SEQ ID NO: 86) is based on Alcohol Dehydrogenase (ADH) from *Ralstonia* sp. The Enzyme classification is EC 1.1.1.1. The nucleotide sequence encoding RADH as used in the examples is set forth in SEQ ID NO: 87.

Example 3: Cloning

A basic vector comprising a nucleotide sequence encoding a histidine-tag, the TDoT domain and a linker region comprising a nucleotide sequence coding for a factor Xa protease cleavage site and a three times GGGS amino acid pattern was cloned and named pTDoT-Linker in that the TDoT-Xa-L region was cut out of the synthesis vector pEX-A-TDoT-Linker from Eurofins Genomics (Ebersberg, Germany) using the restriction sites NdeI and SalI and ligated into the empty vector pET28a (Merck Millipore Corporation, Darmstadt). The nucleic acid molecules coding for the target enzymes were amplified via standard PCR methods with primers containing BamHI and SalI restriction sites for MenD and BsLa, while the AtHNL was cloned via BamHI and NotI. The resulting PCR products were cut with the respective restriction enzymes and ligated into the open plasmid pTDoT-Xa-L. Based on the complete vectors the corresponding controls were cloned by removing the TDoT-tag and the linker region with the restriction enzymes NdeI and SpeI and reinserting the linker region without the tag. For this procedure two primers with the desired sequence were designed in a way that after an annealing step in a PCR cycler (85° C., 10 min; 85° C., 20 s, 75 cycles, −1° C. per cycle) they have overhanging ends resembling the necessary restriction sites. The product of this step can be directly ligated into the cut base vector. All finalized plasmids were sequenced before use.

TABLE 2

Summary of the primers used in the various amplification reactions for generating fusion genes and controls.

| SEQ ID No: | nucleotide sequence | comment |
|---|---|---|
| 57 | ATA TAT GGA TCC ATG GAG AGG AAA CAT CAC TTC G | Forward primer for amplification of athnl, providing BamHI restriction close to the 5' end of the amplification product; for cloning of pTDoT-Linker-AtHNL. |
| 58 | ATA TAT GCG GCC GCT TAC ATA TAA TCG GTG GCA ATA G | Reverse primer for amplification of athnl providing NotI restriction site close to 3' end of the amplification product; for cloning of pTDoT-Linker-AtHNL. |
| 59 | ATA TAT GGA TCC GCT GAA CAC AAT CCA GTC GTT ATG | Forward primer for amplification of bsla providing BamHI restriction close to the 5' end of the amplification product; for cloning of pTDoT-Linker-BsLA. |
| 60 | CTC GAG TGC GGC CGC AAG CTT GTC GAC | Reverse primer for amplification of bsla providing NotI restriction site close to 3' end of the amplification product; for cloning of pTDoT-Linker-BsLA. |
| 61 | ATA TAT GGA TCC ATG TCA GTA AGC GCA TTT AAC | Forward primer for amplification of ecmend providing BamHI restriction close to the 5' end of the amplification product; for cloning of pTDoT-Linker-EcMenD. |
| 62 | ATA TAT GTC GAC TCA TAA ATG GCT TAC CTG CG | Reverse primer for amplification of ecmend providing SalI restriction close to the 3' end of the amplification product; for cloning of pTDoT-Linker-EcMenD. |
| 63 | TAT GAC TAG TAT TGA AGG CCG TG | Forward primer for generating a PCR product comprising NdeI/SpeI overlaps; for cloning control constructs lacking tdot. |
| 64 | CTA GCA CGG CCT TCA ATA CTA GTC A | Reverse primer for generating a PCR product comprising NdeI/SpeI overlaps; for cloning control constructs lacking tdot. |

Construction of TDoT-AtHNL-ΔL

For generating a fusion protein comprising a coiled-coil domain and a catalytic domain, but comprising a truncated linker lacking a flexible poly-GGGS-linker, the gene fragment coding for the tdot gene and the 3' base sequence coding for the protease Factor Xa cleavage site was synthesized by Eurofins Genomics (Ebersberg, Germany). This fragment and the sequence coding for the AtHNL were amplified by PCR with appropriate primers and afterwards fused by overlap extension PCR. The obtained PCR product was subsequently hydrolyzed with the restriction enzymes NdeI and NotI and ligated into the identically hydrolyzed expression vector pET28a. The sequence of the gene fusion was verified by sequencing before further use.

Construction of Expression Plasmids Encoding 3HAMP-Comprising Fusion Proteins

The nucleic acid coding for the coiled-coil domain 3HAMP, further containing a 3'-linker region (coding for a 3-fold GGGS repeat, the protease Xa recognition site (amino acid sequence: IEGRASGGGSGGGSGGGS) and the necessary restriction sites for cloning was synthesized by Eurofins Genomics (Ebersberg, Germany) and supplied on a plasmid (pEX-A-3HAMP-Linker). The basic expression vector containing the inclusion body inducing 3HAMP tag including the C-terminal linker region was sub-cloned from pEX-A-3HAMP-Linker into pET28a using the restriction endonucleases NdeI and SalI resulting in p3HAMP-Linker. The genes coding for the target enzymes were amplified via standard PCR methods using oligonucleotide primers (Table 3) containing BamHI and SalI restriction sites for BsLA (BamHI_BsLA_for; pET28_SalI_NotI_rev). The AtHNL encoding gene was amplified containing 5' and 3' restriction endonuclease recognition sites for BamHI and NotI (BamHI_HNL_for; HNL_oe_rev_neu). The resulting PCR products were hydrolyzed with the respective restriction enzymes and ligated into the similarly digested 3HAMP-Linker plasmid, yielding the plasmids p3HAMP-BsLA and p3HAMP-AtHNL.

Construction of Expression Plasmids Encoding GCN4-Comprising Fusion Proteins

The gene fusions coding for GCN4-p1-BsLA and GCN4-pLI-BsLA, consisting of the respective coiled-coil domain coding sequence fused N-terminally to the BsLA domain, were custom synthesized by Eurofins MWG Operon GmbH (Ebersberg, Germany). Both DNA fragments contained an NdeI and SalI restriction endonuclease recognition site at the 5'- and 3'-end, respectively. The codon usage of the gene fusions was adapted to the E. coli codon usage during gene synthesis. The gene fusions (obtained in a pEX-A vector) were subcloned by hydrolyzing the corresponding pEX-A vector DNA with NdeI and SalI and ligated into a similarly hydrolyzed pET28a vector (Merck Millipore, Darmstadt, Germany). All sequences were verified by sequencing.

TABLE 3

Oligonucleotides used for amplification of the BsLA and AtHNL encoding gene fragments

| SEQ ID No. | Nucleotide sequence (5' → 3') | Comment |
|---|---|---|
| 65 | ATA TAT GGA TCC GCT GAA CAC AAT CCA GTC GTT ATG | BamHI_BsLA_for |
| 66 | CTC GAG TGC GGC CGC AAG CTT GTC GAC | pET28_SalI_NotI_rev |

TABLE 3-continued

Oligonucleotides used for amplification of the BsLA and AtHNL encoding gene fragments

| SEQ ID No. | Nucleotide sequence (5' → 3') | Comment |
|---|---|---|
| 67 | ATA TAT GGA TCC ATG GAG AGG AAA CAT CAC TTG G | BamHI_HNL_for |
| 68 | ATA TAT GCG GCC GCT TAC ATA TAA TCG GTG GCA ATA G | HNL_oe_rev_neu |

The resulting fusion proteins and the fusion genes encoding these fusion proteins are summarized in table 4. Note: Further fusion proteins and fusion genes are shown in further examples.

TABLE 4

Summary of the fusion proteins and the corresponding fusion genes that were generated and used.

| Name | Fusion protein | Fusion gene |
|---|---|---|
| TDoT-AtHNL | SEQ ID No. 41 | SEQ ID No. 42 |
| TDoT-AtHNL-ΔL | SEQ ID No. 43 | SEQ ID No. 44 |
| TDoT-BsLA | SEQ ID No. 45 | SEQ ID No. 46 |
| TDoT-MenD | SEQ ID No. 47 | SEQ ID No. 48 |
| 3HAMP-AtHNL | SEQ ID No. 49 | SEQ ID No. 50 |
| 3HAMP-BsLA | SEQ ID No. 51 | SEQ ID No. 52 |
| GCN4-p1-BsLA | SEQ ID No. 53 | SEQ ID No. 54 |
| GCN4-pLI-BsLA | SEQ ID No. 55 | SEQ ID No. 56 |

Example 4: Gene Expression and Protein Production

The expression of all genes for protein aggregate production and the controls was performed under the same conditions. Therefore a 25 ml LB medium overnight pre culture was inoculated with an *E. coli* BL21 (DE3) clone containing the target plasmid from a fresh transformation LB agar plate. The culture was shaken in a 250 ml Erlenmeyer shake flask with 130 rpm at 37° C. With this culture the main culture of 500 ml auto induction medium in a 5 l shake flask was inoculated to an $OD_{600}$ of 0.05. The medium consists of TB-Medium from Carl Roth GmbH & Co. KG (Karlsruhe, Germany) with supplemented glycerol and additional glucose to suppress gene expression in the first hours of incubation and lactose for the induction of expression in a later phase. Cultivation was performed for 3 h at 37° C. and 130 rpm followed by a prolonged incubation for another 69 h at 15° C. and 130 rpm. After the cultivation the cells were harvested by centrifugation and were directly used for cell disruption and purification or stored at −20° C.

Example 5: Cell Disruption, Fractionation and Purification of Protein Aggregates For the cell disruption, fractionation and purification of protein aggregates appropriate buffers for the different enzymes were used (AtHNL: 50 mM sodium phosphate pH 8, 100 mM NaCl; for the AtHNL-CatIBs in the last washing step of the purification a 50 mM citrate phosphate buffer pH 5.5 was used to reduce side reactions in the synthesis reaction; MenD buffer: 50 mM triethanolamine (TEA) pH 8, 2 mM $MgSO_4$, 0.1 mM thiamine diphosphate (ThDP)). In the first step a 10% (w/v) cell suspension in buffer was prepared and frozen over night at −80° C. The next day the cells were thawed at room temperature and disrupted using a FrenchPress pressure homogenization system (Thermo Electron Corp., Needahm Flights, Mass.) in three passings under the stetting high with 1000 psi. Directly after this step the crude cell extract was frozen again at −80° C. overnight to enhance the efficiency of the cell disruption. After thawing the extract at room temperature a sample for analysis of protein content via SDS-PAGE and enzyme activity was taken and the rest was used for fractionation into soluble and insoluble parts via centrifugation (15,000 g, 30 min). The obtained pellet was resuspended in the starting volume of buffer and samples for further analysis from both fractions were taken. For further purification of the protein aggregate-containing insoluble fraction these washing steps consisting of centrifugation and resuspension were repeated three times using the buffers listed above, whereas for the AtHNL-comprising protein aggregates the buffer was changed in the last washing step. After the last centrifugation the pelleted protein aggregates were stored until use at −80° C.

Example 6: Lyophilization, Quantification of Protein Aggregate Yields and Protein Content The wet weight of different protein aggregates was measured directly after purification. For lyophilization a 10% (w/v) protein aggregate-containing suspension in ultra-pure water was prepared, frozen in liquid nitrogen, stored overnight at −80° C. and lyophilized (Lyovac GT2, SRK Systemtechnik, Riedstadt-Goddelau, Germany). Afterwards the dry weight was determined and the protein content of a defined amount of protein aggregates was analyzed by denaturation in 6 M guanidine hydrochloride followed by measuring the absorbance at 280 nm. Protein concentrations were calculated using the theoretical extinction coefficients.

Example 7: Photometric Mandelonitrile Cleavage Assay for Quantification of HNL Activity Mandelonitrile cleavage reactions were performed in that the accumulation of benzaldehyde, which is formed as one reaction product of the HNL-catalyzed cleavage of rac-mandelonitrile, was photometrically monitored at 280 nm (Spectramax, Molecular Devices, Sunnyvale, Calif., USA). All measurements were carried out in 10-mm quartz cuvettes at 25° C. in assay buffer (50 mM sodium acetate buffer) with a total assay volume of 1 ml. To start the reactions rac-mandelonitrile was added (67 mM in 50 mM citrate phosphate buffer pH 3.5) to a final concentration of 13.4 mM to the assay. The respective control in buffer (without enzyme) was subtracted from all measurements, to account for non-enzymatic mandelonitrile cleavage. All measurements were performed at least in triplicate. Enzymatic activity was afterwards calculated using the molar extinction coefficient of benzaldehyde ($\varepsilon_{280\ nm}$=1,376 liter $mmol^{-1}\ cm^{-1}$). One unit (U) of HNL activity is defined as the amount of enzyme that converts 1 µmol (R)-mandelonitrile per minute in the given buffer at 25° C.

To measure the HNL activity of insoluble protein aggregates, a modified endpoint-based mandelonitrile cleavage assay was used. Because of insoluble material all reaction tubes were kept under constant agitation (1,000 rpm) in a thermomixer (Eppendorf, Hamburg, Germany). For the assay the insoluble enzyme was suspended in 50 mM citrate phosphate buffer pH 5.5, diluted using assay buffer and incubated at 25° C. 100 µl of this solution was transferred to a new reaction tube containing 700 µl assay buffer and the reaction was immediately started by the addition of 200 µl substrate solution. After 2 min of reaction the tube was centrifuged (13,000 rpm, RT) for 1 min, resulting in a total reaction time of 3 min and 700 µl of the supernatant were immediately used for the absorbance measurement at 280 nm. This value corresponds to the amount of benzaldehyde released during the 3 min reaction time. To account for non-enzymatic mandelonitrile cleavage, the respective control in buffer (without enzyme) was subtracted from all measurements. Because mandelonitrile is already slowly cleaved in the substrate stock solution, this non-enzymatic cleavage had to be taken into account by measuring the time-resolved decay of substrate with the above mentioned assay. Moreover, to rule out measuring protein absorbance at 280 nm, additional controls had to be prepared with AtHNL-containing protein aggregates and substrate buffer (50 mM citrate phosphate buffer pH 3.5) instead of substrate stock solution. By combining all controls, the enzymatic activity could be calculated using the molar extinction coefficient of benzaldehyde. All measurements were performed at least in triplicate.

Different cell lysis fractions were tested for HNL activity using the mandelonitrile cleavage assay. The result is shown in FIG. 1. Surprisingly HNL activity was clearly detected in the insoluble fraction of the cells expressing TDoT-AtHNL. Although there was roughly 30% of the overall activity of the TDoT-AtHNL found in the soluble fraction, it was not possible to purify the fusion protein within the soluble fraction via immobilized metal ion affinity chromatography (data not shown).

Example 8: Determination of the pH-Spectrum of AtHNL-Containing Protein Aggregates To characterize the AtHNL-CatIBs we determined their relative initial rate activities over a broad spectrum of pH values and compared the results to the relative activities of the purified wild-type AtHNL.

Figure 2:
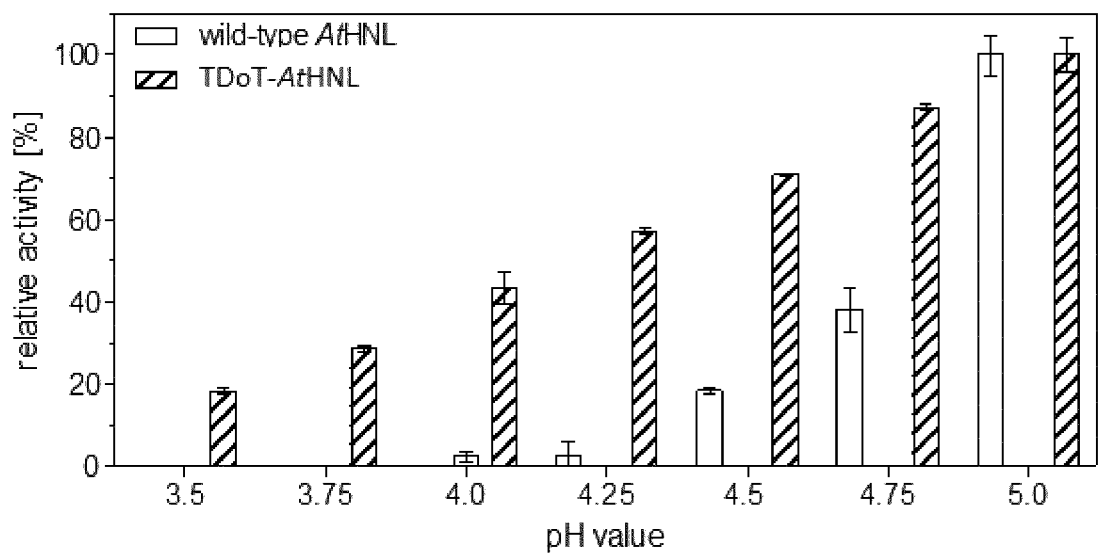
FIG. 2 displays the pH profile of HNL activity provided by wild-type AtHNL and TDoT-AtHNL. For the activity measurements, the enzyme/protein aggregates were incubated at 25° C. for 5 min. at the respective pH value before withdrawing a sample for the endpoint-based mandelonitrile cleavage assay. Error bars represent the standard deviation of the mean derived from three independent measurements.

The pH-dependent initial rate activities were determined using the endpoint-based mandelonitrile cleavage assay in the range from pH 3.5 to pH 5. For all measurements one stock of resuspended (50 mM citrate phosphate buffer pH 5.5) AtHNL-containing protein aggregates was prepared and adjusted by dilution with buffer until the absorption value at 280 nm after the incubation at pH 5 and the following reaction equaled 0.9. The AtHNL-containing protein aggregate stock was diluted at least 20-fold in 50 mM acetate buffer of the respective pH value and incubated for 5 min at 25° C. and 1000 rpm before withdrawing an aliquot for the activity assay. All measurements as well as controls without enzyme were performed in triplicate. The rate of the non-enzymatic reaction increased continuously with increasing pH values. The results of the pH profile of AtHNL activity and TDoT-AtHNL activity is displayed in FIG. 2.

As expected, the activity of both proteins was decreased at lower pH values. However, TDoT-AtHNL activity was still measurable at pH values, where the wild-type AtHNL had already lost nearly all activity. These results demonstrate a drastically increased resistance of enzymatic activity of HNL when present as fusion protein TDoT-AtHNL in protein aggregates at low pH values. Thus, providing HNL in form of a fusion protein comprising a coiled-coil domain within an insoluble protein aggregate extends the pH range for performing enzymatic reactions.

Example 9: Stability Investigations

AtHNL-containing protein aggregate solutions were prepared in a similar fashion to the already described determination of the pH spectrum. The only difference was that for every pH value a new AtHNL-containing protein aggregate stock solution was prepared and diluted with buffer (50 mM citrate phosphate buffer pH 5.5) until the absorption value at 280 nm after the incubation at the corresponding pH value and the following reaction equaled 0.7 to 0.9. For pH-dependent stability measurements the AtHNL-containing protein aggregate sample was diluted at least 20-fold in 50 mM acetate buffer adjusted to pH 3.5, pH 3.75, pH 4.0, pH 4.25 or pH 4.5, respectively. The samples were incubated up to 24 h at the respective pH, 25° C. and 1000 rpm. Aliquots were withdrawn from the incubated samples at defined intervals, and residual activity was measured using the mandelonitrile endpoint-based cleavage assay. All measurements were performed in triplicate. Half-lives ($t_{1/2}$) were derived from a single exponential fit of the experimental data.

Example 10: Treatment Protocol for Enhanced Activity of AtHNL-Catibs in Micro Aqueous Reaction Systems Before use in micro aqueous reaction systems 150 mg AtHNL-containing protein aggregates were sealed into an organic solvent-resistant, fine-woven nylon mesh (pore size 40 µm) and pretreated in several steps with $MgSO_4$ dried methyl tert-butyl ether (MTBE). The protocol consists of 30 min in 20 ml MTBE followed by three times 10 min in 10 ml MTBE, 20 min in 20 ml buffer (50 mM citrate phosphate buffer, pH 5.5) and 10 min in 10 ml MTBE. All incubations were performed in tightly shut glass vessels at room temperature under slow stirring. Between all steps the content of the nylon mesh was air dried and crushed to get a bigger surface area. After treatment the AtHNL-containing protein aggregates were either applied directly without the nylon mesh in the synthesis of (R)-mandelonitrile or with the nylon mesh still intact in a recycling experiment.

After purification, as a first step of characterization, the specific activity of the AtHNL-containing protein aggregates was determined. In order to take the different molecular weight of the tested enzymes into account the turnover number $k_{cat}$ was calculated, resulting in kcat values of 4.3±0.2 $s^{-1}$ for AtHNL-containing protein aggregates and 38.6±0.6 $5^{-1}$ for the wild-type purified AtHNL. With approximately 11% of the $k_{cat}$ of the purified AtHNL, the activity of the AtHNL-containing protein aggregates is decreased compared to the isolated soluble wild-type enzyme. A possible reason for the decreased activity could be that apart from folded, active protein, the protein aggregates contain a large fraction of misfolded and hence inactive protein. However, a lower purity of the AtHNL-containing protein aggregates preparation as well as diffusional limitation due to the insoluble nature of the protein aggregate particles might contribute to the observed reduced activity i.e. by limiting the access of the substrates to the enzyme active site.

The outlined possible role of diffusional limitation on the observed activity of AtHNL-CatIBs was further supported by experiments were we used wet and lyophilized AtHNL-containing protein aggregates for the synthesis of (R)-mandelonitrile in micro-aqueous methyl-tert butylether (MTBE).

Figure 3:
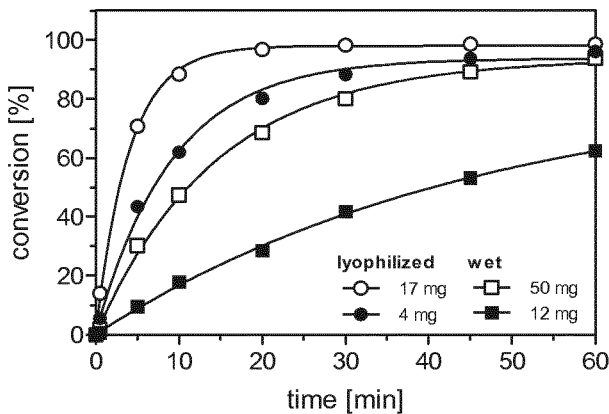
FIG. 3 illustrates the synthesis of (R)-mandelonitrile in a micro-aqueous reaction system with different amounts of lyophilized and wet protein aggregates comprising TDoT-AtHNL. The conversion and the enantiomeric excess (ee) of the product were determined by gas chromatography. Reaction conditions were 1 ml buffer-saturated MTBE (citrate phosphate buffer, pH 5.5) containing 2 M HCN, 500 mM benzaldehyde and 0.1 mM dodecane as internal standard. Temperature: 25° C.

We observed that lyophilized AtHNL-containing protein aggregates are more active than the directly employed wet preparation as can be seen in FIG. 3, because the latter might suffer from diffusional limitation due to internally contained buffer which represents a diffusion barrier for the hardly water-soluble substrate benzaldehyde. Moreover, when using lyophilized AtHNL-containing protein aggregates for the synthesis of (R)-Mandelonitrile, the enzyme amount needed for complete or near complete conversion within 60 min, can effectively be reduced to 4 mg (see FIG. 3). To achieve, the same conversion using the wild-type AtHNL approx. 2-6 mg of purified enzyme is needed. Despite AtHNL-containing protein aggregates show apparently a lower activity in the mandelonitrile cleavage assay than the purified wild-type AtHNL, they possess comparable activity in the industrially-relevant synthesis reaction. Thus, when employing catalytically active protein aggregates for biotransformation in aqueous and non-aqueous reaction systems, like for most enzyme immobilisates, diffusional limitation is a major issue.

Figure 8:
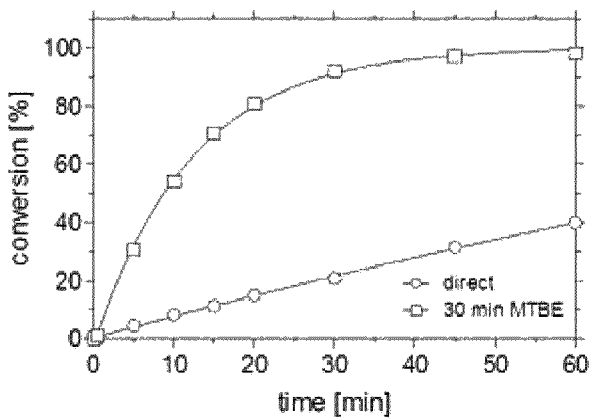
FIG. 8 shows the pretreatment of 3HAMP-AtHNL-containing protein aggregates with MTBE. Protein aggregates were either used directly after preparation in wet form or were pretreated with dry MTBE by washing with 20 ml MTBE for 30 minutes. Directly used protein aggregates displayed reduced activity (open circles) compared to MTBE-pretreated protein aggregates (open rectangles).
Figure 9:
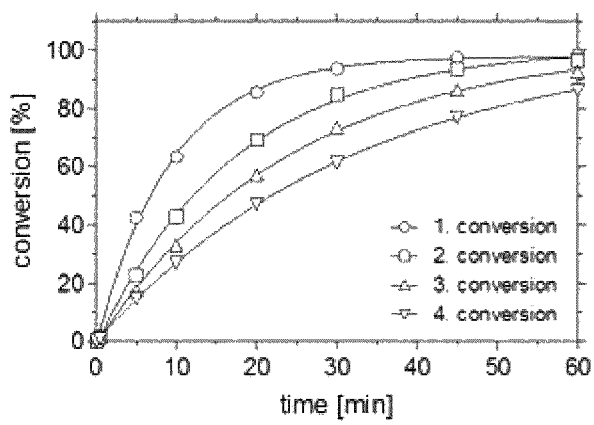
FIG. 9 displays recycling of pretreated 3HAMP-AtHNL-containing protein aggregates for the synthesis of (R)-mandelonitrile in a micro-aqueous reaction system. 150 mg MTBE-pretreated protein aggregates were used for the conversion of benzaldehyde and HCN to (R)-mandelonitrile in four consecutive reaction cycles. Between the reactions rounds, protein aggregates were washed for 5 minutes with 20 ml buffer-saturated MTBE. The conversion and the ee of the product were determined by GC. In all reactions the ee exceeded 99% (R). Reaction conditions: 1 ml buffer-saturated MTBE (citrate phosphate buffer pH 5.5) containing 2 M HCN, 500 mM benzaldehyde and 0.1 mM dodecane as internal standard; 150 mg pretreated 3HAMP-AtHNL-containing protein aggregates contained in a bag made of nylon membrane; 25° C.; 60 min.

3HAMP-AtHNL CatIB Show Catalytic Activity in an (R)-Mandelonitrile Synthesis Reaction 3HAMP-AtHNL-containing protein aggregates were employed as biocatalyst to convert benzaldehyde and HCN to (R)-mandelonitrile. As reaction system micro-aqueous methyl tert-butylether (MTBE) containing the two substrates was used. In order to decrease diffusional limitations, 150 mg 3HAMP-AtHNL-containing protein aggregates were pretreated for 30 minutes in 20 ml MTBE. This results in removal of water from the wet protein aggregate preparation and hence increases the substrate access to the biocatalyst resulting in increased turnover (FIG. 8). In subsequent recycling reactions MTBE-pretreated AtHNL-containing protein aggregates converted the substrates benzaldehyde and HCN to (R)-mandelonitrile with an excellent ee of >99% to the (R) product. Over four consecutive reaction rounds the final conversion decreased from 100% (1. conversion) to approximately 85% (4. Conversion), while the ee was virtually unaffected, i.e. exceeding 99% in all reactions (FIG. 9).

3HAMP-AtHNL-containing protein aggregates show HNL activity in a micro-aqueous reaction system, thus verifying the induction of catalytically-active inclusion body formation by fusion of the 3HAMP coiled-coil domain.

In order to verify that formation of catalytically active protein aggregates is not only induced by fusion of the TDoT-tag via a flexible poly-GGGS-Linker polypeptide, formation of protein aggregates was investigated using a fusion construct that lacks the GGGSGGGSGGGSGS amino acid linker which connects the TDoT-domain and the AtHNL open reading frame (TDoT-AtHNL-ΔL). The gene fusion was expressed in *E. coli* BL21 (DE3) in an identical manner as described for the GGGS-Linker containing construct (TDoT-AtHNL).

Figure 10:
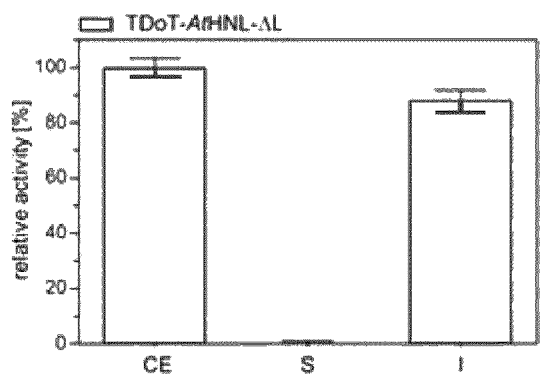
FIG. 10 illustrates the formation of TDoT-AtHNL-ΔL-containing protein aggregates, wherein the fusion protein comprises a five amino acid linker between the coiled-coil domain and the HNL-domain. After overexpression of the corresponding fusion gene, E. coli BL21 (DE3) cells were disrupted and the resulting crude cell extract (CE) was fractionated by centrifugation to obtain the soluble (S) fraction and the insoluble (I) fraction. The relative HNL activity was measured in the respective fractions at pH 5.5 with mandelonitrile end concentration of 13.4 mM. For activity measurements, the mandelonitrile cleavage assay was conducted in a discontinuous manner.

Cells were lysed and separated into the soluble and insoluble protein fraction by centrifugation as described for TDoT-AtHNL producing cells. HNL-activity tests for the crude whole-cell extract (CE), the soluble protein fraction (S) as well as the insoluble inclusion body fraction (I) revealed near complete insoluble expression of TDoT-AtHNL-ΔL as can be inferred from FIG. 10.

AtHNL activity could only be detected in the insoluble fraction, highlighting the fact, that Protein aggregate formation occurs independent of the presence of a flexible linker polypeptide.

Example 11: AtHNL-Containing Protein Aggregate-Catalyzed Synthesis of (R)-Mandelonitrile and Derivatives The general reaction setup for (R)-mandelonitrile synthesis has been described previously. In brief, 150 mg (wet weight) of pretreated AtHNL-containing protein aggregates was placed in a glass reaction vessel and the reaction was started immediately by addition of 1 ml of a 1.5-2 M HCN solution dissolved in MTBE, 0.5 mmol benzaldehyde and 0.1 mmol dodecane as an internal standard. All reactions were carried out at 25° C. in an air-tight vessel under argon atmosphere and the reaction mixture was constantly mixed using a magnetic stirrer. At defined time intervals 20 µl samples were withdrawn and (R)-mandelonitrile synthesis was monitored over 60 min by chiral GC (For details see section GC and HPLC sample preparation and analysis). For the determination of the substrate spectrum in addition to benzaldehyde, 2-chlorobenzaldehyde, 2-furaldehyde and hexanal were tested.

Example 12: Recycling of AtHNL-Containing Protein Aggregates for the Synthesis of (R)-Mandelonitrile For the recycling 150 mg pretreated AtHNL-containing protein aggregates still sealed into the nylon mesh (pore size 40 µm) to allow easy removal from the reaction medium were used. Four consecutive (R)-mandelonitrile syntheses were performed followed by storage overnight in buffer (50 mM citrate phosphate buffer, pH 5.5), 10 min incubation in 10 ml $MgSO_4$ dried MTBE and a final synthesis reaction. Between each reaction cycle the nylon mesh containing the AtHNL-containing protein aggregates was washed with 1 ml of dry MTBE to remove remaining product.

Figure 4:
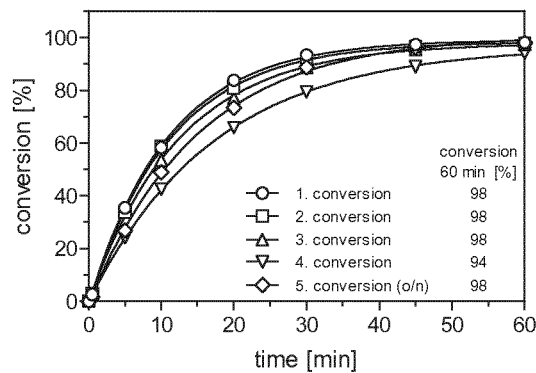
FIG. 4 illustrates the activity of recycled protein aggregates comprising a fusion protein comprising the coiled-coil domain TDoT and the catalytic domain AtHNL, i.e. TDoT-AtHNL. Complete progress of the conversion of benzaldehyde to (R)-mandelonitrile in five consecutive reaction cycles is displayed. After the fourth cycle, TDoT-AtHNL-containing protein aggregates were stored overnight in buffer and used for the fifth cycle after a short treatment with MTBE. Conversion and ee of the product were determined by gas chromatography. In all reactions, the ee exceeded 98% (R). Reaction conditions: 1 ml buffer-saturated MTBE (citrate phosphate buffer, pH 5.5) containing 2 M HCN, 500 mM benzaldehyde and 0.1 mM dodecane as internal standard; 150 mg pretreated protein aggregates containing TDoT-AtHNL in a sachet made of a nylon membrane; temperature: 25° C.; duration: 60 min.

We established a solvent pretreatment protocol to reduce the water content of wet AtHNL-containing protein aggregates and thus increase their surface, while at the same time retain a bigger particle size for secure containment of the protein aggregates in a nylon mesh. This allows easy removal from the reaction and washing without greater loss of AtHNL-containing protein aggregates. In brief, AtHNL-containing protein aggregates are washed several times with MTBE, which results in an observable shrinking and drying of the protein aggregate particles inside the tea bag. Using this pretreatment protocol, the turnover is drastically increased, suggesting that diffusional limitation is major issue. After the solvent pretreatment the nylon tea bag with the AtHNL-containing protein aggregates was applied in four consecutive (R)-mandelonitrile synthesis reactions with washing steps in between. During these reactions the activity of the AtHNL-containing protein aggregates diminished slightly and even after the fourth application a conversion of 94% with an enantiomeric excess (ee) of 98.5% (R) could be achieved (FIG. 4). After the fourth conversion the AtHNL-containing protein aggregates were stored overnight in buffer, treated shortly with solvent again and were applied a fifth time in a synthesis reaction. With this procedure the activity was higher than in the fourth reaction and resulted in 98% conversion with an ee of 98.5%. This observation has several possible explanations. One would be that a fraction of the AtHNL-containing protein aggregates gets inactivated during the first four rounds of recycling, but this inactivation is reversible in water. Another possibility could be that water content is responsible for this behavior. During the first four recycling reactions and solvent washing steps water might be removed from the AtHNL-containing protein aggregates which leads to reduced activity. Storage in buffer then resupplied a certain amount of water to the protein aggregates, which restored activity.

Example 13: MenD Activity

After cell disruption and fractionation of MenD-containing protein aggregates and control MenD producing cells the activities in the crude cell extract, supernatant and the resuspended insoluble protein fraction were assayed, respectively. Therefore protein concentration in the crude cell extract was determined via a Bradford method which can measure concentrations of soluble as well as insoluble protein. For the activity measurement in the crude cell extracts a final protein concentration of 2.8 mg ml$^{-1}$ MenD-containing protein aggregate and 0.3 mg ml$^{-1}$ MenD control was used, while corresponding volumes of the supernatant (soluble protein) and resuspended protein aggregate fractions were applied. The reaction was performed in glass vials with a size of 1.5 ml containing 50 mM TEA pH 8, 2 mM MgSO$_4$, 0.1 mM ThDP, 60 mM α-ketoglutarate and 20 mM benzaldehyde in a final volume of 600 µl for 3 h at 25° C. and 800 rpm in an Eppendorf thermomixer (Hamburg, Germany). Subsequent the samples were prepared for GC analysis (see section GC and HPLC sample preparation and analysis). All measurements were performed in triplicates, from which the standard deviations were derived.

For investigating the influence of the TDoT domain on the soluble/insoluble production of proteins of different complexity, we chose the 2-succinyl-5-enolpyruvyl-6-hydroxy-3-cyclohexene-1-carboxylate synthase (Men D) from *E. coli* as basis for another catalytic domain in fusion protein comprising a coiled-coil domain and a catalytic domain.

Figure 5:
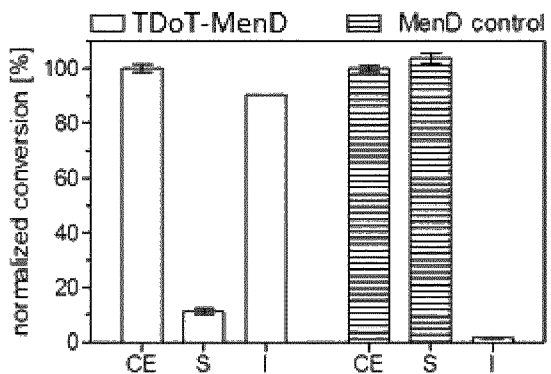
FIG. 5 shows a graph illustrating the activity of protein aggregates comprising a fusion protein comprising the coiled-coil domain TDoT and the catalytic domain MenD, i.e. TDoT-MenD. Activity of the fractions of TDoT-MenD-containing protein aggregates and MenD control producing cells are displayed. S and I volumes of the soluble fraction (S) and the insoluble fraction (I) correspond to the applied volume of the crude cell lysate (CE) (final protein concentrations in reaction with CE: 2.8 mg ml$^{-1}$ TDoT-MenD protein aggregates, 0.3 mg ml$^{-1}$ MenD control) were used. Reaction conditions: 50 mM TEA pH 8, 2 mM MgSO$_4$, 0.1 mM ThDP, 60 mM α-KG, 20 mM benzaldehyde, 3 h at 25° C. and 800 rpm. The conversion was determined by GC based on benzaldehyde consumption. The MenD activity determined for the CE fraction was defined as 100%. Error bars represent the standard deviation of the mean derived from three independent measurements.

Gene fusions coding for TDoT-Linker-MenD were generated by replacing the AtHNL encoding fragment of TDoT-Linker-AtHNL with the respective gene coding for MenD. The fusion proteins were produced in *E. coli* BL21 (DE3), cells were disrupted and treated identical to the preparation of AtHNL-containing protein aggregates. Crude cell extract, the soluble fraction as well as the insoluble fraction were analyzed by activity tests which were carried out to address the distribution of active/fluorescent protein. The results were comparable to those obtained for AtHNL-containing protein aggregates. The TDoT-MenD fusion protein was produced in very high yields in insoluble form, whereas the controls without the TDoT domain were completely soluble (FIG. 5). Without the TDoT tag nearly 100% of the activity was found in the soluble protein fraction. By fusing the coiled-coil domain the activity of MenD shifts to 90% to the insoluble fraction. These results clearly demonstrate that fusion of the TDoT tag leads to high-level protein aggregate formation. Moreover, the effect appears independent of the complexity of the target protein. Even cofactor binding inside the protein aggregates is no obstacle and does not impair the function of the biocatalyst. Furthermore, the results regarding the MenD-containing protein aggregates are suggesting that at least two MenD domains have the right arrangement to each other. Therefore, the MenD is able to adopt its correct biocatalytically active quaternary structure in the protein aggregates, because MenD is an enzyme of high complexity, being tetrameric and only active if it is at least a dimer due to the necessary cofactor thiamine diphosphate (ThDP) which binds at the interface between two monomers. The results with the TDoT-MenD fusion protein demonstrate that the TDoT tag is working with more complex biocatalysts.

Example 14: MenD-Containing Protein Aggregates Recycling

As another application example for protein aggregates, we analyzed the recyclability of MenD-containing protein aggregates for the production of functionalized α-hydroxy ketones. Therefore, the model substrates benzaldehyde and α-ketoglutarate (α-KG) were applied and the reaction was performed in a buffered system in reaction tubes which allowed for easy separation of the reaction medium and recovery of the MenD-containing protein aggregates via centrifugation.

The MenD-containing protein aggregate recycling setup is very similar to the determination of MenD activity described above. All buffers and substrate concentrations hold true for this experiment. To ensure full consumption of 20 mM benzaldehyde with 18 mg ml$^{-1}$ MenD-containing protein aggregates (wet weight) several reactions and blanks (in 1.5 ml Eppendorf tubes because centrifugation of the whole reaction is necessary for the recycling) were started (25° C., 800 rpm, Eppendorf thermomixer (Hamburg, Germany)) at the same time but triplicates were stopped by centrifugation (14,000 rpm, 5 min, 4° C.) after different time intervals (5 min, 60 min, 120 min, 240 min and 360 min) and samples of the supernatant were prepared for GC and HPLC measurements (see section GC and HPLC sample preparation and analysis). Blank reactions for every interval were used as reference for non-enzymatic benzaldehyde consumption. The resulting pelleted MenD-containing protein aggregates were separated from the supernatants, washed once with 200 µl MenD buffer, centrifuged (14,000 rpm, 5 min, 4° C.) and stored at −20° C. after removing the supernatant. Because after 360 min nearly all benzaldehyde was consumed this time was chosen for the recycling experiment. After this was determined the pelleted and frozen MenD-containing protein aggregates from the previous day were resuspended in 100 µl MenD buffer, used for a new reaction (360 min, 25° C., 800 rpm), pelleted, washed and frozen again at −20° C. until the next day and the next step of recycling. In total eight subsequent reactions were performed in this manner.

Figure 6:
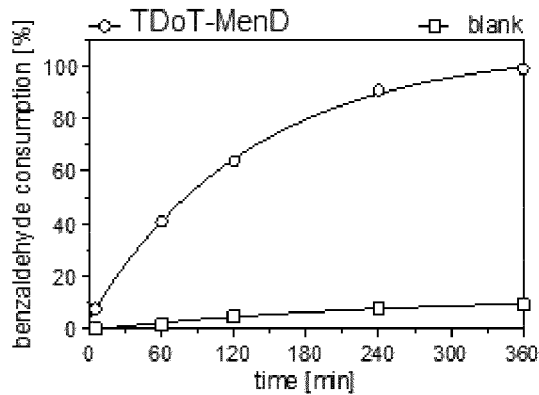
FIG. 6 shows the recycling of TDoT-MenD-containing protein aggregates in an aqueous reaction system. Displayed is the time-resolved production of 5-hydroxy-4-oxo-5-pentanoate followed via the consumption of benzaldehyde in the first recycling reaction.
Figure 7:
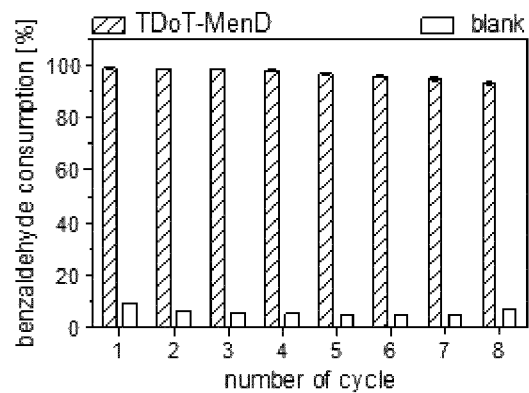
FIG. 7 displays recycling of TDoT-MenD-containing protein aggregates. The results of eight consecutive reaction cycles are shown with benzaldehyde consumption after six hours. Between cycles the TDoT-MenD-containing protein aggregates were separated by centrifugation, washed in buffer, pelleted and frozen at −20° C. until next use. The consumption of benzaldehyde was determined by GC and the ee of the product via chiral-phase HPLC. In all cases the ee exceeded 99% (R). The experiment was performed in triplicate and the derived standard deviations are well below 5%. Reaction conditions: 18 mg ml$^{-1}$ TDoT-MenD-containing protein aggregates (wet weight), 50 mM TEA pH 8, 2 mM MgSO$_4$, 0.1 mM ThDP, 60 mM α-KG, 20 mM benzaldehyde, 6 h at 25° C. and 800 rpm.

The first reaction was set up in a manner, that a time-resolved analysis of the benzaldehyde consumption was possible (FIG. 6). After six hours of incubation 99% of the benzaldehyde was consumed and the recovered MenD-containing protein aggregates were stored at −20° C. until next use. For the following seven reaction rounds only the benzaldehyde consumption after six hours was measured. After eight recycling rounds, MenD-containing protein aggregates still exhibited an outstanding performance with 95% benzaldehyde consumption (FIG. 7). The marginal loss of 4% activity after eight rounds of recycling is not necessarily connected to inactivation of the protein aggregates, but could be the result of catalyst loss during removal of supernatants or the washing step between recyclings. In addition to the measurement of benzaldehyde consumption, the product ee for every reaction was determined by chiral-phase HPLC which was in all cases excellent yielding >99% (R) product.

Example 15: MenD-CatIBs Substrate Spectrum

For the determination of a MenD-CatIB substrate spectrum benzaldehyde and four other derivates thereof were tested (2-fluorobenzaldehyde, 2-chlorobenzaldehyde, 2-bromobenzaldehyde and 2-methoxybenzaldehyde). Therefore 600 µl reactions were set up in tightly shut glass vials with a final concentration of 18 mg ml$^{-1}$ wet weight MenD-CatIBs, 20 mM aldehydes and 60 mM α-ketoglutarate (for buffers see section MenD activity). The mixture was incubated for 24 h at 25° C. and 800 rpm in an Eppendorf thermomixer. Subsequently, the aldehyde consumption was analyzed by GC and the enantiomeric excess via HPLC (see section GC and HPLC sample preparation and analysis).

Example 16: GC and HPLC Sample Preparation and Analysis

From synthesis in micro aqueous systems with AtHNL-CatIBS 20 µl samples were taken and mixed with 1.5 ml dichloromethane, 40 µl pyridine and 40 µl ethyl acetate. The latter two components are for derivatization of the reaction products, which leads to more volatile compounds that can be separated in (R) and (S) enantiomers. This was realized on an Agilent 6890N Network GC system with a flame ionization detector (Agilent Technologies, USA) equipped with a CP-Chirasil-Dex CB column (25 m×0.25 mm×0.25 µm, Varian, Germany) and hydrogen as carrier gas.

All samples of MenD catalyzed reactions were centrifuged (14,000 rpm, 5 min, 4° C.) before use. For GC sample preparation 200 µl reaction supernatant were mixed with 300 µl ethylacetate (containing dodecane as standard) and shaken thoroughly for extraction of remaining benzaldehyde. After centrifugation (14000 rpm, 1 min, 4° C.) 200 µl (4 µl injection) of the upper organic phase were used for analysis on GC system (specifics described above). The injection temperature was set to 150° C., 160° C. and 170° C. for benzaldehyde, halosubstituted benzaldehydes and for 2-methoxybenzaldehyde respectively. This was followed by an isotherm run for 8 min. As means of activity the consumption of benzaldehyde and derivatives thereof was calculated based on blank reactions as references with buffer instead of protein, which were mixed and directly used for extraction of benzaldehyde followed by GC analysis.

The enantiomeric excesses (ee) of the produced 5-hydroxy-4-oxo-5-arylpentanoates were determined by chiral phase HPLC. Therefore 200 µl of the reaction supernatant were mixed with 200 µl MTBE and 20 µl 10% (v/v) perchloric acid and shaken thoroughly to extract the reaction product. The acid is necessary for solubility of the product in organic solvents. From the upper organic phase 200 µl (10 µl injection) were analyzed by chiral HPLC on a 1260 Infinity chromatography system (Agilent Technologies, USA) equipped with a Diacel Chiralcel OD-H column (5 µm×250 mm×4.6 mm). All products were detected at 210 nm using n-hexane:2-propanol mixtures with 0.25% TFA and a flow rate of 1.2 ml ml$^{-1}$ at 20° C.

Benzaldehyde: 92:8
Substituted benzaldehydes: 90:10

Retention times under these conditions for the different compounds were described recently.

Example 17: Lipase A Activity

Lipolytic activity was determined by using p-nitrophenol butyrate (pNPB) as artificial lipase substrate. This assay is based on hydrolytic cleavage of the colorless p-NPB, wherein lipase activity hydrolyses the ester bound and releases the colored para-nitrophenolate (p-NP). Para-nitrophenolate possesses an extended 7-electron system and absorbs light at a wavelength of 410 nm such that the reaction can be measured photometrically by an increase of absorption or quantitatively.

Figure 11:
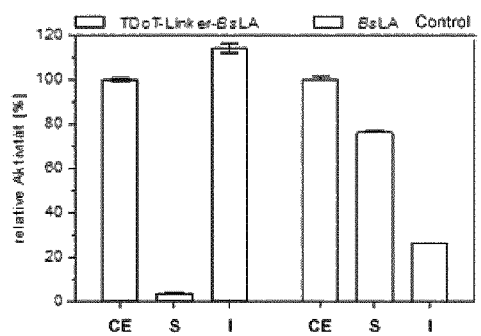
FIG. 11 shows the formation of TDoT-BsLA-containing protein aggregates, wherein the fusion protein comprises a poly-GGGS linker between the coiled-coil domain and the BsLA-domain. After overexpression of the corresponding fusion gene, E. coli BL21 (DE3) cells were disrupted and the resulting crude cell extract (CE) was fractionated by centrifugation to obtain the soluble (S) fraction and the insoluble (I) fraction. Lipase activity was measured colometrically using para-nitrophenolbutyrate as substrate in that the increase of absorption at 410 nm was measured. The buffer, substrate stock and photometer were prewarmed to 25° C. and the increase of absorption at 410 nm was tracked for a minute. Reference probes were cell extracts of the bacterial host cells expressing the tested constructs and diluted with cell lysis buffer such that an absorption of 0.9 at 410 nm was achieved after 1 minute. The samples of the soluble and insoluble protein factions were diluted similarly and their activity was measured. The obtained values were normalized to the activity of the corresponding total cell lysate. All measurements were performed in triplicate.

Bacterial host cells expressing TDoT-LinkerBsLA fusion proteins were lysed and the resulting crude cell extract as well as the soluble and insoluble fraction obtained after centrifugation were analysed for lipase activity. The result is shown in FIG. 11. It can be seen that the lipase activity is almost exclusively found in the insoluble fraction.

In an additional experiment, protein aggregates comprising one of the fusion proteins TdoT-BsLA, 3HAMP-BsLA, GCN4-p1-BsLA and GCN4-pLI-BsLA were resuspended in 50 mM sodium phosphate buffer (pH 8.0) (1% (w/v)). 10 µl of this suspension were pipetted to the well of a microtiter plate (MTP) and the reaction was started by addition of 5 µl pNPB (dissolved in acetonitrile) yielding a final assay concentration of 0.8 mM pNPB. All reactions were carried out in triplicate. The MTP was incubated at room temperature for 10 minutes. For documentation the MTP was photographed.

Optical analysis of the photos revealed that all coiled-coil BsLA fusion proteins show lipolytic activity. TDoT-BsLA, 3HAMP-BsLA, GCN4-p1-BsLA and GCN4-pLI-BsLA show similar lipolytic activity, thus verifying the induction of catalytically-active protein aggregate formation by fused coiled-coil domains of different complexity.

Example 18: BtADH; Alcohol Dehydrogenase (ADH) from *Bacillus thuringiensis*

Methods
Plasmid: pTDoT
Assay:
100 mM Kpi-buffer pH 7.0
5 mg GDH060
50 mM Glucose
10 mM trans-2-Hexenal
0.2 mM NAD
10% enzyme (soluble and insoluble fraction after cell disruption)
Mix at 25° C. and 1000 rpm
Sampling (10 min, 60 min, overnight): 100 µl Sample was extracted with 150 µl MTBE (Methyl tert-butyl ether)
GC-Analysis:
Column: FS-INNOPEG-2000, CS-Chromatographie Service

| GC-programm: | 60° C. | |
|---|---|---|
| | 11° C./min | 115° C. |
| | 33° C./min | 260° C. |

BtADH Activity

After cell disruption and fractionation of BtADH-containing protein aggregates and control BtADH producing cells the activities in the crude cell extract, supernatant and the resuspended insoluble protein fraction were assayed, respectively. For the activity measurement in the crude cell extracts 10 µl BtADH-containing protein aggregate and 10 µl BtADH control was used, while corresponding volumes of the supernatant (soluble protein) and resuspended protein aggregate fractions were applied. The reaction was performed in glass vials containing 100 mM KPi-buffer pH 7, 1 M Glucose, 0.2 mM NAD, 10 mM trans-2-Hexenal and 5 mg GDH 060 (supplied from evocatal for cofactor regeneration) in a final volume of 1000 µl at 25° C. and 1000 rpm in an Eppendorf thermomixer (Hamburg, Germany). Subsequently the samples were prepared for GC analysis (see section GC and HPLC sample preparation and analysis).

For investigating the influence of the TDoT domain on the soluble/insoluble production of proteins of different complexity, we chose the Alcohol Dehydrogenase (BtADH) from *Bacillus thuringiensis* as a basis for another catalytic domain in fusion protein comprising a coiled-coil domain and a catalytic domain.

Gene fusions coding for TDoT-Linker-BtADH were generated by replacing the AtHNL encoding fragment of TDoT-Linker-AtHNL with the respective gene coding for BtADH. The resulting fusion protein is set forth in SEQ ID NO: 76 and the fusion gene encoding this fusion protein is set forth in SEQ ID NO: 77.

The fusion proteins were produced in *E. coli* BL21 (DE3), cells were disrupted and treated identical to the preparation of AtHNL-containing protein aggregates.

Crude cell extract, the soluble fraction as well as the insoluble fraction were analyzed by activity tests which were carried out to address the distribution of active protein. The results were comparable to those obtained for AtHNL-containing protein aggregates.

The TDoT-BtADH fusion protein was produced in very high yields in insoluble form, whereas the controls without the TDoT domain were completely soluble. Without the TDoT tag nearly 100% of the activity was found in the soluble protein fraction. By fusing the coiled-coil domain the yield of BtADH shifts to >90% to the insoluble fraction. These results clearly demonstrate that fusion of the TDoT tag leads to high-level protein aggregate formation.

Moreover, the effect appears independent of the complexity of the target protein. Even cofactor binding inside the protein aggregates is no obstacle and does not impair the function of the biocatalyst. Furthermore, the results regarding the BtADH-containing protein aggregates are suggesting that at least two BtADH domains have the right arrangement to each other. It is assumed that the BtADH is able to adopt its correct biocatalytically active quaternary structure in the protein aggregates, because BtADH is an enzyme of high complexity, being potentially tetrameric and only active if it is at least a dimer due to the necessary cofactor zinc. The results with the TDoT-BtADH fusion protein demonstrate that the TDoT tag is working with more complex biocatalysts.

GC and HPLC Sample Preparation and Analysis

All samples of BtADH catalyzed reactions were centrifuged (14,000 rpm, 5 min, 4° C.) before use. For GC sample preparation 100 µl reaction supernatant were mixed with 150 µl MTBE and shaken thoroughly for extraction of remaining trans-2-Hexenal. After centrifugation (14000 rpm, 1 min, 4° C.) 200 µl (4 µl injection) of the upper organic phase were used for analysis on GC system (Column FS-INNOPEG-2000). The temperature program was set to 60-115° C. with an increase of 11° C. per min, followed by 115-260° C. with an increase of 33° C. per min.

Example 19: LCC—LC-Cutinase; Cutinase from Metagenomic Origin

Methods
Plasmid: pTDoT
Assay:

Lipolytic activity of LC-Cutinase (LCC) is determined by using p-nitrophenol palmitate (pNPP) as artificial lipase substrate. This assay is based on hydrolytic cleavage of the colorless p-NPP, wherein lipase activity hydrolyses the ester bound and releases the colored para-nitrophenolate (p-NP). Para-nitrophenolate possesses an extended 7-electron system and absorbs light at a wavelength of 410 nm such that the reaction can be measured photometrically by an increase of absorption or quantitatively.

Briefly, the assay will be carried out by mixing solution 1 and 2 with shaking. The enzyme solution will be added immediately and the absorption will be measured at 410 nm. The activity will be calculated due to the equation:

$$\frac{v_{max} * V_{total}}{\varepsilon * d * v}$$

$v_{max}$ = Slope mol/t; $V_{total}$ = whole volume;

$\varepsilon$ = molar extinction coefficient|* mol$^{-1}$* cm$^{-1}$~; $d$ = thickness;

$v$ = volume enzymatic solution

| Sörensen phosphate buffer: | |
|---|---|
| Solution A: | 50 mM Na$_2$HPO$_4$ × 2H$_2$O |
| Solution B: | 50 mM KH$_2$PO$_4$ |
| Mix solution A and B 17:1 (pH 8.0) | |
| Solution I: | 5 mM NaDOC (Natriumdesoxycholate) 1 mg/mL Gummi Arabicum in 180 ml Sörensen phosphate buffer |
| Solution II: | 8 mM para-Nitrophenylpalmitate in Isopropanol |

LCC Lipolytic Activity

Gene fusions coding for TDoT-Linker-LCC were generated by replacing the AtHNL encoding fragment of TDoT-Linker-/AtHNL with the respective gene coding for LCC. The resulting fusion protein is set forth in SEQ ID NO: 80 and the fusion gene encoding this fusion protein is set forth in SEQ ID NO: 81 Bacterial host cells expressing TDoT-LinkerLCC fusion proteins are lysed and the resulting crude cell extract as well as the soluble and insoluble fraction obtained after centrifugation is analysed for lipase activity.

Example 20

PfBAL—benzaldehyde lyase from *Pseudomonas fluorescens*, and
RADH—alcohol dehydrogenase of *Ralstonia* sp.

We have tested the feasibility of inducing CatIB formation for complex multimeric cofactor-dependent enzymes. As coiled-coil (CC) domains the TDoT-tag (SEQ ID NO: 1, [1]) as well as the 3HAMP domain (SEQ ID NO: 3, [2]) of the *Pseudomonas aeruginosa* Aer2 protein were selected as fusion partner for the benzaldehyde lyase from *Pseudomonas fluorescens* (PfBAL; SEQ ID NO: 82; EC 4.1.2.38) [3], and an alcohol dehydrogenase of *Ralstonia* sp. (RADH; SEQ ID NO: 86; EC 1.1.1.1) [4]. CCs were selected to display a variable degree of length and quaternary structural complexity. While the initially used TDoT-tag is a short tetrameric CC, the 172 amino acids long 3HAMP domain forms a complex dimeric CC.

Initially, TDoT-PfBAL and TDoT-RADH gene fusions were constructed following the previously described design principles [1]. All initial constructs consisted of the TDoT CC domain and the respective target protein linked by a (GGGS)$_3$ linker polypeptide. All gene fusions were constructed using pET28a as expression vector. The resulting fusion proteins were produced in *E. coli* BL21(DE3). While for TDoT-PfBAL large amounts of insoluble fusion protein (CatIBs) accumulated within the cell, the expression of the TDoT-RADH did result in the accumulation of active inclusion bodies, but in a smaller amount. We therefore altered the corresponding fusion constructs by utilizing the 3HAMP CC domain as fusion partner for RADH. The resulting 3HAMP-RADH construct showed improved formation of active inclusion bodies (CatIBs) compared to the initially tested TDoT-RADH construct. The present example thus details gene fusion design principles which can be used to optimize the production of active inclusion bodies (CatIBs).

Materials and Methods

Selection of CC Domains

CC domains were selected from the coiled-coil database CC+ http://coiledcoils.chm.bris.ac.uk/ccplus/search/periodic_table. As suitable CCs the initially described TDoT CC domain of the cell-surface protein Tetrabrachion from *Staphylothermus marinus* [6] and the larger dimeric 3HAMP CC domain of the *Pseudomonas aeruginosa* Aer2 protein (residues 1 to 172) [2] were selected.

Construction of the TDoT-PfBAL and 3HAMP-RADH Expression Plasmids

The gene coding for the TDoT-tag and the 3HAMP-tag, containing a 3'-linker region (coding for a 3-fold GGGS repeat (designated in the following as (GGGS)$_3$), a protease Factor Xa recognition site (amino acid sequence: IEGR) and the necessary restriction sites for cloning were synthesized by Eurofins Genomics (Ebersberg, Germany) and supplied on a plasmid (pEX-A-TDoT-Linker and pEX-A-3HAMP-Linker, respectively). The basic expression vector containing the inclusion body formation inducing TDoT-tag and 3HAMP-tag including the C-terminal linker region was sub-cloned from pEX-A-TDoT-Linker and pEX-A-3HAMP-Linker into pET28a using the restriction endonucleases NdeI and BamHI resulting in pHis-TDoT-Linker and pHis-3HAMP-Linker, respectively. This results in the in-frame fusion of a 20 amino acids long N-terminal His-tag, which is encoded on the pET28a plasmid. To remove the His-tag, the corresponding pHis-TDoT-Linker and pHis-3HAMP-Linker plasmids were digested with XbaI and NdeI. This results in the release of a 99 bp DNA fragment encoding the N-terminal His-tag and ribosome binding site (RBS). A double stranded DNA segment containing only the RBS as well as a short upstream DNA sequence was assembled from two oligonucleotides (RBS_Oligo_fw; RBS_Oligo_rev). The corresponding oligonucleotides contained a 5'-XbaI and 3'-NdeI site which facilitates the cloning into the XbaI and NdeI hydrolyzed pHis-TDoT-Linker and pHis-3HAMP-Linker. This yields the two plasmids pTDoT-Linker and p3HAMP-Linker, which were used for all subsequent cloning steps.

The genes coding for the target enzymes were amplified via standard PCR methods using the oligonucleotide primers listed in Table 1 containing BamHI and SalI, restriction sites for RADH (BamHI_RADH_fw; RADH_SalI_rev). The PfBAL encoding gene was amplified containing 5'- and 3'-restriction endonuclease recognition sites for BamHI and NotI (BamH_BAL_fw; BAL_NotI_rev). The resulting PCR products were hydrolyzed with the respective restriction enzymes and ligated into the similarly digested TDoT-Linker and 3HAMP-Linker plasmids, yielding pTDoT-PfBAL, pTDoT-RADH, and p3HAMP-RADH. All sequences were verified by sequencing (Seqlab GmbH, Göttingen, Germany).

The DNA and amino acid sequences of all gene fusions used in this study are summarized in the Supplementary Material In the attached sequence listing, the fusion protein TDoT-PfBAL is set forth in SEQ ID NO: 84 and the fusion gene encoding this fusion protein is set forth in SEQ ID NO: 85.

In the attached sequence listing, the fusion protein TDoT-RADH is set forth in SEQ ID NO: 88 and the fusion gene encoding this fusion protein is set forth in SEQ ID NO: 89.

In the attached sequence listing, the fusion protein 3HAMP-RADH is set forth in SEQ ID NO. 90 and the fusion gene encoding this fusion protein is set forth in SEQ ID NO: 91.

TABLE 5

Oligonucleotides used for amplification of the RADH and PBAL encoding gene fragments

| Name | sequence (5' → 3') | SEQ ID No. | $T_m$ [° C.] |
|---|---|---|---|
| BamHI_RADH_fw | ATA TAT GGA TCC ATG TAT CGT CTG CTG AAT AAA ACC GC | 92 | 61.8 |
| RADH_SalI_rev | ATA TAT GTC GAC TTA AAC CTG GGT CAG ACC ACC ATC | 93 | 65.6 |
| BamH_BAL_fw | ATA TAT GGA TCC ATG GCG ATG ATT ACA GGC GGC GAA C | 94 | 65.6 |
| BAL_NotI_rev | ATA TAT GCG GCC GCT TAT GCG AAG GGG TCC ATG | 95 | 67.0 |
| NdeI_TDoT_fw | ATA TAT CAT ATG ATC ATT AAC GAA ACT GCC GAT GAC | 96 | 58.2 |
| TDoT_BamHI_rev | TAT ATA GGA TCC AAT GCT CGC GAG AAT GGT G | 97 | 60.9 |
| RBS_Oligo_fw | CTAGAAATAATTTGTTTAACTTTAAGAA GGAGATATACA | 98 | 55.0 |
| RBS_Oligo_rev | TATGTATATCTCCTTCTTAAAGTTAAACA AAATTATTT | 99 | 53.6 |

Heterologous Production of TDoT-PfBAL, TDot-RADH, and 3HAMP-RADH

All gene fusions were expressed under identical conditions. In brief, lysogeny broth (LB) medium (25 mL in a 250 mL Erlenmeyer shake flask) was inoculated with an *E. coli* BL21(DE3) clone containing the respective target plasmid from a fresh transformation plate (LB agar). This pre-culture was grown overnight at 37° C. with constant agitation at 130 rpm. With this culture, the main expression culture (500 mL autoinduction medium in a 5 L shake flask, or 100 mL autoinduction medium in a 1 L shake) was inoculated to an OD600 of 0.05. The employed autoinduction medium consisted of premixed terrific broth (TB) medium (Roth, Karlsruhe, Germany) supplemented with 0.4% (v/v) glycerol and glucose (0.5 g L-1) to suppress gene expression in the first hours of incubation, and lactose (2 g L-1) for the induction of expression in a later phase. All media were supplemented with kanamycin (50 μg mL-1) for plasmid maintenance. Cultivation was performed for 3 h at 37° C. and 130 rpm, followed by a prolonged incubation for another 69 h at 15° C. and 130 rpm. After the cultivation, the cells were harvested by centrifugation and were directly used for cell disruption and purification or stored at −20° C. All control constructs (lacking the fused CC domain) were produced in an identical manner as described for the corresponding CC fusion proteins.

Cell Disruption

All cell pellets were resuspended in lysis buffer (50 mM sodium phosphate buffer, 100 mM sodium chloride, pH 8.0) to obtain a 10% (w/v) suspension. Cell lysis was carried using an Emulsiflex-05 high-pressure homogenizer (AVESTIN Europe GmbH, Mannheim, D) at a constant pressure of 1000-1500 bar by passing the cell suspensions three times through the homogenizer.

Fractionation of Crude Cell Extracts and Inclusion Body Purification

After cell disruption the insoluble inclusion bodies containing pellet and the soluble protein containing supernatant were separated by centrifugation (15000 g, 30 min, 4° C.). The resulting pellet was washed twice with milliQ water. The resulting (Cat)IBs were subsequently lyophilized for 48-72 h.

PfBAL Activity Assay

All measurements were performed using a Flourog3-22 spectrofluorimeter (Horiba Jobin Yvon, Bensheim, D). The activity of PfBAL was measured using dimethoxybenzaldehyde (DMBA) as substrate [7]. PfBAL catalyzes the the coupling of two DMBA molecules to 1,2-bis(3,5-dimethoxyphenyl)-2-hydroxyethanone (TMBZ). The below reaction shows the assay principle for the measurement of PfBAL activity. PfBAL catalyzes a C—C-coupling of two dimethoxybenzaldehyde molecules (DMBA) to yield 1,2-bis(3,5-dimethoxyphenyl)-2-hydroxyethanon (TMBZ). For conversion, the enzyme utilizes the cofactors thiamine diphosphate (ThDP) and magnesium ions (Mg2+). The decrease of DMBA can be measured fluorometrically by exciting DMBA at 350 nm and recording the fluorescence emission at 460 nm.

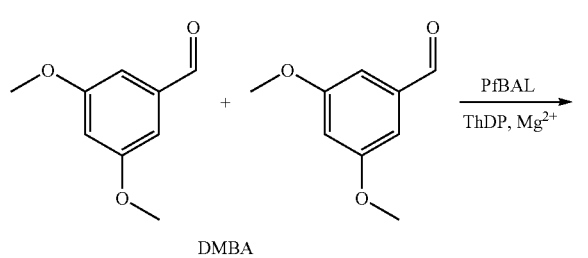

DMBA

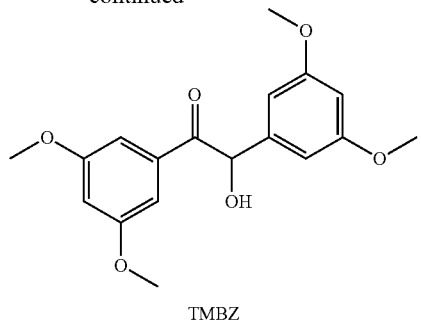

TMBZ

The conversion of DMBA can be measured fluorometrically by following the decrease in fluorescence emission due to depletion of DMBA. The assay was performed in semi-micro quartz cuvettes at 25° C. using TEA buffer (50 mM triethanolamine, pH 8.0) in a volume of 1 mL containing 0.5 mM thiamine diphosphate, 2.5 mM magnesium sulfate, 3 mM DMBA and 200 μl TDoT-PfBAL suspensions in suitable dilutions. The conversion was monitored continuously for 90 s by using an excitation wavelength of 350 nm and an emission wavelength of 460 nm (2.6 nm excitation and emission bandwidth). To minimize light scattering due to turbid CatIB suspensions, fluorescence emission was detected at a 22.5° front-face angle. All reactions were measured at least in triplicate, the background was subtracted by monitoring a blank reaction without enzyme. Conversion of DMBA by TDoT-PfBAL was quantified employing a calibration curve for DMBA. To obtain the activity distribution shown in FIG. 12, PfBAL activity was measured in the crude cell extract (set to 100%) as well as in the pellet and supernatant after centrifugation. To remove residual supernatant the pellet was washed once with purified water before the activity measurement. PfBAL activity in pellet (CatIBs) and supernatant (soluble protein) was expressed relative to the activity of the crude cell extract.

RADH Activity Assay

All measurements were performed using a Fluorolog3-22 spectrofluorimeter (Horiba Jobin Yvon, Bensheim, D). The activity of RADH was determined fluorometrically by detecting the consumption of NADPH due to the conversion of benzaldehyde to phenylmethanol catalyzed by RADH. The below reaction shows the assay principle for the measurement of RADH activity. RADH catalyzes the reduction of benzaldehyde to phenylmethanol using NADPH as cofactor. The corresponding consumption of NADPH can be detected fluorometrically by exciting NADPH at 350 nm and recording the fluorescence emission at 460 nm.

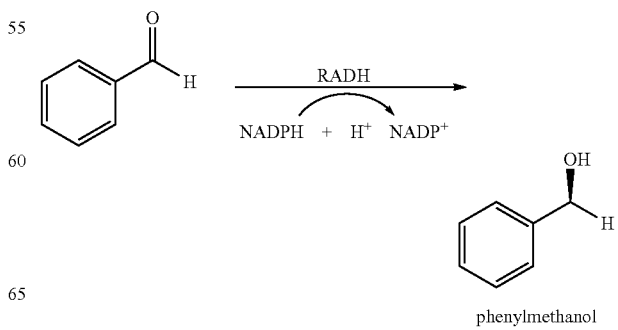

phenylmethanol

The assay was performed in semi-micro quartz cuvettes at 25° C. in TEA buffer (50 mM triethanolamine, pH 7.5) in a volume of 1 mL containing 0.8 mM calcium chloride, 10 mM benzaldehyde, 0.2 mM NADPH and 200 μl TDoT-RADH or 3HAMP-RADH suspensions in suitable dilutions. The conversion was monitored continuously for 90 s by using an excitation wavelength of 350 nm and an emission wavelength of 460 nm (2.8 nm excitation and emission bandwidth). To minimize light scattering due to turbid CatIB suspensions, fluorescence emission was detected at a 22.5° front-face angle. All reactions were measured at least in triplicate, the background was subtracted by a monitoring a blank reaction without enzyme. The activity distribution shown in FIG. 12 was determined as described for PfBAL.

Results and Discussion

TDoT-PfBAL and 3HAMP-RADH are Expressed in Insoluble Form in E. Coll.

Figure 12:
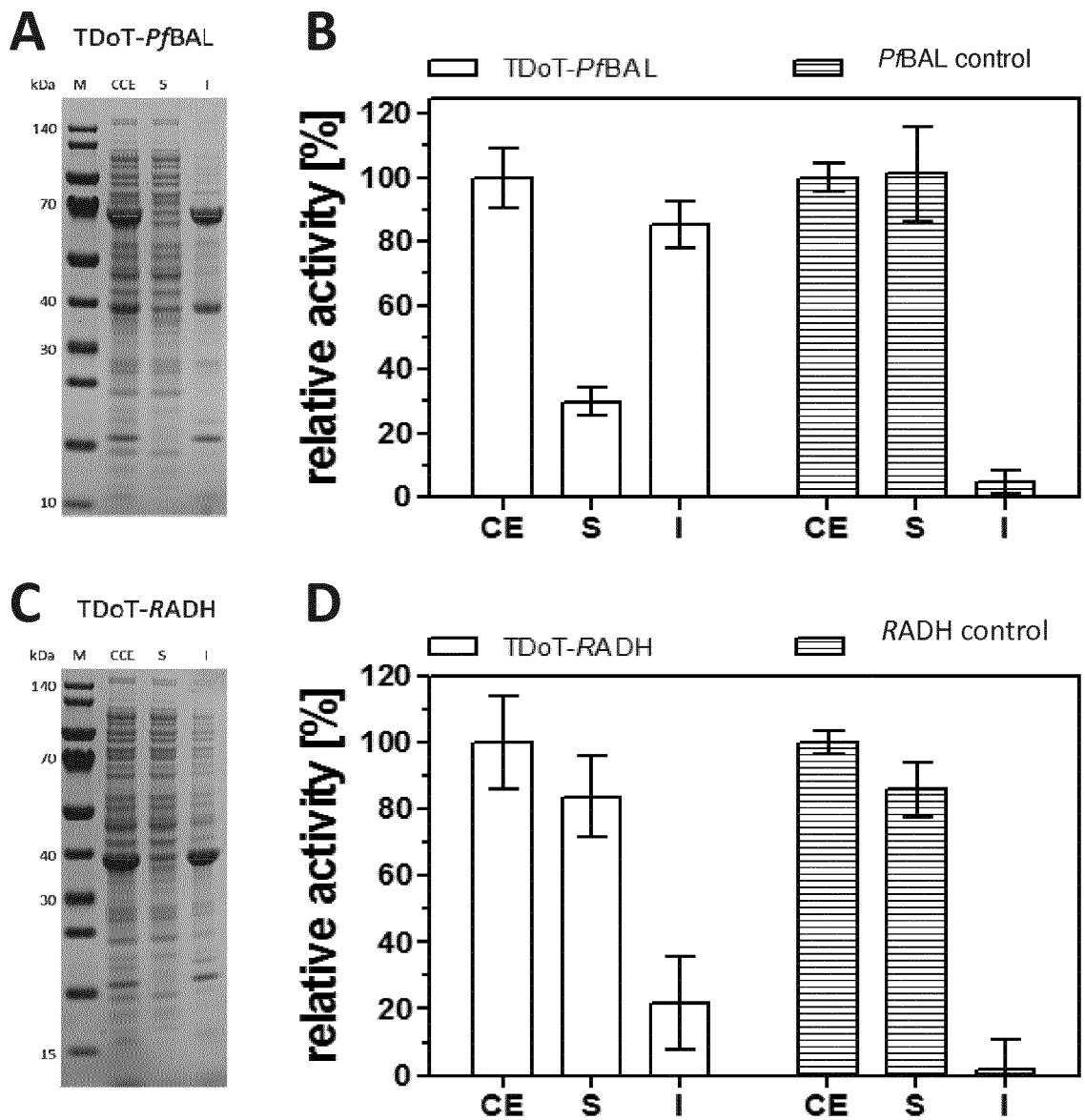
FIG. 12 shows SDS-PAGE analysis and activity distribution of TDoT-PfBAL (A, B), TDoT-RADH (C, D).

Under standard expression conditions previously described for the production of AtHNL, BsLA and EcMenD CatIBs [1], TDoT-PfBAL was produced in large amounts as insoluble inclusion bodies in *E. coli* BL21(DE3) (FIG. 12). FIG. 12 shows the SDS-PAGE analysis and activity distribution of TDoT-PfBAL (A, B), TDoT-RADH (C, D). After expression of the gene fusions in *E. coli* BL21(DE3), cells were harvested by centrifugation, resuspended in 50 mM sodium phosphate buffer pH 8.0 supplemented with 100 mM sodium chloride and lysed using a high-pressure homogenizer. The crude cell extract (CCE) was separated into the soluble protein fraction (S) and the insoluble protein fraction (I) by centrifugation (30 min, 15000 g, 4° C.). The latter one contains cell debris and inclusion bodies. Insoluble material was resuspended in the initial volume of milliQ water (A, C, E) or a suitable buffer (B, D, F) milliQ water. The total protein content in the soluble fraction was determined by using the Bradford assay [8]. SDS-PAGE samples were prepared by using a sample volume corresponding to 1 μg/μl soluble protein. SDS-PAGE samples of the insoluble fraction were prepared by using the same volume of the resuspended insoluble material. SDS-PAGE samples were denatured by incubation at 99° C. for 15 min. 10 μl of sample were loaded per gel lane. The red line marks the overexpression band of the respective gene fusion. PfBAL and RADH activity in crude cell extracts (CE), the soluble fraction (S) and the insoluble, inclusion body containing, fraction (I) was measured using fluorometric assays (see Materials and Methods for details). PfBAL and RADH activity in the soluble and insoluble fraction were expressed relative to the activity in the crude cell extract (set to 100%). As controls identically treated cultures producing soluble PfBAL and RADH were employed.

For both the PfBAL and the RADH target enzyme CatIB formation could be observed, with the TDoT-PfBAL fusion protein yielding more CatIBs (85±7% activity in the insoluble fraction) than TDoT-RADH (21±14% activity in the insoluble fraction).

Figure 13:
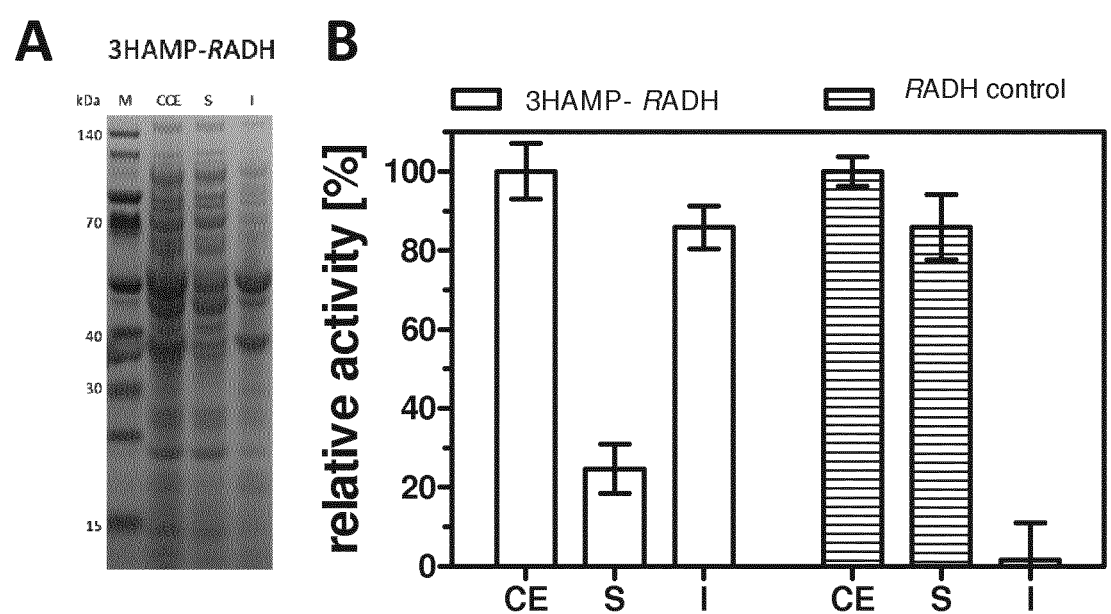
FIG. 13 shows the SDS-PAGE and activity distribution analyses of 3HAMP-RADH (C, D).

For RADH an alternative coiled-coil domain was tested. For RADH, the longer 3HAMP CC was selected as fusion partner. The corresponding gene fusion (3HAMP-RADH) was expressed in an identical manner as described for TDoT-RADH. FIG. 13 shows the corresponding SDS-PAGE and activity distribution analyses of 3HAMP-RADH (A, B). After expression of the gene fusions in *E. coli* BL21(DE3), cells were harvested by centrifugation, resuspended in 50 mM sodium phosphate buffer pH 8.0 supplemented with 100 mM sodium chloride and lysed using a high-pressure homogenizer. The crude cell extract (CCE) was separated into the soluble protein fraction (S) and the insoluble protein fraction (I) by centrifugation (30 min, 15000 g, 4° C.). The latter one contains cell debris and inclusion bodies. Insoluble material was resuspended in the initial volume of milliQ water (A) or a suitable buffer (B). The total protein content in the soluble fraction was determined by using the Bradford assay [8]. SDS-PAGE samples were prepared by using a sample volume corresponding to 1 μg/μl soluble protein. SDS-PAGE samples of the insoluble fraction were prepared by using the same volume of the resuspended insoluble material. SDS-PAGE samples were denatured by incubation at 99° C. for 10 min. 10 μl of sample were loaded per gel lane. The red line marks the overexpression band of the respective gene fusion. RADH activity as well as mCherry fluorescence in crude cell extracts (CE), the soluble (S) and insoluble (I) fractions were quantified as described in FIG. 12. As controls identically treated cultures producing soluble PfBAL, RADH and mCherry were employed.

Both alterations in the genetic design improved the overall yield of active protein in the insoluble fraction. Expression of 3HAMP-RADH results in 86±5% RADH activity in the insoluble fraction (FIG. 13).

In conclusion we here present additional evidence for the generic applicability of the previously described strategy which yields (catalytically) active inclusion bodies (CatIBs). The strategy relies on the molecular biological fusion of a CC domain to a given target enzyme. Additionally strategies that can improve CatIB yield are presented. Those include the use of alternative CC domains and shorter linker polypeptides.

Supplementary Material

```
TDoT-PfBAL
M   I   I   N   E   T   A   D   D   I   V   Y   R   L   T   V   I   I   D   D   R   Y   E   S
ATGATCATTAACGAAACTGCCGATGACATCGTTTATCGCCTGACAGTCATTATCGATGATCGCTACGAATCG
        TDoT

L   K   N   L   I   T   L   R   A   D   R   L   E   M   I   I   N   D   N   V   S   T   I   L   A
CTGAAAAACCTGATTACCTTACGTGCAGATCGCTTGGAGATGATCATCAATGACAATGTGTCCACCATTCTCGCG

S   I   T   S   I   E   G   R   A   S   G   G   G   S   G   G   G   S   G   G   G   S   G   S   M
AGCATTACTAGTATTGAAGGCCGTGCTAGCGGCGGTGGGTCTGGAGGCGGCTCAGGTGGTGGGTCGGGATCCATG
        SpeI        Xa      NheI        3xGGGS-Linker                       BamHI A   M   I   T   G   G   E   L   V   V   R   T   L   I   K   A   G   V   E   H   L   F   G   L   H
GCGATGATTACAGGCGGCGAACTGGTTGTTCGCACCCTAATAAAGGCTGGGGTCGAACATCTGTTCGGCCTGCAC
PfBAL G   A   H   I   D   T   I   F   Q   A   C   L   D   H   D   V   P   I   I   D   T   R   H   E   A
GGCGCGCATATCGATACGATTTTTCAAGCCTGTCTCGATCATGATGTGCCGATCATCGACACCCGCCATGAGGCC
```

```
A   A   G   H   A   A   E   G   Y   A   R   A   G   A   K   L   G   V   A   L   V   T   A   G   G
GCCGCAGGGCATGCGGCCGAGGGCTATGCCCGCGCTGGCGCCAAGCTGGGCGTGGCGCTGGTCACGGCGGGCGGG

G   F   T   N   A   V   T   P   I   A   N   A   W   L   D   R   T   P   V   L   F   L   T   G   S
GGATTTACCAATGCGGTCACGCCCATTGCCAACGCTTGGCTGGATCGCACGCCGGTGCTCTTCCTCACCGGATCG

G   A   L   R   D   D   E   T   N   T   L   Q   A   G   I   D   Q   V   A   M   A   A   P   I   T
GGCGCGCTGCGTGATGATGAAACCAACACGTTGCAGGCGGGGATTGATCAGGTCGCCATGGCGGCGCCCATTACC

K   W   A   H   R   V   M   A   T   E   H   I   P   R   L   V   M   Q   A   I   R   A   A   L   S
AAATGGGCGCATCGGGTGATGGCAACCGAGCATATCCCACGGCTGGTGATGCAGGCGATCCGCGCCGCGTTGAGC

A   P   R   G   P   V   L   L   D   L   P   W   D   I   L   M   N   Q   I   D   E   D   S   V   I
GCGCCACGCGGGCCGGTGTTGCTGGATCTGCCGTGGGATATTCTGATGAACCAGATTGATGAGGATAGCGTCATT

I   P   D   L   V   L   S   A   H   G   A   R   P   D   P   A   D   L   D   Q   A   L   A   L   L
ATCCCCGATCTGGTCTTGTCCGCACATGGGGCCAGACCCGACCCTGCCGATCTGGATCAGGCTCTCGCGCTTTTG

R   K   A   E   R   P   V   I   V   L   G   S   E   A   S   R   T   A   R   K   T   A   L   S   A
CGCAAGGCGGAGCGGCCGGTCATCGTGCTCGGCTCAGAAGCCTCGCGGACAGCGCGCAAGACGGCGCTTAGCGCA

F   V   A   A   T   G   V   P   V   F   A   D   Y   E   G   L   S   M   L   S   G   L   P   D   A
TTCGTGGCGGCGACTGGCGTGCCGGTGTTTGCCGATTATGAAGGGCTAAGCATGCTCTCGGGGCTGCCCGATGCT

M   R   G   G   L   V   Q   N   L   Y   S   F   A   K   A   D   A   A   P   D   L   V   L   M   L
ATGCGGGGCGGGCTGGTGCAAAACCTCTATTCTTTTGCCAAAGCCGATGCCGCGCCAGATCTCGTGCTGATGCTG

G   A   R   F   G   L   N   T   G   H   G   S   G   Q   L   I   P   H   S   A   Q   V   I   Q   V
GGGGCGCGCTTTGGCCTTAACACCGGGCATGGATCTGGGCAGTTGATCCCCCATAGCGCGCAGGTCATTCAGGTC

D   P   D   A   C   E   L   G   R   L   Q   G   I   A   L   G   I   V   A   D   V   G   G   T   I
GACCCTGATGCCTGCGAGCTGGGACGCCTGCAGGGCATCGCTCTGGGCATTGTGGCCGATGTGGGTGGGACCATC

E   A   L   A   Q   A   T   A   Q   D   A   A   W   P   D   R   G   D   W   C   A   K   V   T   D
GAGGCTTTGGCGCAGGCCACCGCGCAAGATGCGGCTTGGCCGGATCGCGGCGACTGGTGCGCCAAAGTGACGGAT

L   A   Q   E   R   Y   A   S   I   A   A   K   S   S   S   E   H   A   L   H   P   F   H   A   S
CTGGCGCAAGAGCGCTATGCCAGCATCGCTGCGAAATCGAGCAGCGAGCATGCGCTCCACCCCTTTCACGCCTCG

Q   V   I   A   K   H   V   D   A   G   V   T   V   V   A   D   G   A   L   T   Y   L   W   L   S
CAGGTCATTGCCAAACACGTCGATGCAGGGGTGACGGTGGTAGCGGATGGTGCGCTGACCTATCTCTGGCTGTCC

E   V   M   S   R   V   K   P   G   G   F   L   C   H   G   Y   L   G   S   M   G   V   G   F   G
GAAGTGATGAGCCGCGTGAAACCCGGCGGTTTTCTCTGCCACGGCTATCTAGGCTCGATGGGCGTGGGCTTCGGC

T   A   L   G   A   Q   V   A   D   L   E   A   G   R   R   T   I   L   V   T   G   D   G   S   V
ACGGCGCTGGGCGCGCAAGTGGCCGATCTTGAAGCAGGCCGCCGCACGATCCTTGTGACCGGCGATGGCTCGGTG

G   Y   S   I   G   E   F   D   T   L   V   R   K   Q   L   P   L   I   V   I   I   M   N   N   Q
GGCTATAGCATCGGTGAATTTGATACGCTGGTGCGCAAACAATTGCCGCTGATCGTCATCATCATGAACAACCAA

S   W   G   A   T   L   H   F   Q   Q   L   A   V   G   P   N   R   V   T   G   T   R   L   E   N
AGCTGGGGGGCGACATTGCATTTCCAGCAATTGGCCGTCGGCCCCAATCGCGTGACGGGCACCCGTTTGGAAAAT

G   S   Y   H   G   V   A   A   A   F   G   A   D   G   Y   H   V   D   S   V   E   S   F   S   A
GGCTCCTATCACGGGGTGGCCGCCGCCTTTGGCGCGGATGGCTATCATGTCGACAGTGTGGAGAGCTTTTCTGCG

A   L   A   Q   A   L   A   H   N   R   P   A   C   I   N   V   A   V   A   L   D   P   I   P   P
GCTCTGGCCCAAGCGCTCGCCCATAATCGCCCCGCCTGCATCAATGTCGCGGTCGCGCTCGATCCGATCCCGCCC

E   E   L   I   L   I   G   M   D   P   F   A   *
GAAGAACTCATTCTGATCGGCATGGACCCCTTCGCATAA

TDoT-RADH
M   I   I   N   E   T   A   D   D   I   V   Y   R   L   T   V   I   D   D   R   Y   Y   E   S
ATGATCATTAACGAAACTGCCGATGACATCGTTTATCGCCTGACAGTCATTATCGATGATCGCTACGAATCG
        TDoT

L   K   N   L   I   T   L   R   A   D   R   L   E   M   I   I   N   D   N   V   S   T   I   L   A
CTGAAAAACCTGATTACCTTACGTGCAGATCGCTTGGAGATGATCATCAATGACAATGTGTCCACCATTCTCGCG

S   I   T   S   I   E   G   R   A   S   G   G   G   S   G   G   G   S   G   G   G   S   G   S   M
AGCATTACTAGTATTGAAGGCCGTGCTAGCGGCGGTGGGTCTGGAGGCGGCTCAGGTGGTGGGTCGGGATCCATG
     SpeI       Xa      NheI       3xGGGS-Linker                    BamHI Y   R   L   L   N   K   T   A   V   I   T   G   G   N   S   G   I   G   L   A   T   A   K   R   F
TATCGTCTGCTGAATAAAACCGCAGTTATTACCGGTGGTAATAGCGGTATTGGTCTGGCAACCGCAAAACGTTTT
                                                                              RADH V   A   E   G   A   Y   V   F   I   V   G   R   R   R   K   E   L   E   Q   A   A   A   E   I   G
GTTGCCGAAGGTGCCTATGTTTTTATTGTTGGTCGTCGTCGTAAAGAACTGGAACAGGCAGCAGCAGAAATTGGT
```

-continued

```
R   N   V   T   A   V   K   A   D   V   T   K   L   E   D   L   D   R   L   Y   A   I   V   R   E
CGTAATGTTACCGCAGTTAAAGCCGATGTTACCAAACTGGAAGATCTGGATCGTCTGTATGCAATTGTTCGTGAA

Q   R   G   S   I   D   V   L   F   A   N   S   G   A   I   E   Q   K   T   L   E   E   I   T   P
CAGCGTGGTAGCATTGATGTTCTGTTTGCAAATAGCGGTGCCATTGAACAGAAAACCCTGGAAGAAATTACACCG

E   H   Y   D   R   T   F   D   V   N   V   R   G   L   I   F   T   V   Q   K   A   L   P   L   L
GAACATTATGATCGCACCTTTGATGTTAATGTGCGTGGTCTGATTTTTACCGTTCAGAAAGCACTGCCGCTGCTG

R   D   G   G   S   V   I   L   T   S   S   V   A   G   V   L   G   L   Q   A   H   D   T   Y   S
CGTGATGGTGGTAGCGTTATTCTGACCAGCAGCGTTGCCGGTGTTCTGGGTCTGCAGGCACATGATACCTATAGC

A   A   K   A   A   V   R   S   L   A   R   T   W   T   T   E   L   K   G   R   S   I   R   V   N
GCAGCAAAAGCAGCAGTTCGTAGCCTGGCACGTACCTGGACCACCGAACTGAAAGGTCGTAGCATTCGTGTTAAT

A   V   S   P   G   A   I   D   T   P   I   I   E   N   Q   V   S   T   Q   E   E   A   D   E   L
GCAGTTAGTCCGGGTGCAATTGATACCCCGATTATTGAAAATCAGGTTAGCACCCAGGAAGAAGCAGACGAACTG

R   A   K   F   A   A   A   T   P   L   G   R   V   G   R   P   E   E   L   A   A   A   V   L   F
CGCGCAAAATTTGCAGCAGCAACACCGCTGGGTCGTGTTGGTCGTCCGGAAGAACTGGCAGCAGCCGTTCTGTTT

L   A   S   D   D   S   S   Y   V   A   G   I   E   L   F   V   D   G   G   L   T   Q   V   *
CTGGCAAGTGATGATAGCAGCTATGTTGCAGGTATTGAACTGTTTGTTGATGGTGGTCTGACCCAGGTTTAA

3HAMP-RADH
M   G   L   F   N   A   H   A   V   A   Q   Q   R   A   D   R   I   A   T   L   L   Q   S   F
ATGGGCCTGTTTAACGCCCATGCAGTTGCGCAGCAACGCGCGGATCGCATTGCGACTCTCCTGCAGTCCTTT
    3Hamp A   D   G   Q   L   D   T   A   V   G   E   A   P   A   P   G   Y   E   R   L   Y   D   S   L   R
GCGGATGGTCAGTTGGACACCGCCGTGGGTGAAGCGCCAGCACCTGGTTACGAACGCCTGTATGACTCGCTTCGC A   L   Q   R   Q   L   R   E   Q   R   A   E   L   Q   Q   V   E   S   L   E   A   G   L   A   E
GCCCTTCAGCGCCAACTGCGCGAACAACGTGCGGAGTTACAACAGGTTGAGAGCCTGGAAGCAGGCTTGGCTGAA M   S   R   Q   H   E   A   G   W   I   D   Q   T   I   P   A   E   R   L   E   G   R   A   A   R
ATGAGTCGGCAGCATGAAGCAGGGTGGATTGACCAGACGATTCCGGCTGAACGGTTAGAGGGCCGTGCAGCACGT I   A   K   G   V   N   E   L   V   A   A   H   I   A   V   K   M   K   V   V   S   V   V   T   A
ATCGCCAAAGGCGTGAATGAGCTGGTTGCTGCGCACATTGCGGTGAAAATGAAAGTCGTGAGCGTAGTCACCGCG Y   G   Q   G   N   F   E   P   L   M   D   R   L   P   G   K   K   A   Q   I   T   E   A   I   D
TATGGCCAAGGGAACTTCGAACCGCTCATGGATCGCCTGCCGGGTAAGAAAGCCCAGATCACGGAGGCCATTGAT G   V   R   E   R   L   R   G   A   A   E   A   T   S   A   Q   L   A   T   A   A   Y   N   T   S
GGCGTACGTGAACGCCTGCGTGGAGCTGCTGAAGCGACCTCTGCGCAGCTGGCCACAGCCGCCTACAATACTAGT
                                                                           SpeI I   E   G   R   A   S   G   G   G   S   G   G   G   S   G   G   G   S   G   S   M   Y   R   L   L
ATTGAAGGCCGTGCTAGCGGCCGTGGGTCTGGAGGCGGCTCAGGTGGTGGGTCGGGATCCATGTATCGTCTGCTG
       Xa      NheI    3xGGGS-Linker                    BamHI N   K   T   A   V   I   T   G   G   N   S   G   I   G   L   A   T   A   K   R   F   V   A   E   G
AATAAAACCGCAGTTATTACCGGTGGTAATAGCGGTATTGGTCTGGCAACCGCAAAACGTTTTGTTGCCGAAGGT
RADH A   Y   V   F   I   V   G   R   R   R   K   E   L   E   Q   A   A   A   E   I   G   R   N   V   T
GCCTATGTTTTTATTGTTGGTCGTCGTCGTAAAGAACTGGAACAGGCAGCAGCAGAAATTGGTCGTAATGTTACC A   V   K   A   D   V   T   K   L   E   D   L   D   R   L   Y   A   I   V   R   E   Q   R   G   S
GCAGTTAAAGCCGATGTTACCAAACTGGAAGATCTGGATCGTCTGTATGCAATTGTTCGTGAACAGCGTGGTAGC I   D   V   L   F   A   N   S   G   A   I   E   Q   K   T   L   E   E   I   T   P   E   H   Y   D
ATTGATGTTCTGTTTGCAAATAGCGGTGCCATTGAACAGAAAACCCTGGAAGAAATTACACCGGAACATTATGAT R   T   F   D   V   N   V   R   G   L   I   F   T   V   Q   K   A   L   P   L   L   R   D   G   G
CGCACCTTTGATGTTAATGTGCGTGGTCTGATTTTTACCGTTCAGAAAGCACTGCCGCTGCTGCGTGATGGTGGT S   I   L   T   S   S   V   A   G   V   L   G   L   Q   A   H   D   T   Y   S   A   A   K   A
AGCGTTATTCTGACCAGCAGCGTTGCCGGTGTTCTGGGTCTGCAGGCACATGATACCTATAGCGCAGCAAAAGCA A   V   R   S   L   A   R   T   W   T   T   E   L   K   G   R   S   I   R   V   N   A   V   S   P
GCAGTTCGTAGCCTGGCACGTACCTGGACCACCGAACTGAAAGGTCGTAGCATTCGTGTTAATGCAGTTAGTCCG G   A   I   D   T   P   I   I   E   N   Q   V   S   T   Q   E   E   A   D   E   L   R   A   K   F
GGTGCAATTGATACCCCGATTATTGAAAATCAGGTTAGCACCCAGGAAGAAGCAGACGAACTGCGCGCAAAATTT
```

```
                        -continued
 A   A   A   T   P   L   G   R   V   G   R   P   E   E   L   A   A   A   V   L   F   L   A   S   D
GCAGCAGCAACACCGCTGGGTCGTGTTGGTCGTCCGGAAGAACTGGCAGCAGCCGTTCTGTTTCTGGCAAGTGAT D   S   S   Y   V   A   G   I   E   L   F   V   D   G   G   L   T   Q   V   *
GATAGCAGCTATGTTGCAGGTATTGAACTGTTTGTTGATGGTGGTCTGACCCAGGTTTAA
```

REFERENCES

[1] Diener, M., Kopka, B., Pohl, M., Jaeger, K. E., Krauss, U., Fusion of a Coiled-Coil Domain Facilitates the High-Level Production of Catalytically Active Enzyme Inclusion Bodies. *Chemcatchem* 2016, 8, 142-152.

[2] Airola, M. V., Watts, K. J., Bilwes, A. M., Crane, B. R., Structure of concatenated HAMP domains provides a mechanism for signal transduction. *Structure* 2010, 18, 436-448.

[3] Hinrichsen, P., Gomez, I., Vicuna, R., Cloning and sequencing of the gene encoding benzaldehyde lyase from *Pseudomonas fluorescens* biovar I. *Gene* 1994, 144, 137-138

[4] Kulig, J., Frese, A., Kroutil, W., Pohl, M., Rother, D., Biochemical characterization of an alcohol dehydrogenase from *Ralstonia* sp. *Biotechnology and bioengineering* 2013, 110, 1838-1848.

[5] Shaner, N. C., Campbell, R. E., Steinbach, P. A., Giepmans, B. N., et al., Improved monomeric red, orange and yellow fluorescent proteins derived from *Discosoma* sp. red fluorescent protein. *Nature biotechnology* 2004, 22, 1567-1572.

[6] Stetefeld, J., Jenny, M., Schulthess, T., Landwehr, R., et al., Crystal structure of a naturally occurring parallel right-handed coiled coil tetramer. *Nature structural biology* 2000, 7, 772-776.

[7] Zavrel, M., Schmidt, T., Michalik, C., Ansorge-Schumacher, M., et al., Mechanistic kinetic model for symmetric carboligations using benzaldehyde lyase. *Biotechnology and bioengineering* 2008, 101, 27-38.

[8] Bradford, M. M., A rapid and sensitive method for the quantitation of microgram quantities of protein utilizing the principle of protein-dye binding. *Analytical biochemistry* 1976, 72, 248-254.

---

The invention claimed is:

1. A water-insoluble protein aggregate comprising a fusion protein, wherein said fusion protein comprises a coiled-coil domain and a catalytic domain, said water-insoluble protein aggregate possesses catalytic activity and the fusion protein is aggregated in an inclusion body, wherein the coiled-coil domain is encoded by a nucleotide sequence selected from the group consisting of SEQ ID NO: 2 and SEQ ID NO: 4, or nucleotide sequences having at least 80% sequence identity to said nucleotide sequences, and wherein said nucleotide sequence of SEQ ID NO: 2 or SEQ ID NO: 4 encodes the amino acid sequence of SEQ ID NO:1 or SEQ ID NO:3, respectively.

2. The protein-aggregate according to claim 1, wherein the fusion protein is a N-terminal fusion protein wherein the coiled-coil domain is at the amino terminal end of the catalytic domain thereof.

3. The protein aggregate according to claim 1, wherein the fusion protein is a C-terminal fusion protein, wherein the coiled-coil domain is at the carboxyl-terminal end of the catalytic domain thereof.

4. The protein aggregate according to claim 1, wherein the catalytic domain originates, or is derived from, an enzyme belonging to the enzyme classification class EC 1, EC 2, EC 3 or EC 4.

5. The protein aggregate according to claim 4, wherein the catalytic domain originates, or is derived from, an enzyme belonging to the enzyme classification class EC 1.1, EC 2.2, EC 3.1 or EC 4.1.

6. The protein aggregate according to claim 5, wherein the catalytic domain originates, or is derived from, an enzyme belonging to the enzyme classification class EC 1.1.1, EC 2.2.1, EC 3.1.1 or EC 4.1.2.

7. The protein-aggregate according to claim 1, wherein the coiled-coil domain is encoded by a nucleotide sequence having at least 90% sequence identity to a nucleotide sequence selected from the group consisting of SEQ ID NO: 2 and SEQ ID NO: 4.

8. The protein aggregate according to claim 1, wherein the nucleotide sequence encoding the coiled-coil domain
   is selected from the group of nucleotide sequences consisting of SEQ ID NO:2 and SEQ ID NO: 4.

9. The protein aggregate according to claim 8, wherein the nucleotide sequence encoding the fusion protein comprises at least one nucleotide sequence selected from the group consisting of a nucleotide sequence encoding a linker, a nucleotide sequence encoding a tag and a nucleotide sequence encoding an endopeptidase cleavage site.

10. The protein aggregate according to claim 8, wherein the nucleic acid sequence encoding the fusion protein is operably linked to at least one regulatory element for heterologous expression of said fusion protein in a bacterial cell.

11. A method for performing a biocatalytic process comprising employing the catalytic domain of the water-insoluble protein aggregate of claim 1 in the biocatalytic process.

* * * * *

SEQUENCE LISTING

```
<160> NUMBER OF SEQ ID NOS: 99

<210> SEQ ID NO 1
<211> LENGTH: 51
<212> TYPE: PRT
<213> ORGANISM: Staphylothermus marinus

<400> SEQUENCE: 1

Met Ile Ile Asn Glu Thr Ala Asp Asp Ile Val Tyr Arg Leu Thr Val
1               5                   10                  15

Ile Ile Asp Asp Arg Tyr Glu Ser Leu Lys Asn Leu Ile Thr Leu Arg
            20                  25                  30

Ala Asp Arg Leu Glu Met Ile Ile Asn Asp Asn Val Ser Thr Ile Leu
        35                  40                  45

Ala Ser Ile
    50

<210> SEQ ID NO 2
<211> LENGTH: 153
<212> TYPE: DNA
<213> ORGANISM: Staphylothermus marinus

<400> SEQUENCE: 2
atgatcatta acgaaactgc cgatgacatc gtttatcgcc tgacagtcat tatcgatgat      60
cgctacgaat cgctgaaaaa cctgattacc ttacgtgcag atcgcttgga gatgatcatc     120
aatgacaatg tgtccaccat tctcgcgagc att                                  153

<210> SEQ ID NO 3
<211> LENGTH: 172
<212> TYPE: PRT
<213> ORGANISM: Pseudomonas aeruginosa

<400> SEQUENCE: 3

Met Gly Leu Phe Asn Ala His Ala Val Ala Gln Gln Arg Ala Asp Arg
1               5                   10                  15

Ile Ala Thr Leu Leu Gln Ser Phe Ala Asp Gly Gln Leu Asp Thr Ala
            20                  25                  30
```

```
Val Gly Glu Ala Pro Ala Pro Gly Tyr Glu Arg Leu Tyr Asp Ser Leu
         35                  40                  45

Arg Ala Leu Gln Arg Gln Leu Arg Glu Gln Arg Ala Glu Leu Gln Gln
     50                  55                  60

Val Glu Ser Leu Glu Ala Gly Leu Ala Glu Met Ser Arg Gln His Glu
 65                  70                  75                  80

Ala Gly Trp Ile Asp Gln Thr Ile Pro Ala Glu Arg Leu Glu Gly Arg
                 85                  90                  95

Ala Ala Arg Ile Ala Lys Gly Val Asn Glu Leu Val Ala Ala His Ile
            100                 105                 110

Ala Val Lys Met Lys Val Val Ser Val Val Thr Ala Tyr Gly Gln Gly
        115                 120                 125

Asn Phe Glu Pro Leu Met Asp Arg Leu Pro Gly Lys Lys Ala Gln Ile
    130                 135                 140

Thr Glu Ala Ile Asp Gly Val Arg Glu Arg Leu Arg Gly Ala Ala Glu
145                 150                 155                 160

Ala Thr Ser Ala Gln Leu Ala Thr Ala Ala Tyr Asn
                165                 170
```

<210> SEQ ID NO 4
<211> LENGTH: 516
<212> TYPE: DNA
<213> ORGANISM: Pseudomonas aeruginosa

<400> SEQUENCE: 4

```
atgggcctgt ttaacgccca tgcagttgcg cagcaacgcg cggatcgcat tgcgactctc      60
ctgcagtcct ttgcggatgg tcagttggac accgccgtgg gtgaagcgcc agcacctggt     120
tacgaacgcc tgtatgactc gcttcgcgcc cttcagcgcc aactgcgcga caacgtgcg      180
gagttacaac aggttgagag cctggaagca ggcttggctg aaatgagtcg gcagcatgaa     240
gcagggtgga ttgaccagac gattccggct gaacggttag agggccgtgc agcacgtatc     300
gccaaaggcg tgaatgagct ggttgctgcg cacattgcgg tgaaaatgaa agtcgtgagc     360
gtagtcaccg cgtatggcca agggaacttc gaaccgctca tggatcgcct gccgggtaag     420
aaagcccaga tcacggaggc cattgatggc gtacgtgaac gcctgcgtgg agctgctgaa     480
gcgacctctg cgcagctggc cacagccgcc tacaat                               516
```

<210> SEQ ID NO 5
<211> LENGTH: 35
<212> TYPE: PRT
<213> ORGANISM: Saccharomyces cerevisiae

<400> SEQUENCE: 5

```
Met Arg Met Lys Gln Leu Glu Asp Lys Val Glu Glu Leu Leu Ser Lys
  1               5                  10                  15

Asn Tyr His Leu Glu Asn Glu Val Ala Arg Leu Lys Lys Leu Val Gly
             20                  25                  30

Glu Arg Gly
         35
```

<210> SEQ ID NO 6
<211> LENGTH: 105
<212> TYPE: DNA
<213> ORGANISM: Saccharomyces cerevisiae

<400> SEQUENCE: 6
atgcggatga agcagttaga ggataaagtg gaagagttac tcagcaagaa ctatcatctc      60
gagaatgagg ttgctcgctt gaagaaactg gtaggtgaac gtggt                    105

<210> SEQ ID NO 7
<211> LENGTH: 35
<212> TYPE: PRT
<213> ORGANISM: Artificial Sequence
<220> FEATURE:
<223> OTHER INFORMATION: Variant of the GCN4-p1 domain of the GCN4
      transcription factor of Saccharomyces cerevisiae

<400> SEQUENCE: 7

Met Arg Met Lys Gln Ile Glu Asp Lys Leu Glu Glu Ile Leu Ser Lys
1               5                   10                  15

Leu Tyr His Ile Glu Asn Glu Leu Ala Arg Ile Lys Lys Leu Leu Gly
            20                  25                  30

Glu Arg Gly
        35

<210> SEQ ID NO 8
<211> LENGTH: 105
<212> TYPE: DNA
<213> ORGANISM: Artificial Sequence
<220> FEATURE:
<223> OTHER INFORMATION: Nucleotide sequence encoding a variant of the
      GCN4-p1 domain of the GCN4 transcription factor of Saccharomyces
      cerevisiae

<400> SEQUENCE: 8
atgcgcatga acagattga ggataaactg gaagaaatcc tgagcaaact ctatcatatc       60
gagaacgaat tagcgcgcat taagaaactg ttgggtgaac gtggc                    105

<210> SEQ ID NO 9
<211> LENGTH: 258
<212> TYPE: PRT
<213> ORGANISM: Arabidopsis thaliana

<400> SEQUENCE: 9

Met Glu Arg Lys His His Phe Val Leu Val His Asn Ala Tyr His Gly
1               5                   10                  15

Ala Trp Ile Trp Tyr Lys Leu Lys Pro Leu Leu Glu Ser Ala Gly His
            20                  25                  30

Arg Val Thr Ala Val Glu Leu Ala Ala Ser Gly Ile Asp Pro Arg Pro
        35                  40                  45

Ile Gln Ala Val Glu Thr Val Asp Glu Tyr Ser Lys Pro Leu Ile Glu
    50                  55                  60

Thr Leu Lys Ser Leu Pro Glu Asn Glu Glu Val Ile Leu Val Gly Phe
65                  70                  75                  80

Ser Phe Gly Gly Ile Asn Ile Ala Leu Ala Ala Asp Ile Phe Pro Ala
                85                  90                  95

Lys Ile Lys Val Leu Val Phe Leu Asn Ala Phe Leu Pro Asp Thr Thr
            100                 105                 110

His Val Pro Ser His Val Leu Asp Lys Tyr Met Glu Met Pro Gly Gly
        115                 120                 125

Leu Gly Asp Cys Glu Phe Ser Ser His Glu Thr Arg Asn Gly Thr Met
    130                 135                 140

Ser Leu Leu Lys Met Gly Pro Lys Phe Met Lys Ala Arg Leu Tyr Gln
145                 150                 155                 160

```
Asn Cys Pro Ile Glu Asp Tyr Glu Leu Ala Lys Met Leu His Arg Gln
            165                 170                 175
Gly Ser Phe Phe Thr Glu Asp Leu Ser Lys Lys Glu Lys Phe Ser Glu
        180                 185                 190
Glu Gly Tyr Gly Ser Val Gln Arg Val Tyr Val Met Ser Ser Glu Asp
    195                 200                 205
Lys Ala Ile Pro Cys Asp Phe Ile Arg Trp Met Ile Asp Asn Phe Asn
210                 215                 220
Val Ser Lys Val Tyr Glu Ile Asp Gly Gly Asp His Met Val Met Leu
225                 230                 235                 240
Ser Lys Pro Gln Lys Leu Phe Asp Ser Leu Ser Ala Ile Ala Thr Asp
                245                 250                 255
Tyr Met

<210> SEQ ID NO 10
<211> LENGTH: 777
<212> TYPE: DNA
<213> ORGANISM: Arabidopsis thaliana

<400> SEQUENCE: 10
atggagagga aacatcactt cgtgttagtt cacaacgctt atcatggagc ctggatctgg      60
tacaagctca agcccctcct tgaatcagcc ggccaccgcg ttactgctgt cgaactcgcc     120
gcctccggga tcgacccacg accaatccag gccgttgaaa ccgtcgacga atactccaaa     180
ccgttgatcg aaaccctcaa atctcttcca gagaacgaag aggtaattct ggttggattc     240
agcttcggag gcatcaacat cgctctcgcc gccgacatat ttccggcgaa gattaaggtt     300
cttgtgttcc tcaacgcctt cttgcccgac acaacccacg tgccttctca cgttctggac     360
aagtatatgg agatgcctgg aggtttggga gattgtgagt tttcatctca tgaaacaaga     420
aatgggacga tgagtttatt gaagatggga ccaaaattca tgaaggcacg tctttaccaa     480
aattgtccca tagaggatta cgagctggca aaaatgttgc ataggcaagg gtcattttc     540
acagaggatc tatcaaagaa agaaaagttt agcgaggaag atatggttc ggtgcaacga     600
gtttacgtaa tgagtagtga agacaaagcc atcccctgcg atttcattcg ttggatgatt     660
gataatttca acgtctcgaa agtctacgag atcgatggcg gagatcacat ggtgatgctc     720
tccaaacccc aaaaactctt tgactctctc tctgctattg ccaccgatta tatgtaa      777

<210> SEQ ID NO 11
<211> LENGTH: 556
<212> TYPE: PRT
<213> ORGANISM: Escherichia coli

<400> SEQUENCE: 11

Met Ser Val Ser Ala Phe Asn Arg Arg Trp Ala Ala Val Ile Leu Glu
1               5                   10                  15
Ala Leu Thr Arg His Gly Val Arg His Ile Cys Ile Ala Pro Gly Ser
            20                  25                  30
Arg Ser Thr Pro Leu Thr Leu Ala Ala Ala Glu Asn Ser Ala Phe Ile
        35                  40                  45
His His Thr His His Phe Asp Glu Arg Gly Leu Gly His Leu Ala Leu Gly
    50                  55                  60
Leu Ala Lys Val Ser Lys Gln Pro Val Ala Val Ile Val Thr Ser Gly
65                  70                  75                  80
Thr Ala Val Ala Asn Leu Tyr Pro Ala Leu Ile Glu Ala Gly Leu Thr
                85                  90                  95
```

```
Gly Glu Lys Leu Ile Leu Leu Thr Ala Asp Arg Pro Glu Leu Ile
            100                 105                 110

Asp Cys Gly Ala Asn Gln Ala Ile Arg Gln Pro Gly Met Phe Ala Ser
            115                 120                 125

His Pro Thr His Ser Ile Ser Leu Pro Arg Pro Thr Gln Asp Ile Pro
            130                 135                 140

Ala Arg Trp Leu Val Ser Thr Ile Asp His Ala Leu Gly Thr Leu His
145                 150                 155                 160

Ala Gly Gly Val His Ile Asn Cys Pro Phe Ala Glu Pro Leu Tyr Gly
                165                 170                 175

Glu Met Asp Asp Thr Gly Leu Ser Trp Gln Gln Arg Leu Gly Asp Trp
            180                 185                 190

Trp Gln Asp Asp Lys Pro Trp Leu Arg Glu Ala Pro Arg Leu Glu Ser
            195                 200                 205

Glu Lys Gln Arg Asp Trp Phe Phe Trp Arg Gln Lys Arg Gly Val Val
            210                 215                 220

Val Ala Gly Arg Met Ser Ala Glu Glu Gly Lys Lys Val Ala Leu Trp
225                 230                 235                 240

Ala Gln Thr Leu Gly Trp Pro Leu Ile Gly Asp Val Leu Ser Gln Thr
            245                 250                 255

Gly Gln Pro Leu Pro Cys Ala Asp Leu Trp Leu Gly Asn Ala Lys Ala
            260                 265                 270

Thr Ser Glu Leu Gln Gln Ala Gln Ile Val Val Gln Leu Gly Ser Ser
            275                 280                 285

Leu Thr Gly Lys Arg Leu Leu Gln Trp Gln Ala Ser Cys Glu Pro Glu
            290                 295                 300

Glu Tyr Trp Ile Val Asp Ile Glu Gly Arg Leu Asp Pro Ala His
305                 310                 315                 320

His Arg Gly Arg Arg Leu Ile Ala Asn Ile Ala Asp Trp Leu Glu Leu
                325                 330                 335

His Pro Ala Glu Lys Arg Gln Pro Trp Cys Val Glu Ile Pro Arg Leu
            340                 345                 350

Ala Glu Gln Ala Met Gln Ala Val Ile Ala Arg Arg Asp Ala Phe Gly
            355                 360                 365

Glu Ala Gln Leu Ala His Arg Ile Cys Asp Tyr Leu Pro Glu Gln Gly
            370                 375                 380

Gln Leu Phe Val Gly Asn Ser Leu Val Val Arg Leu Ile Asp Ala Leu
385                 390                 395                 400

Ser Gln Leu Pro Ala Gly Tyr Pro Val Tyr Ser Asn Arg Gly Ala Ser
            405                 410                 415

Gly Ile Asp Gly Leu Leu Ser Thr Ala Ala Gly Val Gln Arg Ala Ser
            420                 425                 430

Gly Lys Pro Thr Leu Ala Ile Val Gly Asp Leu Ser Ala Leu Tyr Asp
            435                 440                 445

Leu Asn Ala Leu Ala Leu Leu Arg Gln Val Ser Ala Pro Leu Val Leu
            450                 455                 460

Ile Val Val Asn Asn Gly Gly Gln Ile Phe Ser Leu Leu Pro Thr
465                 470                 475                 480

Pro Gln Ser Glu Arg Glu Arg Phe Tyr Leu Met Pro Gln Asn Val His
            485                 490                 495

Phe Glu His Ala Ala Ala Met Phe Glu Leu Lys Tyr His Arg Pro Gln
            500                 505                 510
```

```
Asn Trp Gln Glu Leu Glu Thr Ala Phe Ala Asp Ala Trp Arg Thr Pro
            515                 520                 525

Thr Thr Thr Val Ile Glu Met Val Val Asn Asp Thr Asp Gly Ala Gln
        530                 535                 540

Thr Leu Gln Gln Leu Leu Ala Gln Val Ser His Leu
545                 550                 555

<210> SEQ ID NO 12
<211> LENGTH: 1671
<212> TYPE: DNA
<213> ORGANISM: Escherichia coli

<400> SEQUENCE: 12
atgtcagtaa gcgcatttaa ccgacgctgg gcggcggtca ttctggaagc attaacgcgt      60
cacggcgtca gacacatctg tatcgcccca ggctcgcgtt ctacaccgtt aacgttagcg     120
gcggcggaga attccgcatt cattcaccac acccatttcg atgagcgtgg gttggggcat     180
ctggcgctgg gctggcgaa agtcagcaag cagccggtgg cggtgattgt gacctccggc     240
acggcggtgg caaatctcta tccggcactg attgaagccg gttaaccgg agaaaaactg     300 attctcttaa ccgccgatcg cccgccggag ctaattgact gcggcgcgaa tcaggcaatt     360
cgccagccgg aatgttcgc ctctcacccc acgcacagta tttcattgcc gcgcccgacc     420
caggatatcc ccgcacgttg gctggttct accatcgacc acgctctcgg tacgcttcat     480 gcgggggggag tccatatcaa ctgcccgttt gctgaaccgc tgtatggcga atggacgat     540 accgggctta gctggcaaca gcgtctgggt gactggtggc aggacgacaa accgtggctg     600
cgtgaagcgc ctcgtctgga aagtgaaaaa cagcgcgact ggttcttctg gcgacaaaag     660
cgcggcgtgg tggttgccgg gcgcatgagt gcggaagagg gcaaaaaagt tgccctgtgg     720
gcgcaaactc ttggctggcc gctgattggc gatgtgctgt cacaaaccgg gcagccgctg     780
ccgtgtgccg atctttggtt aggcaatgcc aaagcgacca gcgagctgca gcaggcgcaa     840
attgtggtgc aactgggaag cagcctgacg gggaaacggc tcctgcaatg gcaggcaagc     900
tgtgaaccag aagagtactg gattgttgat gacattgaag gcgacttga tccggcacac     960 catcgcggac gtcgcttaat tgccaatatt gccgactggc tggagctgca tccggcagaa    1020
aaacgccagc cctggtgcgt tgaaatcccg cgcctggcgg aacaggcaat gcaggcggtt    1080
attgcccgcc gtgatgcgtt tggcgaagcg caactgcgc atcgcatctg cgactatctg    1140
cctgaacagg ggcaattgtt tgttggtaac agcctggtgg tacgtctgat tgatgcgctt    1200
tcgcaacttc cggcaggtta cccggtgtac agcaaccgtg gggccagcgg tatcgacggg    1260
ctgctttcga ccgccgccgg cgttcagcgg gcaagcggca aaccgacgct ggcgattgtg    1320
ggcgatctct ccgcacttta cgatctcaac gcgctggcgt tattgcgtca ggtttctgcg    1380
ccgctggtat taattgtggt gaacaacaac ggcgggcaaa ttttctcgct gttgccaacg    1440
ccgcaaagcg agcgtgagcg tttctatctg atgccgcaaa acgtccattt tgagcacgcc    1500
gccgcgatgt tcgagctgaa atatcatcgt ccgcaaaact ggcaggaact tgaaacggca    1560
tttgccgacg cctggcgcac gccaaccacc acggtgattg aaatggtggt taacgacacc    1620
gatggtgcgc aaacgctcca gcaacttctg gcgcaggtaa gccatttatg a             1671

<210> SEQ ID NO 13
<211> LENGTH: 180
<212> TYPE: PRT
<213> ORGANISM: Bacillus subtilis
```

<400> SEQUENCE: 13

Ala Glu His Asn Pro Val Val Met Val His Gly Ile Gly Gly Ala Ser
1               5                   10                  15

Phe Asn Phe Ala Gly Ile Lys Ser Tyr Leu Val Ser Gln Gly Trp Ser
            20                  25                  30

Arg Asp Lys Leu Tyr Ala Val Asp Phe Trp Asp Lys Thr Gly Thr Asn
        35                  40                  45

Tyr Asn Asn Gly Pro Val Leu Ser Arg Phe Val Gln Lys Val Leu Asp
    50                  55                  60

Glu Thr Gly Ala Lys Lys Val Asp Ile Val Ala His Ser Met Gly Gly
65                  70                  75                  80

Ala Asn Thr Leu Tyr Tyr Ile Lys Asn Leu Asp Gly Gly Asn Lys Val
                85                  90                  95

Ala Asn Val Val Thr Leu Gly Gly Ala Asn Arg Leu Thr Thr Gly Lys
            100                 105                 110

Ala Leu Pro Gly Thr Asp Pro Asn Gln Lys Ile Leu Tyr Thr Ser Ile
        115                 120                 125

Tyr Ser Ser Ala Asp Met Ile Val Met Asn Tyr Leu Ser Arg Leu Asp
    130                 135                 140

Gly Ala Arg Asn Val Gln Ile His Gly Val Gly His Ile Gly Leu Leu
145                 150                 155                 160

Tyr Ser Ser Gln Val Asn Ser Leu Ile Lys Glu Gly Leu Asn Gly Gly
                165                 170                 175

Gly Gln Asn Thr
            180

<210> SEQ ID NO 14
<211> LENGTH: 543
<212> TYPE: DNA
<213> ORGANISM: Bacillus subtilis

<400> SEQUENCE: 14
gctgaacaca atccagtcgt tatggttcac ggtattggag gggcatcatt caattttgcg      60
ggaattaaga gctatctcgt atctcagggc tggtcgcggg acaagctgta tgcagttgat     120
ttttgggaca agacaggcac aaattataac aatggaccgg tattatcacg atttgtgcaa     180
aaggttttag atgaaacggg tgcgaaaaaa gtggatattg tcgctcacag catggggggc     240
gcgaacacac tttactacat aaaaaatctg gacggcggaa ataaagttgc aaacgtcgtg     300
acgcttggcg gcgcgaaccg tttgacgaca ggcaaggcgc ttccgggaac agatccaaat     360
caaaagattt tatacacatc catttacagc agtgccgata tgattgtcat gaattactta     420
tcaagattag atggtgctag aaacgttcaa atccatggcg ttggacacat cggccttctg     480
tacagcagcc aagtcaacag cctgattaaa gaagggctga acggcggggg ccagaatacg     540
tag                                                                   543

<210> SEQ ID NO 15
<211> LENGTH: 16
<212> TYPE: PRT
<213> ORGANISM: Artificial Sequence
<220> FEATURE:
<223> OTHER INFORMATION: Peptide fragment comprising the amino acid
      motif GGGS three times; for use as linker between different
      peptide domains

<400> SEQUENCE: 15

Ala Ser Gly Gly Gly Ser Gly Gly Gly Ser Gly Gly Gly Ser Gly Ser
1               5                   10                  15

<210> SEQ ID NO 16
<211> LENGTH: 48
<212> TYPE: DNA
<213> ORGANISM: Artificial Sequence
<220> FEATURE:
<223> OTHER INFORMATION: Nucleotide sequence encoding a peptide fragment
      comprising the amino acid motif GGGS three times; for use as
      linker between different peptide domains

<400> SEQUENCE: 16
gctagcggcg gtgggtctgg aggcggctca ggtggtgggt cgggatcc                48

<210> SEQ ID NO 17
<211> LENGTH: 2
<212> TYPE: PRT
<213> ORGANISM: Artificial Sequence
<220> FEATURE:
<223> OTHER INFORMATION: Peptide fragment for use as linker between
      different peptide domains

<400> SEQUENCE: 17

Glu Leu
1

<210> SEQ ID NO 18
<211> LENGTH: 6
<212> TYPE: DNA
<213> ORGANISM: Artificial Sequence
<220> FEATURE:
<223> OTHER INFORMATION: Nucleotide sequence encoding a peptide fragment
      for use as linker between different peptide domains

<400> SEQUENCE: 18 cagctc                                                              6

<210> SEQ ID NO 19
<211> LENGTH: 5
<212> TYPE: PRT
<213> ORGANISM: Artificial Sequence
<220> FEATURE:
<223> OTHER INFORMATION: Peptide fragment for use as linker between
      different peptide domains

<400> SEQUENCE: 19

Thr Ser Ala Gly Ser
1               5

<210> SEQ ID NO 20
<211> LENGTH: 15
<212> TYPE: DNA
<213> ORGANISM: Artificial Sequence
<220> FEATURE:
<223> OTHER INFORMATION: CNucleotide sequence encoding a peptide
      fragment for use as linker between different peptide domains
<220> FEATURE:
<221> NAME/KEY: misc_feature
<222> LOCATION: (9)..(9)
<223> OTHER INFORMATION: n is a, c, g, or t

<400> SEQUENCE: 20
actagtgcng gatcc                                                    15

```
<210> SEQ ID NO 21
<211> LENGTH: 15
<212> TYPE: PRT
<213> ORGANISM: Artificial Sequence
<220> FEATURE:
<223> OTHER INFORMATION: Peptide that is capable of being biotinylated
      by the enzyme BirA enabeling an isolation by  streptavidin

<400> SEQUENCE: 21

Gly Leu Asn Asp Ile Phe Glu Ala Gln Lys Ile Glu Trp His Glu
1               5                   10                  15

<210> SEQ ID NO 22
<211> LENGTH: 26
<212> TYPE: PRT
<213> ORGANISM: Artificial Sequence
<220> FEATURE:
<223> OTHER INFORMATION: Peptide that can be bound by the protein
      Calmodulin

<400> SEQUENCE: 22

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 23
<211> LENGTH: 6
<212> TYPE: PRT
<213> ORGANISM: Artificial Sequence
<220> FEATURE:
<223> OTHER INFORMATION: Peptide that can bind efficiently to an anion-
      exchange resin

<400> SEQUENCE: 23

Glu Glu Glu Glu Glu Glu
1               5

<210> SEQ ID NO 24
<211> LENGTH: 13
<212> TYPE: PRT
<213> ORGANISM: Artificial Sequence
<220> FEATURE:
<223> OTHER INFORMATION: Peptide being recognizable by a specific
      antibody

<400> SEQUENCE: 24

Gly Ala Pro Val Pro Tyr Pro Asp Pro Leu Glu Pro Arg
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Peptide being recognizable by a specific
      antibody

<400> SEQUENCE: 25

Asp Tyr Lys Asp Asp Asp Asp Lys
1               5

<210> SEQ ID NO 26
<211> LENGTH: 9
<212> TYPE: PRT
<213> ORGANISM: Artificial Sequence
```

```
<220> FEATURE:
<223> OTHER INFORMATION: Peptide being recognizable by a specific
      antibody

<400> SEQUENCE: 26

Tyr Pro Tyr Asp Val Pro Asp Tyr Ala
1               5

<210> SEQ ID NO 27
<211> LENGTH: 6
<212> TYPE: PRT
<213> ORGANISM: Artificial Sequence
<220> FEATURE:
<223> OTHER INFORMATION: Peptide that can be bound by a nickel or cobalt
      chelate

<400> SEQUENCE: 27

His His His His His His
1               5

<210> SEQ ID NO 28
<211> LENGTH: 10
<212> TYPE: PRT
<213> ORGANISM: Artificial Sequence
<220> FEATURE:
<223> OTHER INFORMATION: Peptide being recognizable by a specific
      antibody

<400> SEQUENCE: 28

Glu Gln Lys Leu Ile Ser Glu Glu Asp Leu
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Oligopeptide derived from pancreatic
      ribonuclease A, recognizable by a specific antibody

<400> SEQUENCE: 29

Lys Glu Thr Ala Ala Ala Lys Phe Glu Arg Gln His Met Asp Ser
1               5                   10                  15

<210> SEQ ID NO 30
<211> LENGTH: 38
<212> TYPE: PRT
<213> ORGANISM: Artificial Sequence
<220> FEATURE:
<223> OTHER INFORMATION: Peptide capable of binding streptavidin

<400> SEQUENCE: 30

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 31
<211> LENGTH: 13
<212> TYPE: PRT
<213> ORGANISM: Artificial Sequence
<220> FEATURE:
<223> OTHER INFORMATION: Peptide-tag initially intended for mammalian
      expression
```

```
<400> SEQUENCE: 31

Ser Leu Ala Glu Leu Leu Asn Ala Gly Leu Gly Gly Ser
1               5                   10

<210> SEQ ID NO 32
<211> LENGTH: 8
<212> TYPE: PRT
<213> ORGANISM: Artificial Sequence
<220> FEATURE:
<223> OTHER INFORMATION: Peptide tag for prokaryotic protein expreesion

<400> SEQUENCE: 32

Thr Gln Asp Pro Ser Arg Val Gly
1               5

<210> SEQ ID NO 33
<211> LENGTH: 8
<212> TYPE: PRT
<213> ORGANISM: Artificial Sequence
<220> FEATURE:
<223> OTHER INFORMATION: Peptide capable of binding to streptavidin or
      the modified streptavidin called streptactin

<400> SEQUENCE: 33

Trp Ser His Pro Gln Phe Glu Lys
1               5

<210> SEQ ID NO 34
<211> LENGTH: 6
<212> TYPE: PRT
<213> ORGANISM: Artificial Sequence
<220> FEATURE:
<223> OTHER INFORMATION: Tetracysteine tag that can be recognized by
      FlAsH and ReAsH biarsenical compounds

<400> SEQUENCE: 34

Cys Cys Pro Gly Cys Cys
1               5

<210> SEQ ID NO 35
<211> LENGTH: 14
<212> TYPE: PRT
<213> ORGANISM: Artificial Sequence
<220> FEATURE:
<223> OTHER INFORMATION: Peptide being recognizable by a specific
      antibody

<400> SEQUENCE: 35

Gly Lys Pro Ile Pro Asn Pro Leu Leu Gly Leu Asp Ser Thr
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Peptide being recognizable by a specific
      antibody

<400> SEQUENCE: 36

Tyr Thr Asp Ile Glu Met Asn Arg Leu Gly Lys
1               5                   10

<210> SEQ ID NO 37
<211> LENGTH: 8
<212> TYPE: PRT
<213> ORGANISM: Artificial Sequence
```

```
<220> FEATURE:
<223> OTHER INFORMATION: Peptide epitope derived from bacteriophage T7
      gene 10, recognizable by a specific antibody

<400> SEQUENCE: 37

Asp Leu Tyr Asp Asp Asp Asp Lys
1               5

<210> SEQ ID NO 38
<211> LENGTH: 16
<212> TYPE: PRT
<213> ORGANISM: Artificial Sequence
<220> FEATURE:
<223> OTHER INFORMATION: Peptide which can covalently bind to the pilin-
      C protein

<400> SEQUENCE: 38

Thr Asp Lys Asp Met Thr Ile Thr Phe Thr Asn Lys Lys Asp Ala Glu
1               5                   10                  15

<210> SEQ ID NO 39
<211> LENGTH: 13
<212> TYPE: PRT
<213> ORGANISM: Artificial Sequence
<220> FEATURE:
<223> OTHER INFORMATION: Peptide which can covalently bind to the
      SpyCatcher protein.

<400> SEQUENCE: 39

Ala His Ile Val Met Val Asp Ala Tyr Lys Pro Thr Lys
1               5                   10

<210> SEQ ID NO 40
<211> LENGTH: 19
<212> TYPE: PRT
<213> ORGANISM: Artificial Sequence
<220> FEATURE:
<223> OTHER INFORMATION: Preferred version of a poly Histidine-tag

<400> SEQUENCE: 40

Met Gly Ser Ser His His His His His His Ser Ser Gly Leu Val Pro
1               5                   10                  15

Arg Gly Ser

<210> SEQ ID NO 41
<211> LENGTH: 351
<212> TYPE: PRT
<213> ORGANISM: Artificial Sequence
<220> FEATURE:
<223> OTHER INFORMATION: Fusion protein comprising an N-terminal
      His-tag, the coiled-coil domain TDoT, a factor Xa cleavage site,
      the 3 x GGGS-linker, and the A. thaliana HNL domain

<400> SEQUENCE: 41

Met Gly Ser Ser His His His His His His Ser Ser Gly Leu Val Pro
1               5                   10                  15

Arg Gly Ser His Met Ile Ile Asn Glu Thr Ala Asp Asp Ile Val Tyr
                20                  25                  30

Arg Leu Thr Val Ile Ile Asp Asp Arg Tyr Glu Ser Leu Lys Asn Leu
            35                  40                  45

Ile Thr Leu Arg Ala Asp Arg Leu Glu Met Ile Ile Asn Asp Asn Val
    50                  55                  60

Ser Thr Ile Leu Ala Ser Ile Thr Ser Ile Glu Gly Arg Ala Ser Gly
65                  70                  75                  80
```

```
Gly Gly Ser Gly Gly Ser Gly Gly Ser Gly Ser Met Glu Arg
                85                  90                  95
Lys His His Phe Val Leu Val His Asn Ala Tyr His Gly Ala Trp Ile
            100                 105                 110
Trp Tyr Lys Leu Lys Pro Leu Leu Glu Ser Ala Gly His Arg Val Thr
        115                 120                 125
Ala Val Glu Leu Ala Ala Ser Gly Ile Asp Pro Arg Pro Ile Gln Ala
    130                 135                 140
Val Glu Thr Val Asp Glu Tyr Ser Lys Pro Leu Ile Glu Thr Leu Lys
145                 150                 155                 160
Ser Leu Pro Glu Asn Glu Glu Val Ile Leu Val Gly Phe Ser Phe Gly
                165                 170                 175
Gly Ile Asn Ile Ala Leu Ala Ala Asp Ile Phe Pro Ala Lys Ile Lys
            180                 185                 190
Val Leu Val Phe Leu Asn Ala Phe Leu Pro Asp Thr Thr His Val Pro
        195                 200                 205
Ser His Val Leu Asp Lys Tyr Met Glu Met Pro Gly Gly Leu Gly Asp
    210                 215                 220
Cys Glu Phe Ser Ser His Glu Thr Arg Asn Gly Thr Met Ser Leu Leu
225                 230                 235                 240
Lys Met Gly Pro Lys Phe Met Lys Ala Arg Leu Tyr Gln Asn Cys Pro
                245                 250                 255
Ile Glu Asp Tyr Glu Leu Ala Lys Met Leu His Arg Gln Gly Ser Phe
            260                 265                 270
Phe Thr Glu Asp Leu Ser Lys Lys Glu Lys Phe Ser Glu Glu Gly Tyr
        275                 280                 285
Gly Ser Val Gln Arg Val Tyr Val Met Ser Ser Glu Asp Lys Ala Ile
    290                 295                 300
Pro Cys Asp Phe Ile Arg Trp Met Ile Asp Asn Phe Asn Val Ser Lys
305                 310                 315                 320
Val Tyr Glu Ile Asp Gly Gly Asp His Met Val Met Leu Ser Lys Pro
                325                 330                 335
Gln Lys Leu Phe Asp Ser Leu Ser Ala Ile Ala Thr Asp Tyr Met
            340                 345                 350

<210> SEQ ID NO 42
<211> LENGTH: 1056
<212> TYPE: DNA
<213> ORGANISM: Artificial Sequence
<220> FEATURE:
<223> OTHER INFORMATION: Nucleotide sequence encoding a fusion protein
      comprising an N-terminal His-tag, the coiled-coil domain TDoT, a
      factor Xa cleavage site, the 3 x GGGS-linker, and the A. thaliana
      HNL domain

<400> SEQUENCE: 42
atgggcagca gccatcatca tcatcatcac agcagcggcc tggtgccgcg cggcagccat      60
atgatcatta cgaaactgcc gatgacatc gtttatcgcc tgacagtcat tatcgatgat     120
cgctacgaat cgctgaaaaa cctgattacc ttacgtgcag atcgcttgga gatgatcatc     180
aatgacaatg tgtccaccat tctcgcgagc attactagta ttgaaggccg tgctagcggc     240
ggtgggtctg gaggcggctc aggtggtggg tcgggatcca tggagaggaa acatcacttc     300
gtgttagttc acaacgctta tcatggagcc tggatctggt acaagctcaa gcccctcctt     360
gaatcagccg gccaccgcgt tactgctgtc gaactcgccg cctccgggat cgacccacga     420
ccaatccagg ccgttgaaac cgtcgacgaa tactccaaac cgttgatcga aaccctcaaa     480
```

```
tctcttccag agaacgaaga ggtaattctg gttggattca gcttcggagg catcaacatc    540
gctctcgccg ccgacatatt tccggcgaag attaaggttc ttgtgttcct caacgccttc    600
ttgcccgaca caacccacgt gccttctcac gttctggaca agtatatgga gatgcctgga    660
ggtttgggag attgtgagtt ttcatctcat gaaacaagaa atgggacgat gagtttattg    720
aagatgggac caaaattcat gaaggcacgt ctttaccaaa attgtcccat agaggattac    780
gagctggcaa aaatgttgca taggcaaggg tcattttca cagaggatct atcaaagaaa    840
gaaaagttta gcgaggaagg atatggttcg gtgcaacgag tttacgtaat gagtagtgaa    900
gacaaagcca tccctgcga tttcattcgt tggatgattg ataatttcaa cgtctcgaaa    960
gtctacgaga tcgatggcgg agatcacatg gtgatgctct ccaaacccca aaaactcttt   1020
gactctctct ctgctattgc caccgattat atgtaa                             1056
```

<210> SEQ ID NO 43
<211> LENGTH: 335
<212> TYPE: PRT
<213> ORGANISM: Artificial Sequence
<220> FEATURE:
<223> OTHER INFORMATION: Fusion protein comprising an N-terminal
      His-tag, the coiled-coil domain TDoT, a factor Xa cleavage site,
      the EL-linker, and the A. thaliana HNL domain

<400> SEQUENCE: 43

```
Met Gly Ser Ser His His His His His His Ser Ser Gly Leu Val Pro
1               5                   10                  15

Arg Gly Ser His Met Ile Ile Asn Glu Thr Ala Asp Asp Ile Val Tyr
            20                  25                  30

Arg Leu Thr Val Ile Ile Asp Asp Arg Tyr Glu Ser Leu Lys Asn Leu
        35                  40                  45

Ile Thr Leu Arg Ala Asp Arg Leu Glu Met Ile Ile Asn Asp Asn Val
    50                  55                  60

Ser Thr Ile Leu Ala Ser Ile Ile Glu Gly Arg Glu Leu Met Glu Arg
65                  70                  75                  80

Lys His His Phe Val Leu Val His Asn Ala Tyr His Gly Ala Trp Ile
                85                  90                  95

Trp Tyr Lys Leu Lys Pro Leu Leu Glu Ser Ala Gly His Arg Val Thr
            100                 105                 110

Ala Val Glu Leu Ala Ala Ser Gly Ile Asp Pro Arg Pro Ile Gln Ala
        115                 120                 125

Val Glu Thr Val Asp Glu Tyr Ser Lys Pro Leu Ile Glu Thr Leu Lys
    130                 135                 140

Ser Leu Pro Glu Asn Glu Glu Val Ile Leu Val Gly Phe Ser Phe Gly
145                 150                 155                 160

Gly Ile Asn Ile Ala Leu Ala Ala Asp Ile Phe Pro Ala Lys Ile Lys
                165                 170                 175

Val Leu Val Phe Leu Asn Ala Phe Leu Pro Asp Thr Thr His Val Pro
            180                 185                 190

Ser His Val Leu Asp Lys Tyr Met Glu Met Pro Gly Gly Leu Gly Asp
        195                 200                 205

Cys Glu Phe Ser Ser His Glu Thr Arg Asn Gly Thr Met Ser Leu Leu
    210                 215                 220

Lys Met Gly Pro Lys Phe Met Lys Ala Arg Leu Tyr Gln Asn Cys Pro
225                 230                 235                 240

Ile Glu Asp Tyr Glu Leu Ala Lys Met Leu His Arg Gln Gly Ser Phe
                245                 250                 255
```

```
Phe Thr Glu Asp Leu Ser Lys Lys Glu Lys Phe Ser Glu Glu Gly Tyr
                260                 265                 270

Gly Ser Val Gln Arg Val Tyr Val Met Ser Ser Glu Asp Lys Ala Ile
            275                 280                 285

Pro Cys Asp Phe Ile Arg Trp Met Ile Asp Asn Phe Asn Val Ser Lys
        290                 295                 300

Val Tyr Glu Ile Asp Gly Gly Asp His Met Val Met Leu Ser Lys Pro
305                 310                 315                 320

Gln Lys Leu Phe Asp Ser Leu Ser Ala Ile Ala Thr Asp Tyr Met
                325                 330                 335

<210> SEQ ID NO 44
<211> LENGTH: 1008
<212> TYPE: DNA
<213> ORGANISM: Artificial Sequence
<220> FEATURE:
<223> OTHER INFORMATION: Nucleotide sequence encoding a fusion protein
      comprising an N-terminal His-tag, the coiled-coil domain TDoT, a
      factor Xa cleavage site, the EL-linker, and the A. thaliana HNL
      domain

<400> SEQUENCE: 44
atgggcagca gccatcatca tcatcatcac agcagcggcc tggtgccgcg cggcagccat      60
atgattatca cgaaactgcg cgatgacatt gtgtaccgct taaccgtcat tatcgatgat    120
cgctatgaat cgctgaaaaa cctgattacg ttgcgtgcag atcgtctgga gatgatcatc    180
aatgacaatg ttagcaccat tctcgcgagt atcattgaag ccgcgagct catggagagg    240 aaacatcact tcgtgttagt tcacaacgct atcatggag cctggatctg gtacaagctc     300
aagcccctcc ttgaatcagc cggccaccgc gttactgctg tcgaactcgc cgcctccggg    360
atcgacccac gaccaatcca ggccgttgaa accgtcgacg aatactccaa accgttgatc    420 gaaacccctca atctcttcc agagaacgaa gaggtaattc tggttggatt cagcttcgga    480
ggcatcaaca tcgctctcgc cgccgacata tttccggcga agattaaggt tcttgtgttc    540
ctcaacgcct tcttgcccga cacaacccac gtgccttctc acgttctgga caagtatatg    600
gagatgcctg gagggtttgggg agattgtgag ttttcatctc atgaaacaag aaatgggacg    660
atgagtttat tgaagatggg accaaaattc atgaaggcac gtctttacca aaattgtccc    720
atagaggatt acgagctggc aaaaatgttg cataggcaag ggtcatttttt cacagaggat    780 ctatcaaaga agaaaaagtt tagcgaggaa ggatatggtt cggtgcaacg agtttacgta    840
atgagtagtg aagacaaagc catcccctgc gatttcattc gttggatgat tgataatttc    900
aacgtctcga aagtctacga gatcgatggc ggagatcaca tggtgatgct ctccaaaccc    960
caaaaactct tgactctctc tctgctatt gccaccgatt atatgtaa              1008

<210> SEQ ID NO 45
<211> LENGTH: 273
<212> TYPE: PRT
<213> ORGANISM: Artificial Sequence
<220> FEATURE:
<223> OTHER INFORMATION: Fusion protein comprising an N-terminal
      His-tag, the coiled-coil domain TDoT, a factor Xa cleavage site,
      the 3 x GGGS-linker, and the B. subtilis lipase A domain

<400> SEQUENCE: 45

Met Gly Ser Ser His His His His His His Ser Ser Gly Leu Val Pro
1               5                   10                  15

Arg Gly Ser His Met Ile Ile Asn Glu Thr Ala Asp Asp Ile Val Tyr
                20                  25                  30
```

```
Arg Leu Thr Val Ile Ile Asp Asp Arg Tyr Glu Ser Leu Lys Asn Leu
             35                  40                  45

Ile Thr Leu Arg Ala Asp Arg Leu Glu Met Ile Ile Asn Asp Asn Val
 50                  55                  60

Ser Thr Ile Leu Ala Ser Ile Thr Ser Ile Glu Gly Arg Ala Ser Gly
 65                  70                  75                  80

Gly Gly Ser Gly Gly Gly Ser Gly Gly Gly Ser Gly Ser Ala Glu His
                 85                  90                  95

Asn Pro Val Val Met Val His Gly Ile Gly Ala Ser Phe Asn Phe
                100                 105                 110

Ala Gly Ile Lys Ser Tyr Leu Val Ser Gln Gly Trp Ser Arg Asp Lys
                115                 120                 125

Leu Tyr Ala Val Asp Phe Trp Asp Lys Thr Gly Thr Asn Tyr Asn Asn
            130                 135                 140

Gly Pro Val Leu Ser Arg Phe Val Gln Lys Val Leu Asp Glu Thr Gly
145                 150                 155                 160

Ala Lys Lys Val Asp Ile Val Ala His Ser Met Gly Gly Ala Asn Thr
                165                 170                 175

Leu Tyr Tyr Ile Lys Asn Leu Asp Gly Gly Asn Lys Val Ala Asn Val
            180                 185                 190

Val Thr Leu Gly Gly Ala Asn Arg Leu Thr Thr Gly Lys Ala Leu Pro
        195                 200                 205

Gly Thr Asp Pro Asn Gln Lys Ile Leu Tyr Thr Ser Ile Tyr Ser Ser
            210                 215                 220

Ala Asp Met Ile Val Met Asn Tyr Leu Ser Arg Leu Asp Gly Ala Arg
225                 230                 235                 240

Asn Val Gln Ile His Gly Val Gly His Ile Gly Leu Leu Tyr Ser Ser
                245                 250                 255

Gln Val Asn Ser Leu Ile Lys Glu Gly Leu Asn Gly Gly Gln Asn
            260                 265                 270

Thr
```

<210> SEQ ID NO 46
<211> LENGTH: 822
<212> TYPE: DNA
<213> ORGANISM: Artificial Sequence
<220> FEATURE:
<223> OTHER INFORMATION: Nucleotide sequence encoding a fusion protein comprising an N-terminal His-tag, the coiled-coil domain TDoT, a factor Xa cleavage site, the 3 x GGGS-linker, and the B. subtilis lipase A domain

<400> SEQUENCE: 46

```
atgggcagca gccatcatca tcatcatcac agcagcggcc tggtgccgcg cggcagccat      60
atgatcatta cgaaactgc cgatgacatc gtttatcgcc tgacagtcat tatcgatgat     120
cgctacgaat cgctgaaaaa cctgattacc ttacgtgcag atcgcttgga gatgatcatc     180
aatgacaatg tgtccaccat tctcgcgagc attactagta ttgaaggccg tgctagcggc     240
ggtgggtctg gaggcggctc aggtggtggg tcgggatccg ctgaacacaa tccagtcgtt     300
atggttcacg gtattggagg gcatcattc aattttgcgg gaattaagag ctatctcgta     360
tctcagggct ggtcgcggga caagctgtat gcagttgatt tttgggacaa gacaggcaca     420
aattataaca atggaccggt attatcacga tttgtgcaaa aggttttaga tgaaacgggt     480
gcgaaaaaag tggatattgt cgctcacagc atgggggcg cgaacacact ttactacata     540
aaaaatctgg acggcggaaa taagttgca aacgtcgtga cgcttggcgg cgcgaaccgt     600
```

```
ttgacgacag gcaaggcgct tccgggaaca gatccaaatc aaaagatttt atacacatcc    660
atttacagca gtgccgatat gattgtcatg aattacttat caagattaga tggtgctaga    720
aacgttcaaa tccatggcgt tggacacatc ggccttctgt acagcagcca agtcaacagc    780
ctgattaaag aagggctgaa cggcgggggc cagaatacgt ag                       822
```

<210> SEQ ID NO 47
<211> LENGTH: 649
<212> TYPE: PRT
<213> ORGANISM: Artificial Sequence
<220> FEATURE:
<223> OTHER INFORMATION: Fusion protein comprising an N-terminal
      His-tag, the coiled-coil domain TDoT, a factor Xa cleavage site,
      the 3 x GGGS-linker, and the E.coli 2-succinyl-5-enolpyruvyl-6-
      hydroxy-3-cyclohexene-1-carboxylase

<400> SEQUENCE: 47

```
Met Gly Ser Ser His His His His His His Ser Ser Gly Leu Val Pro
1               5                   10                  15

Arg Gly Ser His Met Ile Ile Asn Glu Thr Ala Asp Asp Ile Val Tyr
            20                  25                  30

Arg Leu Thr Val Ile Ile Asp Asp Arg Tyr Glu Ser Leu Lys Asn Leu
        35                  40                  45

Ile Thr Leu Arg Ala Asp Arg Leu Glu Met Ile Ile Asn Asp Asn Val
    50                  55                  60

Ser Thr Ile Leu Ala Ser Ile Thr Ser Ile Glu Gly Arg Ala Ser Gly
65                  70                  75                  80

Gly Gly Ser Gly Gly Gly Ser Gly Gly Gly Ser Gly Ser Met Ser Val
                85                  90                  95

Ser Ala Phe Asn Arg Arg Trp Ala Ala Val Ile Leu Glu Ala Leu Thr
            100                 105                 110

Arg His Gly Val Arg His Ile Cys Ile Ala Pro Gly Ser Arg Ser Thr
        115                 120                 125

Pro Leu Thr Leu Ala Ala Ala Glu Asn Ser Ala Phe Ile His His Thr
    130                 135                 140

His Phe Asp Glu Arg Gly Leu Gly His Leu Ala Leu Gly Leu Ala Lys
145                 150                 155                 160

Val Ser Lys Gln Pro Val Ala Val Ile Val Thr Ser Gly Thr Ala Val
                165                 170                 175

Ala Asn Leu Tyr Pro Ala Leu Ile Glu Ala Gly Leu Thr Gly Glu Lys
            180                 185                 190

Leu Ile Leu Leu Thr Ala Asp Arg Pro Pro Glu Leu Ile Asp Cys Gly
        195                 200                 205

Ala Asn Gln Ala Ile Arg Gln Pro Gly Met Phe Ala Ser His Pro Thr
    210                 215                 220

His Ser Ile Ser Leu Pro Arg Pro Thr Gln Asp Ile Pro Ala Arg Trp
225                 230                 235                 240

Leu Val Ser Thr Ile Asp His Ala Leu Gly Thr Leu His Ala Gly Gly
                245                 250                 255

Val His Ile Asn Cys Pro Phe Ala Glu Pro Leu Tyr Gly Glu Met Asp
            260                 265                 270

Asp Thr Gly Leu Ser Trp Gln Gln Arg Leu Gly Asp Trp Trp Gln Asp
        275                 280                 285

Asp Lys Pro Trp Leu Arg Glu Ala Pro Arg Leu Glu Ser Glu Lys Gln
    290                 295                 300
```

```
Arg Asp Trp Phe Phe Trp Arg Gln Lys Arg Gly Val Val Ala Gly
305                 310                 315                 320

Arg Met Ser Ala Glu Glu Gly Lys Lys Val Ala Leu Trp Ala Gln Thr
            325                 330                 335

Leu Gly Trp Pro Leu Ile Gly Asp Val Leu Ser Gln Thr Gly Gln Pro
            340                 345                 350

Leu Pro Cys Ala Asp Leu Trp Leu Gly Asn Ala Lys Ala Thr Ser Glu
            355                 360                 365

Leu Gln Gln Ala Gln Ile Val Gln Leu Gly Ser Ser Leu Thr Gly
370                 375                 380

Lys Arg Leu Leu Gln Trp Gln Ala Ser Cys Glu Pro Glu Glu Tyr Trp
385                 390                 395                 400

Ile Val Asp Asp Ile Glu Gly Arg Leu Asp Pro Ala His His Arg Gly
                405                 410                 415

Arg Arg Leu Ile Ala Asn Ile Ala Asp Trp Leu Glu Leu His Pro Ala
            420                 425                 430

Glu Lys Arg Gln Pro Trp Cys Val Glu Ile Pro Arg Leu Ala Glu Gln
            435                 440                 445

Ala Met Gln Ala Val Ile Ala Arg Arg Asp Ala Phe Gly Glu Ala Gln
450                 455                 460

Leu Ala His Arg Ile Cys Asp Tyr Leu Pro Glu Gln Gly Gln Leu Phe
465                 470                 475                 480

Val Gly Asn Ser Leu Val Val Arg Leu Ile Asp Ala Leu Ser Gln Leu
                485                 490                 495

Pro Ala Gly Tyr Pro Val Tyr Ser Asn Arg Gly Ala Ser Gly Ile Asp
            500                 505                 510

Gly Leu Leu Ser Thr Ala Ala Gly Val Gln Arg Ala Ser Gly Lys Pro
            515                 520                 525

Thr Leu Ala Ile Val Gly Asp Leu Ser Ala Leu Tyr Asp Leu Asn Ala
530                 535                 540

Leu Ala Leu Leu Arg Gln Val Ser Ala Pro Leu Val Leu Ile Val Val
545                 550                 555                 560

Asn Asn Asn Gly Gly Gln Ile Phe Ser Leu Leu Pro Thr Pro Gln Ser
                565                 570                 575

Glu Arg Glu Arg Phe Tyr Leu Met Pro Gln Asn Val His Phe Glu His
            580                 585                 590

Ala Ala Ala Met Phe Glu Leu Lys Tyr His Arg Pro Gln Asn Trp Gln
            595                 600                 605

Glu Leu Glu Thr Ala Phe Ala Asp Ala Trp Arg Thr Pro Thr Thr Thr
610                 615                 620

Val Ile Glu Met Val Val Asn Asp Thr Asp Gly Ala Gln Thr Leu Gln
625                 630                 635                 640

Gln Leu Leu Ala Gln Val Ser His Leu
                645
```

<210> SEQ ID NO 48
<211> LENGTH: 1950
<212> TYPE: DNA
<213> ORGANISM: Artificial Sequence
<220> FEATURE:
<223> OTHER INFORMATION: Nucleotide sequence encoding a fusion protein comprising an N-terminal His-tag, the coiled-coil domain TDoT, a factor Xa cleavage site, the 3 x GGGS-linker, and the E.coli 2-succinyl-5-enolpyruvyl-6-hydroxy-3-cyclohexene-1-carboxylase

<400> SEQUENCE: 48

```
atgggcagca gccatcatca tcatcatcac agcagcggcc tggtgccgcg cggcagccat    60
atgatcatta acgaaactgc cgatgacatc gtttatcgcc tgacagtcat tatcgatgat   120
cgctacgaat cgctgaaaaa cctgattacc ttacgtgcag atcgcttgga gatgatcatc   180
aatgacaatg tgtccaccat tctcgcgagc attactagta ttgaaggccg tgctagcggc   240
ggtgggtctg gaggcggctc aggtggtggg tcgggatcca tgtcagtaag cgcatttaac   300
cgacgctggg cggcggtcat tctggaagca ttaacgcgtc acggcgtcag acacatctgt   360
atcgccccag gctcgcgttc tacaccgtta acgttagcgg cggcggagaa ttccgcattc   420
attcaccaca cccatttcga tgagcgtggg ttggggcatc tggcgctggg gctggcgaaa   480
gtcagcaagc agccggtggc ggtgattgtg acctccggca cggcggtggc aaatctctat   540
ccggcactga ttgaagccgg gttaaccgga gaaaaactga ttctcttaac cgccgatcgc   600
ccgccggagc taattgactg cggcgcgaat caggcaattc gccagccggg aatgttcgcc   660
tctcacccca cgcacagtat ttcattgccg cgcccgaccc aggatatccc cgcacgttgg   720
ctggtttcta ccatcgacca cgctctcggt acgcttcatg cgggggggagt ccatatcaac   780
tgcccgtttg ctgaaccgct gtatggcgaa atggacgata ccgggcttag ctggcaacag   840
cgtctgggtg actggtggca ggacgacaaa ccgtggctgc gtgaagcgcc tcgtctggaa   900
agtgaaaaac agcgcgactg gttcttctgg cgacaaaagc gcggcgtggt ggttgccggg   960
cgcatgagtg cggaagaggg caaaaaagtt gccctgtggg cgcaaactct tggctggccg  1020
ctgattggcg atgtgctgtc acaaaccggg cagccgctgc cgtgtgccga tctttggtta  1080
ggcaatgcca aagcgaccag cgagctgcag caggcgcaaa ttgtggtgca actgggaagc  1140
agcctgacgg ggaaacggct cctgcaatgg caggcaagct gtgaaccaga agagtactgg  1200
attgttgatg acattgaagg cgacttgat ccggcacacc atcgcggacg tcgcttaatt  1260
gccaatattg ccgactggct ggagctgcat ccggcagaaa acgccagcc ctggtgcgtt  1320
gaaatcccgc gcctggcgga acaggcaatg caggcggtta ttgcccgccg tgatgcgttt  1380
ggcgaagcgc aactggcgca tcgcatctgc gactatctgc tgaacagggg caattgttt  1440
gttggtaaca gcctggtggt acgtctgatt gatgcgcttt cgcaacttcc ggcaggttac  1500
ccggtgtaca gcaaccgtgg ggccagcggt atcgacgggc tgctttcgac cgccgccggc  1560
gttcagcggg caagcggcaa accgacgctg gcgattgtgg gcgatctctc cgcactttac  1620
gatctcaacg cgctggcgtt attgcgtcag gtttctgcgc cgctggtatt aattgtggtg  1680
aacaacaacg gcgggcaaat tttctcgctg ttgccaacgc cgcaaagcga gcgtgagcgt  1740
ttctatctga tgccgcaaaa cgtccatttt gagcacgccg ccgcgatgtt cgagctgaaa  1800
tatcatcgtc cgcaaaactg gcaggaactt gaaacggcat tgccgacgc ctggcgcacg  1860
ccaaccacca cggtgattga atggtggtt aacgacaccg atggtgcgca aacgctccag  1920
caacttctgg cgcaggtaag ccatttatga                                   1950
```

<210> SEQ ID NO 49
<211> LENGTH: 472
<212> TYPE: PRT
<213> ORGANISM: Artificial Sequence
<220> FEATURE:
<223> OTHER INFORMATION: Fusion protein comprising an N-terminal
His-tag, the coiled-coil domain 3HAMP, a factor Xa cleavage site,
the 3 x GGGS-linker, and the A. thaliana HNL domain

<400> SEQUENCE: 49

Met Gly Ser Ser His His His His His His Ser Gly Leu Val Pro
1               5                   10                  15

Arg Gly Ser His Met Gly Leu Phe Asn Ala His Ala Val Ala Gln Gln
            20                  25                  30

Arg Ala Asp Arg Ile Ala Thr Leu Leu Gln Ser Phe Ala Asp Gly Gln
        35                  40                  45

Leu Asp Thr Ala Val Gly Glu Ala Pro Ala Pro Gly Tyr Glu Arg Leu
    50                  55                  60

Tyr Asp Ser Leu Arg Ala Leu Gln Arg Gln Leu Arg Glu Gln Arg Ala
65                  70                  75                  80

Glu Leu Gln Gln Val Glu Ser Leu Glu Ala Gly Leu Ala Glu Met Ser
                85                  90                  95

Arg Gln His Glu Ala Gly Trp Ile Asp Gln Thr Ile Pro Ala Glu Arg
            100                 105                 110

Leu Glu Gly Arg Ala Ala Arg Ile Ala Lys Gly Val Asn Glu Leu Val
        115                 120                 125

Ala Ala His Ile Ala Val Lys Met Lys Val Val Ser Val Val Thr Ala
    130                 135                 140

Tyr Gly Gln Gly Asn Phe Glu Pro Leu Met Asp Arg Leu Pro Gly Lys
145                 150                 155                 160

Lys Ala Gln Ile Thr Glu Ala Ile Asp Gly Val Arg Glu Arg Leu Arg
                165                 170                 175

Gly Ala Ala Glu Ala Thr Ser Ala Gln Leu Ala Thr Ala Ala Tyr Asn
            180                 185                 190

Thr Ser Ile Glu Gly Arg Ala Ser Gly Gly Ser Gly Gly Gly Ser
        195                 200                 205

Gly Gly Gly Ser Gly Ser Met Glu Arg Lys His His Phe Val Leu Val
    210                 215                 220

His Asn Ala Tyr His Gly Ala Trp Ile Trp Tyr Lys Leu Lys Pro Leu
225                 230                 235                 240

Leu Glu Ser Ala Gly His Arg Val Thr Ala Val Glu Leu Ala Ala Ser
                245                 250                 255

Gly Ile Asp Pro Arg Pro Ile Gln Ala Val Glu Thr Val Asp Glu Tyr
            260                 265                 270

Ser Lys Pro Leu Ile Glu Thr Leu Lys Ser Leu Pro Glu Asn Glu Glu
        275                 280                 285

Val Ile Leu Val Gly Phe Ser Phe Gly Gly Ile Asn Ile Ala Leu Ala
    290                 295                 300

Ala Asp Ile Phe Pro Ala Lys Ile Lys Val Leu Val Phe Leu Asn Ala
305                 310                 315                 320

Phe Leu Pro Asp Thr Thr His Val Pro Ser His Val Leu Asp Lys Tyr
                325                 330                 335

Met Glu Met Pro Gly Gly Leu Gly Asp Cys Glu Phe Ser Ser His Glu
            340                 345                 350

Thr Arg Asn Gly Thr Met Ser Leu Leu Lys Met Gly Pro Lys Phe Met
        355                 360                 365

Lys Ala Arg Leu Tyr Gln Asn Cys Pro Ile Glu Asp Tyr Glu Leu Ala
    370                 375                 380

Lys Met Leu His Arg Gln Gly Ser Phe Phe Thr Glu Asp Leu Ser Lys
385                 390                 395                 400

Lys Glu Lys Phe Ser Glu Glu Gly Tyr Gly Ser Val Gln Arg Val Tyr
                405                 410                 415

Val Met Ser Ser Glu Asp Lys Ala Ile Pro Cys Asp Phe Ile Arg Trp
            420                 425                 430

Met Ile Asp Asn Phe Asn Val Ser Lys Val Tyr Glu Ile Asp Gly Gly
            435                 440                 445

Asp His Met Val Met Leu Ser Lys Pro Gln Lys Leu Phe Asp Ser Leu
            450                 455                 460

Ser Ala Ile Ala Thr Asp Tyr Met
465                 470

<210> SEQ ID NO 50
<211> LENGTH: 1419
<212> TYPE: DNA
<213> ORGANISM: Artificial Sequence
<220> FEATURE:
<223> OTHER INFORMATION: Nucleotide sequence encoding a fusion protein
      comprising an N-terminal His-tag, the coiled-coil domain 3HAMP, a
      factor Xa cleavage site, the 3 x GGGS-linker, and the A. thaliana
      HNL domain

<400> SEQUENCE: 50
atgggcagca gccatcatca tcatcatcac agcagcggcc tggtgccgcg cggcagccat      60
atgggcctgt ttaacgccca tgcagttgcg cagcaacgcg cggatcgcat tgcgactctc     120
ctgcagtcct ttgcggatgg tcagttggac accgccgtgg gtgaagcgcc agcacctggt     180
tacgaacgcc tgtatgactc gcttcgcgcc cttcagcgcc aactgcgcga caacgtgcg      240 gagttacaac aggttgagag cctggaagca ggcttggctg aaatgagtcg gcagcatgaa     300
gcagggtgga ttgaccagac gattccggct gaacggttag agggccgtgc agcacgtatc     360
gccaaaggcg tgaatgagct ggttgctgcg cacattgcgg tgaaaatgaa agtcgtgagc     420
gtagtcaccg cgtatggcca agggaacttc gaaccgctca tggatcgcct gccgggtaag     480
aaagcccaga tcacggaggc cattgatggc gtacgtgaac gcctgcgtgg agctgctgaa     540
gcgacctctg cgcagctggc cacagccgcc tacaatacta gtatcgaagg acgtgctagc     600
ggtggtggga gtggcggtgg ttcgggaggc ggctcaggat ccatggagag gaaacatcac     660
ttcgtgttag ttcacaacgc ttatcatgga gcctggatct ggtacaagct caagcccctc     720
cttgaatcag ccgccaccg cgttactgct gtcgaactcg ccgcctccgg gatcgaccca     780
cgaccaatcc aggccgttga accgtcgac gaatactcca aaccgttgat cgaaaccctc     840
aaatctcttc cagagaacga agaggtaatt ctggttggat tcagcttcgg aggcatcaac     900
atcgctctcg ccgccgacat atttccggcg aagattaagg ttcttgtgtt cctcaacgcc     960
ttcttgcccg acacaacccca cgtgccttct cacgttctgg acaagtatat ggagatgcct    1020
ggaggtttgg gagattgtga gttttcatct catgaaacaa gaatgggac gatgagttta     1080 ttgaagatgg gaccaaaatt catgaaggca cgtctttacc aaaattgtcc catagaggat    1140
tacgagctgg caaaaatgtt gcataggcaa gggtcatttt tcacagagga tctatcaaag    1200
aaagaaaagt ttagcgagga aggatatggt tcggtgcaac gagtttacgt aatgagtagt    1260
gaagacaaag ccatcccctg cgatttcatt cgttggatga ttgataattt caacgtctcg    1320
aaagtctacg agatcgatgg cggagatcac atggtgatgc tctccaaacc ccaaaaactc    1380
tttgactctc tctctgctat tgctaccgat tatatgtaa                           1419

<210> SEQ ID NO 51
<211> LENGTH: 394
<212> TYPE: PRT
<213> ORGANISM: Artificial Sequence
<220> FEATURE:
<223> OTHER INFORMATION: Fusion protein comprising an N-terminal
      His-tag, the coiled-coil domain 3HAMP, a factor Xa cleavage site,
      the 3 x GGGS-linker, and the B. subtilis lipase A domain

<400> SEQUENCE: 51

```
Met Gly Ser Ser His His His His His His Ser Ser Gly Leu Val Pro
1               5                   10                  15

Arg Gly Ser His Met Gly Leu Phe Asn Ala His Ala Val Ala Gln Gln
            20                  25                  30

Arg Ala Asp Arg Ile Ala Thr Leu Leu Gln Ser Phe Ala Asp Gly Gln
        35                  40                  45

Leu Asp Thr Ala Val Gly Glu Ala Pro Ala Pro Gly Tyr Glu Arg Leu
    50                  55                  60

Tyr Asp Ser Leu Arg Ala Leu Gln Arg Gln Leu Arg Glu Gln Arg Ala
65                  70                  75                  80

Glu Leu Gln Gln Val Glu Ser Leu Glu Ala Gly Leu Ala Glu Met Ser
                85                  90                  95

Arg Gln His Glu Ala Gly Trp Ile Asp Gln Thr Ile Pro Ala Glu Arg
            100                 105                 110

Leu Glu Gly Arg Ala Ala Arg Ile Ala Lys Gly Val Asn Glu Leu Val
        115                 120                 125

Ala Ala His Ile Ala Val Lys Met Lys Val Val Ser Val Val Thr Ala
    130                 135                 140

Tyr Gly Gln Gly Asn Phe Glu Pro Leu Met Asp Arg Leu Pro Gly Lys
145                 150                 155                 160

Lys Ala Gln Ile Thr Glu Ala Ile Asp Gly Val Arg Glu Arg Leu Arg
                165                 170                 175

Gly Ala Ala Glu Ala Thr Ser Ala Gln Leu Ala Thr Ala Ala Tyr Asn
            180                 185                 190

Thr Ser Ile Glu Gly Arg Ala Ser Gly Gly Ser Gly Gly Gly Ser
        195                 200                 205

Gly Gly Gly Ser Gly Ser Ala Glu His Asn Pro Val Val Met Val His
    210                 215                 220

Gly Ile Gly Gly Ala Ser Phe Asn Phe Ala Gly Ile Lys Ser Tyr Leu
225                 230                 235                 240

Val Ser Gln Gly Trp Ser Arg Asp Lys Leu Tyr Ala Val Asp Phe Trp
                245                 250                 255

Asp Lys Thr Gly Thr Asn Tyr Asn Asn Gly Pro Val Leu Ser Arg Phe
            260                 265                 270

Val Gln Lys Val Leu Asp Glu Thr Gly Ala Lys Lys Val Asp Ile Val
        275                 280                 285

Ala His Ser Met Gly Gly Ala Asn Thr Leu Tyr Tyr Ile Lys Asn Leu
    290                 295                 300

Asp Gly Gly Asn Lys Val Ala Asn Val Val Thr Leu Gly Gly Ala Asn
305                 310                 315                 320

Arg Leu Thr Thr Gly Lys Ala Leu Pro Gly Thr Asp Pro Asn Gln Lys
                325                 330                 335

Ile Leu Tyr Thr Ser Ile Tyr Ser Ser Ala Asp Met Ile Val Met Asn
            340                 345                 350

Tyr Leu Ser Arg Leu Asp Gly Ala Arg Asn Val Gln Ile His Gly Val
        355                 360                 365
```

Gly His Ile Gly Leu Leu Tyr Ser Ser Gln Val Asn Ser Leu Ile Lys
    370                 375                 380

Glu Gly Leu Asn Gly Gly Gly Gln Asn Thr
385                 390

<210> SEQ ID NO 52
<211> LENGTH: 1185
<212> TYPE: DNA
<213> ORGANISM: Artificial Sequence
<220> FEATURE:
<223> OTHER INFORMATION: CNucleotide sequence encoding a fusion protein
      comprising an N-terminal His-tag, the coiled-coil domain 3HAMP, a
      factor Xa cleavage site, the 3 x GGGS-linker, and the B. subtilis
      lipase A domain

<400> SEQUENCE: 52
atgggcagca gccatcatca tcatcatcac agcagcggcc tggtgccgcg cggcagccat      60
atgggcctgt ttaacgccca tgcagttgcg cagcaacgcg cggatcgcat tgcgactctc     120
ctgcagtcct tgcggatgg tcagttggac accgccgtgg gtgaagcgcc agcacctggt      180
tacgaacgcc tgtatgactc gcttcgcgcc cttcagcgcc aactgcgcga caacgtgcg     240 gagttacaac aggttgagag cctggaagca ggcttggctg aaatgagtcg gcagcatgaa     300
gcagggtgga ttgaccagac gattccggct gaacggttag agggccgtgc agcacgtatc     360
gccaaaggcg tgaatgagct ggttgctgcg cacattgcgg tgaaaatgaa agtcgtgagc     420
gtagtcaccg cgtatggcca agggaacttc gaaccgctca tggatcgcct gccgggtaag     480
aaagcccaga tcacggaggc cattgatggc gtacgtgaac gcctgcgtgg agctgctgaa     540
gcgacctctg cgcagctggc cacagccgcc tacaatacta gtatcgaagg acgtgctagc     600
ggtggtggga gtggcggtgg ttcgggaggc ggctcaggat ccgctgaaca caatccagtc     660
gttatggttc acggtattgg aggggcatca ttcaattttg cgggaattaa gagctatctc     720
gtatctcagg gctggtcgcg ggacaagctg tatgcagttg atttttggga caagacaggc     780
acaaattata caatggacc ggtattatca cgatttgtgc aaaaggtttt agatgaaacg      840
ggtgcgaaaa aagtggatat tgtcgctcac agcatggggg gcgcgaacac actttactac     900
ataaaaaatc tggacggcgg aaataaagtt gcaaacgtcg tgacgcttgg cggcgcgaac     960
cgtttgacga caggcaaggc gcttccggga acagatccaa atcaaaagat tttatacaca    1020
tccatttaca gcagtgccga tatgattgtc atgaattact tatcaagatt agatggtgct    1080
agaaacgttc aaatccatgg cgttggacac atcggccttc tgtacagcag ccaagtcaac    1140
agcctgatta agaagggct gaacggcggg ggccagaata cgtag                    1185

<210> SEQ ID NO 53
<211> LENGTH: 257
<212> TYPE: PRT
<213> ORGANISM: Artificial Sequence
<220> FEATURE:
<223> OTHER INFORMATION: Fusion protein comprising an N-terminal
      His-tag, the coiled-coil domain GCN4-p1, a factor Xa cleavage
      site, the 3 x GGGS-linker, and the B. subtilis lipase A domain

<400> SEQUENCE: 53

Met Gly Ser Ser His His His His His His Ser Ser Gly Leu Val Pro
1               5                   10                  15

Arg Gly Ser His Met Arg Met Lys Gln Leu Glu Asp Lys Val Glu Glu
            20                  25                  30

Leu Leu Ser Lys Asn Tyr His Leu Glu Asn Glu Val Ala Arg Leu Lys
        35                  40                  45

Lys Leu Val Gly Glu Arg Gly Thr Ser Ile Glu Gly Arg Ala Ser Gly
    50                  55                  60

Gly Gly Ser Gly Gly Gly Ser Gly Gly Gly Ser Gly Ser Ala Glu His
65                  70                  75                  80

Asn Pro Val Val Met Val His Gly Ile Gly Gly Ala Ser Phe Asn Phe
                85                  90                  95

Ala Gly Ile Lys Ser Tyr Leu Val Ser Gln Gly Trp Ser Arg Asp Lys
            100                 105                 110

Leu Tyr Ala Val Asp Phe Trp Asp Lys Thr Gly Thr Asn Tyr Asn Asn
            115                 120                 125

Gly Pro Val Leu Ser Arg Phe Val Gln Lys Val Leu Asp Glu Thr Gly
130                 135                 140

Ala Lys Lys Val Asp Ile Val Ala His Ser Met Gly Gly Ala Asn Thr
145                 150                 155                 160

Leu Tyr Tyr Ile Lys Asn Leu Asp Gly Gly Asn Lys Val Ala Asn Val
                165                 170                 175

Val Thr Leu Gly Gly Ala Asn Arg Leu Thr Thr Gly Lys Ala Leu Pro
            180                 185                 190

Gly Thr Asp Pro Asn Gln Lys Ile Leu Tyr Thr Ser Ile Tyr Ser Ser
            195                 200                 205

Ala Asp Met Ile Val Met Asn Tyr Leu Ser Arg Leu Asp Gly Ala Arg
            210                 215                 220

Asn Val Gln Ile His Gly Val Gly His Ile Gly Leu Leu Tyr Ser Ser
225                 230                 235                 240

Gln Val Asn Ser Leu Ile Lys Glu Gly Leu Asn Gly Gly Gly Gln Asn
            245                 250                 255

Thr

<210> SEQ ID NO 54
<211> LENGTH: 774
<212> TYPE: DNA
<213> ORGANISM: Artificial Sequence
<220> FEATURE:
<223> OTHER INFORMATION: Nucleotide sequence encoding afusion protein
      comprising an N-terminal His-tag, the coiled-coil domain GCN4-p1,
      a factor Xa cleavage site, the 3 x GGGS-linker, and the B.
      subtilis lipase A domain

<400> SEQUENCE: 54
atgggcagca gccatcatca tcatcatcac agcagcggcc tggtgccgcg cggcagccat    60
atgcggatga gcagttaga ggataaagtg aagagttac tcagcaagaa ctatcatctc    120
gagaatgagg ttgctcgctt gaagaaactg gtaggtgaac gtggtactag tatcgaagga    180
cgtgctagcg gtggtgggag tggcggtggt tcgggaggcg gctcaggatc cgctgaacac    240
aatccagtcg ttatggttca cggtattgga ggggcatcat tcaattttgc gggaattaag    300
agctatctcg tatctcaggg ctggtcgcgg gacaagctgt atgcagttga ttttgggac    360 aagacaggca caaattataa caatggaccg gtattatcac gatttgtgca aaaggtttta    420
gatgaaacgg gtgcgaaaaa agtggatatt gtcgctcaca gcatgggggg cgcgaacaca    480
ctttactaca taaaaaatct ggacggcgga aataaagttg caacgtcgt gacgcttggc    540 ggcgcgaacc gtttgacgac aggcaaggcg cttccgggaa cagatccaaa tcaaaagatt    600
ttatacacat ccatttacag cagtgccgat atgattgtca tgaattactt atcaagatta    660
gatggtgcta gaaacgttca aatccatggc gttggacaca tcggccttct gtacagcagc    720
caagtcaaca gcctgattaa agaagggctg aacggcgggg ccagaatac gtag    774

<210> SEQ ID NO 55
<211> LENGTH: 257
<212> TYPE: PRT
<213> ORGANISM: Artificial Sequence
<220> FEATURE:
<223> OTHER INFORMATION: Fusion protein comprising an N-terminal
His-tag, the coiled-coil domain GCN4-pLI, a factor Xa cleavage
site, the 3 x GGGS-linker, and the B. subtilis lipase A domain

<400> SEQUENCE: 55

```
Met Gly Ser Ser His His His His His His Ser Ser Gly Leu Val Pro
1               5                   10                  15

Arg Gly Ser His Met Arg Met Lys Gln Ile Glu Asp Lys Leu Glu Glu
            20                  25                  30

Ile Leu Ser Lys Leu Tyr His Ile Glu Asn Glu Leu Ala Arg Ile Lys
        35                  40                  45

Lys Leu Leu Gly Glu Arg Gly Thr Ser Ile Glu Gly Arg Ala Ser Gly
50                  55                  60

Gly Gly Ser Gly Gly Gly Ser Gly Gly Gly Ser Gly Ser Ala Glu His
65                  70                  75                  80

Asn Pro Val Val Met Val His Gly Ile Gly Gly Ala Ser Phe Asn Phe
                85                  90                  95

Ala Gly Ile Lys Ser Tyr Leu Val Ser Gln Gly Trp Ser Arg Asp Lys
            100                 105                 110

Leu Tyr Ala Val Asp Phe Trp Asp Lys Thr Gly Thr Asn Tyr Asn Asn
        115                 120                 125

Gly Pro Val Leu Ser Arg Phe Val Gln Lys Val Leu Asp Glu Thr Gly
130                 135                 140

Ala Lys Lys Val Asp Ile Val Ala His Ser Met Gly Gly Ala Asn Thr
145                 150                 155                 160

Leu Tyr Tyr Ile Lys Asn Leu Asp Gly Gly Asn Lys Val Ala Asn Val
                165                 170                 175

Val Thr Leu Gly Gly Ala Asn Arg Leu Thr Thr Gly Lys Ala Leu Pro
            180                 185                 190

Gly Thr Asp Pro Asn Gln Lys Ile Leu Tyr Thr Ser Ile Tyr Ser Ser
        195                 200                 205

Ala Asp Met Ile Val Met Asn Tyr Leu Ser Arg Leu Asp Gly Ala Arg
210                 215                 220

Asn Val Gln Ile His Gly Val Gly His Ile Gly Leu Leu Tyr Ser Ser
225                 230                 235                 240

Gln Val Asn Ser Leu Ile Lys Glu Gly Leu Asn Gly Gly Gln Asn
                245                 250                 255

Thr
```

<210> SEQ ID NO 56
<211> LENGTH: 774
<212> TYPE: DNA
<213> ORGANISM: Artificial Sequence
<220> FEATURE:
<223> OTHER INFORMATION: Nucleotide sequence encoding a fusion protein
comprising an N-terminal His-tag, the coiled-coil domain GCN4-pLI,
a factor Xa cleavage site, the 3 x GGGS-linker, and the B.
subtilis lipase A domain

<400> SEQUENCE: 56
atgggcagca gccatcatca tcatcatcac agcagcggcc tggtgccgcg cggcagccat      60
atgcgcatga acagattga ggataaactg gaagaaatcc tgagcaaact ctatcatatc      120
gagaacgaat tagcgcgcat taagaaactg ttgggtgaac gtggcactag tatcgaagga     180

-continued

```
cgtgctagcg gtggtgggag tggcggtggt tcgggaggcg gctcaggatc cgctgaacac    240
aatccagtcg ttatggttca cggtattgga ggggcatcat tcaattttgc gggaattaag    300
agctatctcg tatctcaggg ctggtcgcgg gacaagctgt atgcagttga tttttgggac    360
aagacaggca caaattataa caatggaccg gtattatcac gatttgtgca aaaggtttta    420
gatgaaacgg gtgcgaaaaa agtggatatt gtcgctcaca gcatgggggg cgcgaacaca    480
ctttactaca taaaaaatct ggacggcgga aataaagttg caaacgtcgt gacgcttggc    540
ggcgcgaacc gtttgacgac aggcaaggcg cttccgggaa cagatccaaa tcaaaagatt    600
ttatacacat ccatttacag cagtgccgat atgattgtca tgaattactt atcaagatta    660
gatggtgcta gaaacgttca aatccatggc gttggacaca tcggccttct gtacagcagc    720
caagtcaaca gcctgattaa agaagggctg aacggcgggg gccagaatac gtag          774
```

<210> SEQ ID NO 57
<211> LENGTH: 34
<212> TYPE: DNA
<213> ORGANISM: Artificial Sequence
<220> FEATURE:
<223> OTHER INFORMATION: Forward primer for amplification of athnl, providing BamHI restriction close to the 5' end of the amplification product; for cloning of pTDoT-Linker-AtHNL

<400> SEQUENCE: 57

```
atatatggat ccatggagag gaaacatcac ttcg                                 34
```

<210> SEQ ID NO 58
<211> LENGTH: 37
<212> TYPE: DNA
<213> ORGANISM: Artificial Sequence
<220> FEATURE:
<223> OTHER INFORMATION: Reverse primer for amplification of athnl providing NotI restriction site close to 3' end of the amplification product; for cloning of pTDoT-Linker-AtHNL

<400> SEQUENCE: 58

```
atatatgcgg ccgcttacat ataatcggtg gcaatag                              37
```

<210> SEQ ID NO 59
<211> LENGTH: 36
<212> TYPE: DNA
<213> ORGANISM: Artificial Sequence
<220> FEATURE:
<223> OTHER INFORMATION: Forward primer for amplification of bsla providing BamHI restriction close to the 5' end of the amplification product; for cloning of pTDoT-Linker-BsLA

<400> SEQUENCE: 59

```
atatatggat ccgctgaaca caatccagtc gttatg                               36
```

<210> SEQ ID NO 60
<211> LENGTH: 27
<212> TYPE: DNA
<213> ORGANISM: Artificial Sequence
<220> FEATURE:
<223> OTHER INFORMATION: Reverse primer for amplification of bsla providing NotI restriction site close to 3' end of the amplification product; for cloning of pTDoT-Linker-BsLA

<400> SEQUENCE: 60

```
ctcgagtgcg gccgcaagct tgtcgac                                         27
```

```
<210> SEQ ID NO 61
<211> LENGTH: 33
<212> TYPE: DNA
<213> ORGANISM: Artificial Sequence
<220> FEATURE:
<223> OTHER INFORMATION: Forward primer for amplification of ecmend
      providing BamHI restriction close to the 5' end of the
      amplification product; for cloning of pTDoT-Linker-EcMenD

<400> SEQUENCE: 61
atatatggat ccatgtcagt aagcgcattt aac                                    33

<210> SEQ ID NO 62
<211> LENGTH: 32
<212> TYPE: DNA
<213> ORGANISM: Artificial Sequence
<220> FEATURE:
<223> OTHER INFORMATION: Reverse primer for amplification of ecmend
      providing SalI restriction close to the 3' end of the
      amplification product; for cloning of pTDoT-Linker-EcMenD

<400> SEQUENCE: 62
atatatgtcg actcataaat ggcttacctg cg                                     32

<210> SEQ ID NO 63
<211> LENGTH: 23
<212> TYPE: DNA
<213> ORGANISM: Artificial Sequence
<220> FEATURE:
<223> OTHER INFORMATION: Forward primer for generating a PCR product
      comprising NdeI/SpeI overlaps; for cloning control constructs
      lacking tdot

<400> SEQUENCE: 63
tatgactagt attgaaggcc gtg                                               23

<210> SEQ ID NO 64
<211> LENGTH: 25
<212> TYPE: DNA
<213> ORGANISM: Artificial Sequence
<220> FEATURE:
<223> OTHER INFORMATION: Reverse primer for generating a PCR product
      comprising NdeI/SpeI overlaps; for cloning control constructs
      lacking tdot

<400> SEQUENCE: 64
ctagcacggc cttcaatact agtca                                             25

<210> SEQ ID NO 65
<211> LENGTH: 36
<212> TYPE: DNA
<213> ORGANISM: Artificial Sequence
<220> FEATURE:
<223> OTHER INFORMATION: Forward primer for PCR amplification of a
      fragment of the B. subtilis Lipase A gene, provides a BamH1
      restriction site to the 5' end of the amplification product

<400> SEQUENCE: 65
atatatggat ccgctgaaca caatccagtc gttatg                                 36

<210> SEQ ID NO 66
<211> LENGTH: 27
<212> TYPE: DNA
<213> ORGANISM: Artificial Sequence
<220> FEATURE:
<223> OTHER INFORMATION: Reverse Primer for amplification of the B.
      subtilis Lipase A gene present in pET28; provides Sal1 and Not1
      restriction sites to the 3' end of the amplification product
```

-continued

```
<400> SEQUENCE: 66
ctcgagtgcg gccgcaagct tgtcgac                                        27

<210> SEQ ID NO 67
<211> LENGTH: 34
<212> TYPE: DNA
<213> ORGANISM: Artificial Sequence
<220> FEATURE:
<223> OTHER INFORMATION: Forward primer for amplificatin of the A.
      thaliana HNL gene; provides a BamHI restriction site at the 5'
      end of the amplification product

<400> SEQUENCE: 67
atatatggat ccatggagag gaaacatcac ttcg                                34

<210> SEQ ID NO 68
<211> LENGTH: 37
<212> TYPE: DNA
<213> ORGANISM: Artificial Sequence
<220> FEATURE:
<223> OTHER INFORMATION: Reverse primer for amplification of the A.
      thaliana HNL gene

<400> SEQUENCE: 68
atatatgcgg ccgcttacat ataatcggtg gcaatag                             37

<210> SEQ ID NO 69
<211> LENGTH: 7
<212> TYPE: PRT
<213> ORGANISM: Artificial Sequence
<220> FEATURE:
<223> OTHER INFORMATION: Peptide comprising cleavage site for Tobacco
      Etch Virus protease

<400> SEQUENCE: 69

Glu Asn Leu Tyr Phe Gln Ser
1               5

<210> SEQ ID NO 70
<211> LENGTH: 6
<212> TYPE: PRT
<213> ORGANISM: Artificial Sequence
<220> FEATURE:
<223> OTHER INFORMATION: Peptide comprising cleavage site for thrombin.

<400> SEQUENCE: 70

Leu Val Pro Arg Gly Ser
1               5

<210> SEQ ID NO 71
<211> LENGTH: 4
<212> TYPE: PRT
<213> ORGANISM: Artificial Sequence
<220> FEATURE:
<223> OTHER INFORMATION: Peptide comprising cleavage site for Factor Xa

<400> SEQUENCE: 71

Ile Glu Gly Arg
1

<210> SEQ ID NO 72
<211> LENGTH: 4
<212> TYPE: PRT
<213> ORGANISM: Artificial Sequence
<220> FEATURE:
<223> OTHER INFORMATION: Peptide comprising cleavage site for Factor Xa
```

```
<400> SEQUENCE: 72

Ile Asp Gly Arg
1

<210> SEQ ID NO 73
<211> LENGTH: 5
<212> TYPE: PRT
<213> ORGANISM: Artificial Sequence
<220> FEATURE:
<223> OTHER INFORMATION: Peptide comprising cleavage site for
      enteropeptidase

<400> SEQUENCE: 73

Asp Asp Asp Asp Lys
1               5

<210> SEQ ID NO 74
<211> LENGTH: 345
<212> TYPE: PRT
<213> ORGANISM: Bacillus thuringiensis

<400> SEQUENCE: 74

Met Lys Ala Val Val Asn Lys Asn Ser Lys Ala Asn Ile Glu Val
1               5                   10                  15

Ile Glu Lys Glu Leu Arg Pro Leu Arg Ser Gly Glu Ala Leu Val Asp
                20                  25                  30

Val Glu Tyr Cys Gly Val Cys His Thr Asp Leu His Val Ala Asn His
            35                  40                  45

Asp Phe Gly Asn Thr Asp Gly Arg Ile Leu Gly His Glu Gly Val Gly
        50                  55                  60

Ile Val Thr Lys Ile Ala Asp Asp Val Asn Ser Leu Lys Ile Gly Asp
65                  70                  75                  80

Arg Val Ser Ile Ala Trp Met Phe Gln Ser Cys Gly Arg Cys Glu Tyr
                85                  90                  95

Cys Val Thr Gly Arg Glu Thr Phe Cys Arg Glu Val Lys Asn Ala Gly
            100                 105                 110

Tyr Ser Val Asp Gly Gly Met Ala Glu Gln Cys Ile Val Thr Ala Asp
        115                 120                 125

Tyr Ala Val Lys Val Pro Glu Gly Leu Asp Pro Ala Gln Ala Ser Ser
    130                 135                 140

Ile Thr Cys Ala Gly Val Thr Thr Tyr Lys Ala Ile Lys Val Ser Asp
145                 150                 155                 160

Ile Lys Pro Gly Gln Pro Ile Val Ile Tyr Gly Cys Gly Gly Leu Gly
                165                 170                 175

Asn Leu Ala Ile Gln Tyr Ala Lys Asn Val Phe Gly Ala Lys Val Ile
            180                 185                 190

Ala Val Asp Ile Asn Asp Asp Lys Leu Ala Leu Ala Lys Glu Val Gly
        195                 200                 205

Ala Asp Met Thr Ile Asn Pro Ile Ser Gln Gly Pro Ala Asp Lys Ile
    210                 215                 220

Val Gln Glu Glu Leu Gly Gly Ala Tyr Ala Ala Val Thr Ala Val
225                 230                 235                 240

Ser Lys Val Ala Phe Asn Ser Ala Val Asp Ala Val Arg Ala Cys Gly
                245                 250                 255

Lys Val Val Ala Val Gly Leu Pro Val Glu Thr Met Asp Leu Asn Ile
            260                 265                 270
```

```
Pro Arg Leu Val Leu Asp Gly Ile Glu Val Val Gly Ser Leu Val Gly
            275                 280                 285

Thr Arg Lys Asp Leu Glu Glu Ala Phe Met Phe Gly Ala Glu Gly Lys
        290                 295                 300

Val Val Pro Val Val Gln Thr Cys Ser Leu Asp Lys Val Gln Asn Val
305                 310                 315                 320

Phe Glu Glu Met Glu Gln Gly Arg Ile Gln Gly Arg Met Val Ile Asp
                325                 330                 335

Phe Lys Gln His Asn Cys Asp Cys Lys
            340                 345

<210> SEQ ID NO 75
<211> LENGTH: 1038
<212> TYPE: DNA
<213> ORGANISM: Bacillus thuringiensis

<400> SEQUENCE: 75
atgaaagcag tagtagttaa taaaaatagt aaagcaaaca tcgaagtgat tgaaaagaa      60 ttacgtccgt tacgctcagg cgaagcgtta gtagatgtag agtattgtgg agtttgccac    120
actgatttac acgttgcgaa tcatgatttt ggtaacactg atggccgtat tcttggtcat    180
gagggtgtag gtattgttac gaaaatagct gatgatgtta attcgctaaa gataggtgac    240
cgtgtaagta ttcatggat gttccaatct tgtggacgtt gtgaatattg cgtaactggt    300
agagaaacat tttgccgtga agttaaaaac gcaggttatt cagtagatgg tggtatggct    360
gaacaatgta tcgttacagc tgattatgcg gtaaaagtac cagaaggatt agatcctgct    420
caagcatcat caattacatg tgctggtgta actacatata aagctattaa agtatcagat    480
attaaacctg gtcaacctat tgtaatctat ggctgcggtg gattaggtaa cttagctatc    540
caatatgcta aaaatgtatt tggtgcaaag gtaatcgcag tagacattaa tgacgacaaa    600
ttagccttag cgaaagaagt tggtgctgat atgactatca atccaatatc tcaaggtcct    660
gctgataaaa ttgttcaaga ggagcttggt ggcgcttatg ctgcggtagt aacagcagtc    720
tctaaagtag cctttaactc agcagttgat gcagtacgtg cttgcggtaa agtagttgca    780
gtagggctac cagtagaaac aatggactta aacatcccgc gacttgtact ggatggaatt    840
gaagtagttg gttctctagt gggtactcgt aaagatttgg aagaggcgtt tatgtttggg    900
gcagaaggaa agtagtgcc ggttgttcaa acttgttcgc tagataaagt acaaaatgta    960
ttcgaagaaa tggaacaagg tagaattcaa gggcgtatgg taattgattt taaacagcat   1020
aattgtgatt gcaaataa                                                 1038

<210> SEQ ID NO 76
<211> LENGTH: 438
<212> TYPE: PRT
<213> ORGANISM: artificial sequence
<220> FEATURE:
<223> OTHER INFORMATION: Fusion protein comprising an N-terminal
      His-tag, the coiled-coil domain TDoT, a factor Xa cleavage site,
      the 3 x GGGS-linker, and the Bacillus thuringiensis BtADH domain

<400> SEQUENCE: 76

Met Gly Ser Ser His His His His His His Ser Ser Gly Leu Val Pro
1               5                   10                  15

Arg Gly Ser His Met Ile Ile Asn Glu Thr Ala Asp Asp Ile Val Tyr
            20                  25                  30

Arg Leu Thr Val Ile Ile Asp Asp Arg Tyr Glu Ser Leu Lys Asn Leu
        35                  40                  45
```

```
Ile Thr Leu Arg Ala Asp Arg Leu Glu Met Ile Ile Asn Asp Asn Val
     50                  55                  60

Ser Thr Ile Leu Ala Ser Ile Thr Ser Ile Glu Gly Arg Ala Ser Gly
 65                  70                  75                  80

Gly Gly Ser Gly Gly Ser Gly Gly Ser Gly Ser Met Lys Ala
                 85                  90                  95

Val Val Val Asn Lys Asn Ser Lys Ala Asn Ile Glu Val Ile Glu Lys
                100                 105                 110

Glu Leu Arg Pro Leu Arg Ser Gly Glu Ala Leu Val Asp Val Glu Tyr
            115                 120                 125

Cys Gly Val Cys His Thr Asp Leu His Val Ala Asn His Asp Phe Gly
        130                 135                 140

Asn Thr Asp Gly Arg Ile Leu Gly His Glu Gly Val Gly Ile Val Thr
145                 150                 155                 160

Lys Ile Ala Asp Asp Val Asn Ser Leu Lys Ile Gly Asp Arg Val Ser
                165                 170                 175

Ile Ala Trp Met Phe Gln Ser Cys Gly Arg Cys Glu Tyr Cys Val Thr
            180                 185                 190

Gly Arg Glu Thr Phe Cys Arg Glu Val Lys Asn Ala Gly Tyr Ser Val
        195                 200                 205

Asp Gly Gly Met Ala Glu Gln Cys Ile Val Thr Ala Asp Tyr Ala Val
    210                 215                 220

Lys Val Pro Glu Gly Leu Asp Pro Ala Gln Ala Ser Ser Ile Thr Cys
225                 230                 235                 240

Ala Gly Val Thr Thr Tyr Lys Ala Ile Lys Val Ser Asp Ile Lys Pro
                245                 250                 255

Gly Gln Pro Ile Val Ile Tyr Gly Cys Gly Gly Leu Gly Asn Leu Ala
            260                 265                 270

Ile Gln Tyr Ala Lys Asn Val Phe Gly Ala Lys Val Ile Ala Val Asp
        275                 280                 285

Ile Asn Asp Asp Lys Leu Ala Leu Ala Lys Glu Val Gly Ala Asp Met
    290                 295                 300

Thr Ile Asn Pro Ile Ser Gln Gly Pro Ala Asp Lys Ile Val Gln Glu
305                 310                 315                 320

Glu Leu Gly Gly Ala Tyr Ala Ala Val Val Thr Ala Val Ser Lys Val
                325                 330                 335

Ala Phe Asn Ser Ala Val Asp Ala Val Arg Ala Cys Gly Lys Val Val
            340                 345                 350

Ala Val Gly Leu Pro Val Glu Thr Met Asp Leu Asn Ile Pro Arg Leu
        355                 360                 365

Val Leu Asp Gly Ile Glu Val Val Gly Ser Leu Val Gly Thr Arg Lys
    370                 375                 380

Asp Leu Glu Glu Ala Phe Met Phe Gly Ala Glu Gly Lys Val Val Pro
385                 390                 395                 400

Val Val Gln Thr Cys Ser Leu Asp Lys Val Gln Asn Val Phe Glu Glu
                405                 410                 415

Met Glu Gln Gly Arg Ile Gln Gly Arg Met Val Ile Asp Phe Lys Gln
            420                 425                 430

His Asn Cys Asp Cys Lys
        435
```

-continued

<210> SEQ ID NO 77
<211> LENGTH: 1317
<212> TYPE: DNA
<213> ORGANISM: Artificial Sequence
<220> FEATURE:
<223> OTHER INFORMATION: Nucleotide Sequence encoding a fusion protein
      comprising an N-terminal His-tag, the coiled-coil domain TDoT, a
      factor Xa cleavage site, the 3 x GGGS-linker, and the Bacillus
      thuringiensis BtADH domain

<400> SEQUENCE: 77

```
atgggcagca gccatcatca tcatcatcac agcagcggcc tggtgccgcg cggcagccat     60
atgatcatta acgaaactgc cgatgacatc gtttatcgcc tgacagtcat tatcgatgat    120
cgctacgaat cgctgaaaaa cctgattacc ttacgtgcag atcgcttgga gatgatcatc    180
aatgacaatg tgtccaccat tctcgcgagc attactagta ttgaaggccg tgctagcggc    240
ggtgggtctg gaggcggctc aggtggtggg tcgggatcca tgaaagcagt agtagttaat    300
aaaaatagta aagcaaacat cgaagtgatt gaaaaagaat acgtccgtt acgctcaggc    360
gaagcgttag tagatgtaga gtattgtgga gtttgccaca ctgatttaca cgttgcgaat    420
catgattttg gtaacactga tggccgtatt cttggtcatg agggtgtagg tattgttacg    480
aaaatagctg atgatgttaa ttcgctaaag ataggtgacc gtgtaagtat tgcatggatg    540
ttccaatctt gtggacgttg tgaatattgc gtaactggta gagaaacatt ttgccgtgaa    600
gttaaaaacg caggttattc agtagatggt ggtatggctg aacaatgtat cgttacagct    660
gattatgcgg taaaagtacc agaaggatta gatcctgctc aagcatcatc aattacatgt    720
gctggtgtaa ctacatataa agctattaaa gtatcagata ttaaacctgg tcaacctatt    780
gtaatctatg gctgcggtgg attaggtaac ttagctatcc aatatgctaa aaatgtattt    840
ggtgcaaagg taatcgcagt agacattaat gacgacaaat tagccttagc gaaagaagtt    900
ggtgctgata tgactatcaa tccaatatct caaggtcctg ctgataaaat tgttcaagag    960
gagcttggtg gcgcttatgc tgcggtagta acagcagtct ctaaagtagc ctttaactca   1020
gcagttgatg cagtacgtgc ttgcggtaaa gtagttgcag tagggctacc agtagaaaca   1080
atggacttaa acatcccgcg acttgtactg gatggaattg aagtagttgg ttctctagtg   1140
ggtactcgta agatttgga agaggcgttt atgtttgggg cagaaggaaa agtagtgccg   1200
gttgttcaaa cttgttcgct agataaagta caaaatgtat tcgaagaaat ggaacaaggt   1260
agaattcaag ggcgtatggt aattgatttt aaacagcata attgtgattg caaataa     1317
```

<210> SEQ ID NO 78
<211> LENGTH: 269
<212> TYPE: PRT
<213> ORGANISM: Unknown
<220> FEATURE:
<223> OTHER INFORMATION: Cutinase enzyme from metagenomic origin

<400> SEQUENCE: 78

```
Met Val Trp Ala Ser Pro Ser Val Glu Ala Gln Ser Asn Pro Tyr Gln
1               5                   10                  15

Arg Gly Pro Asn Pro Thr Arg Ser Ala Leu Thr Ala Asp Gly Pro Phe
            20                  25                  30

Ser Val Ala Thr Tyr Thr Val Ser Arg Leu Ser Val Ser Gly Phe Gly
        35                  40                  45

Gly Gly Val Ile Tyr Tyr Pro Thr Gly Thr Ser Leu Thr Phe Gly Gly
    50                  55                  60
```

```
Ile Ala Met Ser Pro Gly Tyr Thr Ala Asp Ala Ser Ser Leu Ala Trp
 65                  70                  75                  80

Leu Gly Arg Arg Leu Ala Ser His Gly Phe Val Val Leu Val Ile Asn
                 85                  90                  95

Thr Asn Ser Arg Phe Asp Tyr Pro Asp Ser Arg Ala Ser Gln Leu Ser
            100                 105                 110

Ala Ala Leu Asn Tyr Leu Arg Thr Ser Ser Pro Ser Ala Val Arg Ala
            115                 120                 125

Arg Leu Asp Ala Asn Arg Leu Ala Val Ala Gly His Ser Met Gly Gly
        130                 135                 140

Gly Gly Thr Leu Arg Ile Ala Glu Gln Asn Pro Ser Leu Lys Ala Ala
145                 150                 155                 160

Val Pro Leu Thr Pro Trp His Thr Asp Lys Thr Phe Asn Thr Ser Val
                165                 170                 175

Pro Val Leu Ile Val Gly Ala Glu Ala Asp Thr Val Ala Pro Val Ser
            180                 185                 190

Gln His Ala Ile Pro Phe Tyr Gln Asn Leu Pro Ser Thr Thr Pro Lys
        195                 200                 205

Val Tyr Val Glu Leu Asp Asn Ala Ser His Phe Ala Pro Asn Ser Asn
210                 215                 220

Asn Ala Ala Ile Ser Val Tyr Thr Ile Ser Trp Met Lys Leu Trp Val
225                 230                 235                 240

Asp Asn Asp Thr Arg Tyr Arg Gln Phe Leu Cys Asn Val Asn Asp Pro
                245                 250                 255

Ala Leu Ser Asp Phe Arg Thr Asn Asn Arg His Cys Gln
            260                 265

<210> SEQ ID NO 79
<211> LENGTH: 810
<212> TYPE: DNA
<213> ORGANISM: Unknown
<220> FEATURE:
<223> OTHER INFORMATION: Nucleotide sequence encoding a cutinase enzyme
      from metagenomic origin

<400> SEQUENCE: 79
atggtttggg cttctccgtc tgttgaagct cagtctaacc cgtaccagcg tggtccgaac     60
ccgacccgtt ctgctctgac cgctgacggt ccgttctctg ttgctaccta caccgttcct    120
cgtctgtctg tttctggttt cggtggtggt gttatctact acccgaccgg tacctctctg    180
accttcggtg gtatcgctat gtctccgggt tacaccgctg acgcttcttc tctggcttgg    240
ctgggtcgtc gtctggcttc tcacggtttc gttgttctgg ttatcaacac caactctcgt    300
ttcgactacc cggactctcg tgcttctcag ctgtctgctg ctctgaacta cctgcgtacc    360
tcttctccgt ctgctgttcg tgctcgtctg gacgctaacc gtctggctgt tgctggtcac    420
tctatgggtg gtggtggtac cctgcgtatc gctgaacaga acccgtctct gaaagctgct    480
gttccgctga cccgtggca caccgacaaa accttcaaca cctctgttcc ggttctgatc    540
gttggtgctg aagctgacac cgttgctccg gtttctcagc acgctatccc gttctaccag    600
aacctgccgt ctaccacccc gaaagtttac gttgaactgg acaacgcttc tcacttcgct    660
ccgaactcta acaacgctgc tatctctgtt tacaccatct cttggatgaa actgtgggtt    720
gacaacgaca cccgttaccg tcagttcctg tgcaacgtta acgacccggc tctgtctgac    780
ttccgtacca caaccgtca ctgccagtga                                      810
```

<210> SEQ ID NO 80
<211> LENGTH: 362
<212> TYPE: PRT
<213> ORGANISM: artificial sequence
<220> FEATURE:
<223> OTHER INFORMATION: Fusion protein comprising an N-terminal
      His-tag, the coiled-coil domain TDoT, a factor Xa cleavage site,
      the 3 x GGGS-linker, and the LCC domain from metagenomic origin

<400> SEQUENCE: 80

```
Met Gly Ser Ser His His His His His Ser Ser Gly Leu Val Pro
1               5                   10                  15

Arg Gly Ser His Met Ile Ile Asn Glu Thr Ala Asp Ile Val Tyr
                20                  25                  30

Arg Leu Thr Val Ile Ile Asp Asp Arg Tyr Glu Ser Leu Lys Asn Leu
            35                  40                  45

Ile Thr Leu Arg Ala Asp Arg Leu Glu Met Ile Ile Asn Asp Asn Val
    50                  55                  60

Ser Thr Ile Leu Ala Ser Ile Thr Ser Ile Glu Gly Arg Ala Ser Gly
65                  70                  75                  80

Gly Gly Ser Gly Gly Gly Ser Gly Gly Gly Ser Gly Ser Met Val Trp
                85                  90                  95

Ala Ser Pro Ser Val Glu Ala Gln Ser Asn Pro Tyr Gln Arg Gly Pro
                100                 105                 110

Asn Pro Thr Arg Ser Ala Leu Thr Ala Asp Gly Pro Phe Ser Val Ala
                115                 120                 125

Thr Tyr Thr Val Ser Arg Leu Ser Val Ser Gly Phe Gly Gly Gly Val
                130                 135                 140

Ile Tyr Tyr Pro Thr Gly Thr Ser Leu Thr Phe Gly Gly Ile Ala Met
145                 150                 155                 160

Ser Pro Gly Tyr Thr Ala Asp Ala Ser Ser Leu Ala Trp Leu Gly Arg
                165                 170                 175

Arg Leu Ala Ser His Gly Phe Val Val Leu Val Ile Asn Thr Asn Ser
                180                 185                 190

Arg Phe Asp Tyr Pro Asp Ser Arg Ala Ser Gln Leu Ser Ala Ala Leu
                195                 200                 205

Asn Tyr Leu Arg Thr Ser Ser Pro Ser Ala Val Arg Ala Arg Leu Asp
                210                 215                 220

Ala Asn Arg Leu Ala Val Ala Gly His Ser Met Gly Gly Gly Gly Thr
225                 230                 235                 240

Leu Arg Ile Ala Glu Gln Asn Pro Ser Leu Lys Ala Ala Val Pro Leu
                245                 250                 255

Thr Pro Trp His Thr Asp Lys Thr Phe Asn Thr Ser Val Pro Val Leu
                260                 265                 270

Ile Val Gly Ala Glu Ala Asp Thr Val Ala Pro Val Ser Gln His Ala
                275                 280                 285

Ile Pro Phe Tyr Gln Asn Leu Pro Ser Thr Thr Pro Lys Val Tyr Val
                290                 295                 300

Glu Leu Asp Asn Ala Ser His Phe Ala Pro Asn Ser Asn Asn Ala Ala
305                 310                 315                 320

Ile Ser Val Tyr Thr Ile Ser Trp Met Lys Leu Trp Val Asp Asn Asp
                325                 330                 335

Thr Arg Tyr Arg Gln Phe Leu Cys Asn Val Asn Asp Pro Ala Leu Ser
                340                 345                 350

Asp Phe Arg Thr Asn Asn Arg His Cys Gln
                355                 360
```

<210> SEQ ID NO 81
<211> LENGTH: 1089
<212> TYPE: DNA
<213> ORGANISM: artificial sequence
<220> FEATURE:
<223> OTHER INFORMATION: Nucleotide Sequence encoding a fusion protein comprising an N-terminal His-tag, the coiled-coil domain TDoT, a factor Xa cleavage site, the 3 x GGGS-linker, and the LCC domain from metagenomic origin

<400> SEQUENCE: 81

```
atgggcagca gccatcatca tcatcatcac agcagcggcc tggtgccgcg cggcagccat    60
atgatcatta acgaaactgc cgatgacatc gtttatcgcc tgacagtcat tatcgatgat   120
cgctacgaat cgctgaaaaa cctgattacc ttacgtgcag atcgcttgga gatgatcatc   180
aatgacaatg tgtccaccat tctcgcgagc attactagta ttgaaggccg tgctagcggc   240
ggtgggtctg gaggcggctc aggtggtggg tcgggatcca tggtttgggc ttctccgtct   300
gttgaagctc agtctaaccc gtaccagcgt ggtccgaacc cgacccgttc tgctctgacc   360
gctgacggtc cgttctctgt tgctacctac accgtttctc gtctgtctgt ttctggtttc   420
ggtggtggtg ttatctacta cccgaccggt acctctctga ccttcggtgg tatcgctatg   480
tctccgggtt acaccgctga cgcttcttct ctggcttggc tgggtcgtcg tctggcttct   540
cacggtttcg ttgttctggt tatcaacacc aactctcgtt tcgactaccc ggactctcgt   600
gcttctcagc tgtctgctgc tctgaactac ctgcgtacct cttctccgtc tgctgttcgt   660
gctcgtctgg acgctaaccg tctggctgtt gctggtcact ctatgggtgg tggtggtacc   720
ctgcgtatcg ctgaacagaa cccgtctctg aaagctgctg ttccgctgac cccgtggcac   780
accgacaaaa ccttcaacac ctctgttccg gttctgatcg ttggtgctga agctgacacc   840
gttgctccgg tttctcagca cgctatcccg ttctaccaga acctgccgtc taccaccccg   900
aaagtttacg ttgaactgga caacgcttct cacttcgctc cgaactctaa caacgctgct   960
atctctgttt acaccatctc tttggatgaaa ctgtgggttg acaacgacac ccgttaccgt  1020
cagttcctgt gcaacgttaa cgacccggct ctgtctgact ccgtaccaa caaccgtcac  1080
tgccagtga                                                          1089
```

<210> SEQ ID NO 82
<211> LENGTH: 563
<212> TYPE: PRT
<213> ORGANISM: Pseudomonas fluorescens

<400> SEQUENCE: 82

```
Met Ala Met Ile Thr Gly Gly Glu Leu Val Val Arg Thr Leu Ile Lys
1               5                   10                  15

Ala Gly Val Glu His Leu Phe Gly Leu His Gly Ala His Ile Asp Thr
                20                  25                  30

Ile Phe Gln Ala Cys Leu Asp His Asp Val Pro Ile Ile Asp Thr Arg
            35                  40                  45

His Glu Ala Ala Ala Gly His Ala Ala Glu Gly Tyr Ala Arg Ala Gly
        50                  55                  60

Ala Lys Leu Gly Val Ala Leu Val Thr Ala Gly Gly Gly Phe Thr Asn
65                  70                  75                  80

Ala Val Thr Pro Ile Ala Asn Ala Trp Leu Asp Arg Thr Pro Val Leu
                85                  90                  95

Phe Leu Thr Gly Ser Gly Ala Leu Arg Asp Asp Glu Thr Asn Thr Leu
            100                 105                 110
```

-continued

Gln Ala Gly Ile Asp Gln Val Ala Met Ala Ala Pro Ile Thr Lys Trp
             115                 120                 125

Ala His Arg Val Met Ala Thr Glu His Ile Pro Arg Leu Val Met Gln
130                 135                 140

Ala Ile Arg Ala Ala Leu Ser Ala Pro Arg Gly Pro Val Leu Leu Asp
145                 150                 155                 160

Leu Pro Trp Asp Ile Leu Met Asn Gln Ile Asp Glu Asp Ser Val Ile
                 165                 170                 175

Ile Pro Asp Leu Val Leu Ser Ala His Gly Ala Arg Pro Asp Pro Ala
             180                 185                 190

Asp Leu Asp Gln Ala Leu Ala Leu Leu Arg Lys Ala Glu Arg Pro Val
             195                 200                 205

Ile Val Leu Gly Ser Glu Ala Ser Arg Thr Ala Arg Lys Thr Ala Leu
210                 215                 220

Ser Ala Phe Val Ala Ala Thr Gly Val Pro Val Phe Ala Asp Tyr Glu
225                 230                 235                 240

Gly Leu Ser Met Leu Ser Gly Leu Pro Asp Ala Met Arg Gly Gly Leu
                 245                 250                 255

Val Gln Asn Leu Tyr Ser Phe Ala Lys Ala Asp Ala Ala Pro Asp Leu
             260                 265                 270

Val Leu Met Leu Gly Ala Arg Phe Gly Leu Asn Thr Gly His Gly Ser
             275                 280                 285

Gly Gln Leu Ile Pro His Ser Ala Gln Val Ile Gln Val Asp Pro Asp
290                 295                 300

Ala Cys Glu Leu Gly Arg Leu Gln Gly Ile Ala Leu Gly Ile Val Ala
305                 310                 315                 320

Asp Val Gly Gly Thr Ile Glu Ala Leu Ala Gln Ala Thr Ala Gln Asp
                 325                 330                 335

Ala Ala Trp Pro Asp Arg Gly Asp Trp Cys Ala Lys Val Thr Asp Leu
             340                 345                 350

Ala Gln Glu Arg Tyr Ala Ser Ile Ala Ala Lys Ser Ser Glu His
             355                 360                 365

Ala Leu His Pro Phe His Ala Ser Gln Val Ile Ala Lys His Val Asp
             370                 375                 380

Ala Gly Val Thr Val Val Ala Asp Gly Ala Leu Thr Tyr Leu Trp Leu
385                 390                 395                 400

Ser Glu Val Met Ser Arg Val Lys Pro Gly Gly Phe Leu Cys His Gly
                 405                 410                 415

Tyr Leu Gly Ser Met Gly Val Gly Phe Gly Thr Ala Leu Gly Ala Gln
                 420                 425                 430

Val Ala Asp Leu Glu Ala Gly Arg Arg Thr Ile Leu Val Thr Gly Asp
             435                 440                 445

Gly Ser Val Gly Tyr Ser Ile Gly Glu Phe Asp Thr Leu Val Arg Lys
450                 455                 460

Gln Leu Pro Leu Ile Val Ile Met Asn Asn Gln Ser Trp Gly Ala
465                 470                 475                 480

Thr Leu His Phe Gln Gln Leu Ala Val Gly Pro Asn Arg Val Thr Gly
                 485                 490                 495

Thr Arg Leu Glu Asn Gly Ser Tyr His Gly Val Ala Ala Phe Gly
             500                 505                 510

Ala Asp Gly Tyr His Val Asp Ser Val Glu Ser Phe Ser Ala Ala Leu
515                 520                 525

Ala Gln Ala Leu Ala His Asn Arg Pro Ala Cys Ile Asn Val Ala Val
530                 535                 540

Ala Leu Asp Pro Ile Pro Pro Glu Glu Leu Ile Leu Ile Gly Met Asp
545                 550                 555                 560

Pro Phe Ala

<210> SEQ ID NO 83
<211> LENGTH: 1692
<212> TYPE: DNA
<213> ORGANISM: Pseudomonas fluorescens

<400> SEQUENCE: 83

```
atggcgatga ttacaggcgg cgaactggtt gttcgcaccc taataaaggc tggggtcgaa    60
catctgttcg gcctgcacgg cgcgcatatc gatacgattt tccaagcctg tctcgatcat   120
gatgtgccga tcatcgacac ccgccatgag ccgccgcag gcatgcggc cgagggctat    180
gcccgcgctg cgccaagct gggcgtggcg ctggtcacgg cgggcggggg atttaccaat   240
gcggtcacgc ccattgccaa cgcttggctg atcgcacgc cggtgctctt cctcaccgga   300
tcgggcgcgc tgcgtgatga tgaaaccaac acgttgcagg cggggattga tcaggtcgcc   360
atggcggcgc ccattaccaa atgggcgcat cgggtgatgg caaccgagca tatcccacgg   420
ctggtgatgc aggcgatccg cgccgcgttg agcgcgccac gcgggccggt gttgctggat   480
ctgccgtggg atattctgat gaaccagatt gatgaggata cgtcattat ccccgatctg    540
gtcttgtccg cacatggggc cagacccgac cctgccgatc tggatcaggc tctcgcgctt   600
ttgcgcaagg cggagcggcc ggtcatcgtg ctcggctcag aagcctcgcg acagcgcgc   660
aagacggcgc ttagcgcatt cgtggcggcg actggcgtgc cggtgtttgc cgattatgaa   720
gggctaagca tgctctcggg gctgcccgat gctatgcggg cgggctggt gcaaaacctc    780
tattcttttg ccaaagccga tgccgcgcca gatctcgtgc tgatgctggg ggcgcgcttt   840
ggccttaaca ccgggcatgg atctgggcag ttgatcccc atagcgcgca ggtcattcag    900
gtcgaccctg atgcctgcga gctgggacgc ctgcaggca tcgctctggg cattgtggcc    960
gatgtgggtg ggaccatcga ggctttggcg caggccaccg cgcaagatgc ggcttggccg   1020
gatcgcggcg actggtgcgc caaagtgacg gatctggcgc aagagcgcta tgccagcatc   1080
gctgcgaaat cgagcagcga gcatgcgctc cacccctttc acgcctcgca ggtcattgcc   1140
aaacacgtcg atgcaggggt gacggtggta gcggatggtg cgctgaccta tctctggctg   1200
tccgaagtga tgagccgcgt gaaacccggc ggttttctct gccacggcta tctaggctcg   1260
atgggcgtgg gcttcggcac ggcgctgggc gcgcaagtgg ccgatcttga agcaggccgc   1320
cgcacgatcc ttgtgaccgg cgatggctcg gtgggctata gcatcggtga atttgatacg   1380
ctggtgcgca acaattgcc gctgatcgtc atcatcatga caaccaaag ctgggggggcg    1440
acattgcatt ccagcaatt ggccgtcggc cccaatcgcg tgacgggcac ccgtttggaa   1500
aatggctcct atcacggggt ggccgccgcc tttggcgcgg atggctatca tgtcgacagt   1560
gtggagagct ttctgcggc tctggcccaa gcgctcgccc ataatcgccc cgcctgcatc   1620
aatgtcgcgg tcgcgctcga tccgatcccg cccgaagaac tcattctgat cggcatggac   1680
cccttcgcat aa                                                      1692
```

<210> SEQ ID NO 84
<211> LENGTH: 636
<212> TYPE: PRT
<213> ORGANISM: artificial sequence
<220> FEATURE:
<223> OTHER INFORMATION: Fusion protein comprising the coiled-coil
domain TDoT, a factor Xa cleavage site, the 3 x GGGS-linker, and
the Pseudomonas fluorescens PfBAL domain

<400> SEQUENCE: 84

Met Ile Ile Asn Glu Thr Ala Asp Asp Ile Val Tyr Arg Leu Thr Val
1               5                   10                  15

Ile Ile Asp Asp Arg Tyr Glu Ser Leu Lys Asn Leu Ile Thr Leu Arg
            20                  25                  30

Ala Asp Arg Leu Glu Met Ile Ile Asn Asp Asn Val Ser Thr Ile Leu
        35                  40                  45

Ala Ser Ile Thr Ser Ile Glu Gly Arg Ala Ser Gly Gly Gly Ser Gly
    50                  55                  60

Gly Gly Ser Gly Gly Gly Ser Gly Ser Met Ala Met Ile Thr Gly Gly
65                  70                  75                  80

Glu Leu Val Arg Thr Leu Ile Lys Ala Gly Val Glu His Leu Phe
                85                  90                  95

Gly Leu His Gly Ala His Ile Asp Thr Ile Phe Gln Ala Cys Leu Asp
                100                 105                 110

His Asp Val Pro Ile Ile Asp Thr Arg His Glu Ala Ala Ala Gly His
                115                 120                 125

Ala Ala Glu Gly Tyr Ala Arg Ala Gly Ala Lys Leu Gly Val Ala Leu
130                 135                 140

Val Thr Ala Gly Gly Gly Phe Thr Asn Ala Val Thr Pro Ile Ala Asn
145                 150                 155                 160

Ala Trp Leu Asp Arg Thr Pro Val Leu Phe Leu Thr Gly Ser Gly Ala
                165                 170                 175

Leu Arg Asp Asp Glu Thr Asn Thr Leu Gln Ala Gly Ile Asp Gln Val
                180                 185                 190

Ala Met Ala Ala Pro Ile Thr Lys Trp Ala His Arg Val Met Ala Thr
                195                 200                 205

Glu His Ile Pro Arg Leu Val Met Gln Ala Ile Arg Ala Ala Leu Ser
                210                 215                 220

Ala Pro Arg Gly Pro Val Leu Leu Asp Leu Pro Trp Asp Ile Leu Met
225                 230                 235                 240

Asn Gln Ile Asp Glu Asp Ser Val Ile Ile Pro Asp Leu Val Leu Ser
                245                 250                 255

Ala His Gly Ala Arg Pro Asp Pro Ala Asp Leu Asp Gln Ala Leu Ala
                260                 265                 270

Leu Leu Arg Lys Ala Glu Arg Pro Val Ile Val Leu Gly Ser Glu Ala
                275                 280                 285

Ser Arg Thr Ala Arg Lys Thr Ala Leu Ser Ala Phe Val Ala Ala Thr
                290                 295                 300

Gly Val Pro Val Phe Ala Asp Tyr Glu Gly Leu Ser Met Leu Ser Gly
305                 310                 315                 320

Leu Pro Asp Ala Met Arg Gly Gly Leu Val Gln Asn Leu Tyr Ser Phe
                325                 330                 335

Ala Lys Ala Asp Ala Ala Pro Asp Leu Val Leu Met Leu Gly Ala Arg
                340                 345                 350

Phe Gly Leu Asn Thr Gly His Gly Ser Gly Gln Leu Ile Pro His Ser
                355                 360                 365

Ala Gln Val Ile Gln Val Asp Pro Asp Ala Cys Glu Leu Gly Arg Leu
                370                 375                 380

```
Gln Gly Ile Ala Leu Gly Ile Val Ala Asp Val Gly Gly Thr Ile Glu
385                 390                 395                 400

Ala Leu Ala Gln Ala Thr Ala Gln Asp Ala Ala Trp Pro Asp Arg Gly
                405                 410                 415

Asp Trp Cys Ala Lys Val Thr Asp Leu Ala Gln Glu Arg Tyr Ala Ser
            420                 425                 430

Ile Ala Ala Lys Ser Ser Glu His Ala Leu His Pro Phe His Ala
        435                 440                 445

Ser Gln Val Ile Ala Lys His Val Asp Ala Gly Val Thr Val Val Ala
    450                 455                 460

Asp Gly Ala Leu Thr Tyr Leu Trp Leu Ser Glu Val Met Ser Arg Val
465                 470                 475                 480

Lys Pro Gly Gly Phe Leu Cys His Gly Tyr Leu Gly Ser Met Gly Val
                485                 490                 495

Gly Phe Gly Thr Ala Leu Gly Ala Gln Val Ala Asp Leu Glu Ala Gly
            500                 505                 510

Arg Arg Thr Ile Leu Val Thr Gly Asp Gly Ser Val Gly Tyr Ser Ile
        515                 520                 525

Gly Glu Phe Asp Thr Leu Val Arg Lys Gln Leu Pro Leu Ile Val Ile
    530                 535                 540

Ile Met Asn Asn Gln Ser Trp Gly Ala Thr Leu His Phe Gln Gln Leu
545                 550                 555                 560

Ala Val Gly Pro Asn Arg Val Thr Gly Thr Arg Leu Glu Asn Gly Ser
                565                 570                 575

Tyr His Gly Val Ala Ala Ala Phe Gly Ala Asp Gly Tyr His Val Asp
            580                 585                 590

Ser Val Glu Ser Phe Ser Ala Ala Leu Ala Gln Ala Leu Ala His Asn
        595                 600                 605

Arg Pro Ala Cys Ile Asn Val Ala Val Ala Leu Asp Pro Ile Pro Pro
    610                 615                 620

Glu Glu Leu Ile Leu Ile Gly Met Asp Pro Phe Ala
625                 630                 635

<210> SEQ ID NO 85
<211> LENGTH: 1911
<212> TYPE: DNA
<213> ORGANISM: artificial sequence
<220> FEATURE:
<223> OTHER INFORMATION: Nucleotide Sequence encoding a fusion protein
      comprising the coiled-coil domain TDoT, a factor Xa cleavage site,
      the 3 x GGGS-linker, and the Pseudomonas fluorescens PfBAL  domain

<400> SEQUENCE: 85
atgatcatta acgaaactgc cgatgacatc gtttatcgcc tgacagtcat tatcgatgat      60
cgctacgaat cgctgaaaaa cctgattacc ttacgtgcag atcgcttgga gatgatcatc     120
aatgacaatg tgtccaccat tctcgcgagc attactagta ttgaaggccg tgctagcggc     180
ggtgggtctg gaggcggctc aggtggtggg tcgggatcca tggcgatgat tacaggcggc     240
gaactggttg ttcgcacccc taataaaggct ggggtcgaac atctgttcgg cctgcacggc     300
gcgcatatcg atacgatttt tcaagcctgt ctcgatcatg atgtgccgat catcgacacc     360
cgccatgagg ccgccgcagg gcatgcggcc gagggctatg cccgcgctgg cgccaagctg     420
ggcgtggcgc tggtcacggc gggcggggga tttaccaatg cggtcacgcc cattgccaac     480
gcttggctgg atcgcacgcc ggtgctcttc ctcaccggat cgggcgcgct gcgtgatgat     540
gaaaccaaca cgttgcaggc ggggattgat caggtcgcca tggcggcgcc cattaccaaa     600
```

```
tgggcgcatc gggtgatggc aaccgagcat atcccacggc tggtgatgca ggcgatccgc      660
gccgcgttga gcgcgccacg cgggccggtg ttgctggatc tgccgtggga tattctgatg      720
aaccagattg atgaggatag cgtcattatc cccgatctgg tcttgtccgc acatggggcc      780
agacccgacc ctgccgatct ggatcaggct ctcgcgcttt tgcgcaaggc ggagcggccg      840
gtcatcgtgc tcggctcaga agcctcgcgg acagcgcgca agacggcgct tagcgcattc      900
gtggcggcga ctggcgtgcc ggtgtttgcc gattatgaag ggctaagcat gctctcgggg      960
ctgcccgatg ctatgcgggg cgggctggtg caaaacctct attcttttgc caaagccgat     1020
gccgcgccag atctcgtgct gatgctgggg gcgcgctttg ccttaacac cgggcatgga      1080
tctgggcagt tgatccccca tagcgcgcag gtcattcagg tcgaccctga tgcctgcgag     1140
ctggacgcc tgcagggcat cgctctgggc attgtggccg atgtgggtgg gaccatcgag      1200
gctttggcgc aggccaccgc gcaagatgcg gcttggccgg atcgcggcga ctggtgcgcc     1260
aaagtgacgg atctggcgca agagcgctat gccagcatcg ctgcgaaatc gagcagcgag     1320
catgcgctcc accccttca cgcctcgcag gtcattgcca aacacgtcga tgcagggg tg     1380
acggtggtag cggatggtgc gctgacctat ctctggctgt ccgaagtgat gagccgcgtg     1440
aaaccccggcg gttttctctg ccacggctat ctaggctcga tgggcgtggg cttcggcacg     1500
gcgctgggcg cgcaagtggc cgatcttgaa gcaggccgcc gcacgatcct tgtgaccggc     1560
gatggctcgg tgggctatag catcggtgaa tttgatacgc tggtgcgcaa acaattgccg     1620
ctgatcgtca tcatcatgaa caaccaaagc tgggggcga cattgcattt ccagcaattg     1680
gccgtcggcc ccaatcgcgt gacgggcacc cgtttggaaa atggctccta tcacggggtg     1740
gccgccgcct ttggcgcgga tggctatcat gtcgacagtg tggagagctt ttctgcggct     1800
ctggcccaag cgctcgccca taatcgcccc gcctgcatca atgtcgcggt cgcgctcgat     1860
ccgatcccgc ccgaagaact cattctgatc ggcatggacc ccttcgcata a              1911
```

<210> SEQ ID NO 86
<211> LENGTH: 249
<212> TYPE: PRT
<213> ORGANISM: Ralstonia sp.

<400> SEQUENCE: 86

```
Met Tyr Arg Leu Leu Asn Lys Thr Ala Val Ile Thr Gly Gly Asn Ser
1               5                   10                  15

Gly Ile Gly Leu Ala Thr Ala Lys Arg Phe Val Ala Glu Gly Ala Tyr
            20                  25                  30

Val Phe Ile Val Gly Arg Arg Lys Glu Leu Glu Gln Ala Ala Ala
        35                  40                  45

Glu Ile Gly Arg Asn Val Thr Ala Val Lys Ala Asp Val Thr Lys Leu
    50                  55                  60

Glu Asp Leu Asp Arg Leu Tyr Ala Ile Arg Glu Gln Arg Gly Ser
65                  70                  75                  80

Ile Asp Val Leu Phe Ala Asn Ser Gly Ala Ile Glu Gln Lys Thr Leu
                85                  90                  95

Glu Glu Ile Thr Pro Glu His Tyr Asp Arg Thr Phe Asp Val Asn Val
            100                 105                 110

Arg Gly Leu Ile Phe Thr Val Gln Lys Ala Leu Pro Leu Leu Arg Asp
        115                 120                 125

Gly Gly Ser Val Ile Leu Thr Ser Ser Val Ala Gly Val Leu Gly Leu
    130                 135                 140
```

-continued

```
Gln Ala His Asp Thr Tyr Ser Ala Ala Lys Ala Val Arg Ser Leu
145                 150                 155                 160

Ala Arg Thr Trp Thr Thr Glu Leu Lys Gly Arg Ser Ile Arg Val Asn
                165                 170                 175

Ala Val Ser Pro Gly Ala Ile Asp Thr Pro Ile Ile Glu Asn Gln Val
            180                 185                 190

Ser Thr Gln Glu Glu Ala Asp Glu Leu Arg Ala Lys Phe Ala Ala Ala
        195                 200                 205

Thr Pro Leu Gly Arg Val Gly Arg Pro Glu Glu Leu Ala Ala Ala Val
    210                 215                 220

Leu Phe Leu Ala Ser Asp Asp Ser Ser Tyr Val Ala Gly Ile Glu Leu
225                 230                 235                 240

Phe Val Asp Gly Gly Leu Thr Gln Val
                245
```

<210> SEQ ID NO 87
<211> LENGTH: 750
<212> TYPE: DNA
<213> ORGANISM: Ralstonia sp.

<400> SEQUENCE: 87

```
atgtatcgtc tgctgaataa aaccgcagtt attaccggtg gtaatagcgg tattggtctg      60
gcaaccgcaa aacgttttgt tgccgaaggt gcctatgttt ttattgttgg tcgtcgtcgt     120
aaagaactgg aacaggcagc agcagaaatt ggtcgtaatg ttaccgcagt taaagccgat     180
gttaccaaac tggaagatct ggatcgtctg tatgcaattg ttcgtgaaca gcgtggtagc     240
attgatgttc tgtttgcaaa tagcggtgcc attgaacaga aaaccctgga agaaattaca     300
ccggaacatt atgatcgcac ctttgatgtt aatgtgcgtg gtctgatttt taccgttcag     360
aaagcactgc cgctgctgcg tgatggtggt agcgttattc tgaccagcag cgttgccggt     420
gttctgggtc tgcaggcaca tgataccatat agcgcagcaa aagcagcagt tcgtagcctg     480
gcacgtacct ggaccaccga actgaaaggt cgtagcattc gtgttaatgc agttagtccg     540
ggtgcaattg ataccccgat tattgaaaat caggttagca cccaggaaga agcagacgaa     600
ctgcgcgcaa aatttgcagc agcaacaccg ctgggtcgtg ttggtcgtcc ggaagaactg     660
gcagcagccg ttctgttttct ggcaagtgat gatagcagct atgttgcagg tattgaactg     720
tttgttgatg gtggtctgac ccaggtttaa                                      750
```

<210> SEQ ID NO 88
<211> LENGTH: 322
<212> TYPE: PRT
<213> ORGANISM: artificial sequence
<220> FEATURE:
<223> OTHER INFORMATION: Fusion protein comprising the coiled-coil
      domain TDoT, a factor Xa cleavage site, the 3 x GGGS-linker, and
      the Ralstonia sp. RADH domain

<400> SEQUENCE: 88

```
Met Ile Ile Asn Glu Thr Ala Asp Asp Ile Val Tyr Arg Leu Thr Val
1               5                   10                  15

Ile Ile Asp Asp Arg Tyr Glu Ser Leu Lys Asn Leu Ile Thr Leu Arg
                20                  25                  30

Ala Asp Arg Leu Glu Met Ile Ile Asn Asp Asn Val Ser Thr Ile Leu
            35                  40                  45

Ala Ser Ile Thr Ser Ile Glu Gly Arg Ala Ser Gly Gly Gly Ser Gly
        50                  55                  60
```

Gly Gly Ser Gly Gly Gly Ser Gly Ser Met Tyr Arg Leu Leu Asn Lys
65                  70                  75                  80

Thr Ala Val Ile Thr Gly Gly Asn Ser Gly Ile Gly Leu Ala Thr Ala
                85                  90                  95

Lys Arg Phe Val Ala Glu Gly Ala Tyr Val Phe Ile Val Gly Arg Arg
            100                 105                 110

Arg Lys Glu Leu Glu Gln Ala Ala Glu Ile Gly Arg Asn Val Thr
        115                 120                 125

Ala Val Lys Ala Asp Val Thr Lys Leu Glu Asp Leu Asp Arg Leu Tyr
145                 150                 155                 160

Ala Ile Val Arg Glu Gln Arg Gly Ser Ile Asp Val Leu Phe Ala Asn
145                 150                 155                 160

Ser Gly Ala Ile Glu Gln Lys Thr Leu Glu Glu Ile Thr Pro Glu His
                165                 170                 175

Tyr Asp Arg Thr Phe Asp Val Asn Val Arg Gly Leu Ile Phe Thr Val
            180                 185                 190

Gln Lys Ala Leu Pro Leu Leu Arg Asp Gly Gly Ser Val Ile Leu Thr
        195                 200                 205

Ser Ser Val Ala Gly Val Leu Gly Leu Gln Ala His Asp Thr Tyr Ser
210                 215                 220

Ala Ala Lys Ala Ala Val Arg Ser Leu Ala Arg Thr Trp Thr Thr Glu
225                 230                 235                 240

Leu Lys Gly Arg Ser Ile Arg Val Asn Ala Val Ser Pro Gly Ala Ile
                245                 250                 255

Asp Thr Pro Ile Ile Glu Asn Gln Val Ser Thr Gln Glu Glu Ala Asp
            260                 265                 270

Glu Leu Arg Ala Lys Phe Ala Ala Ala Thr Pro Leu Gly Arg Val Gly
        275                 280                 285

Arg Pro Glu Glu Leu Ala Ala Ala Val Leu Phe Leu Ala Ser Asp Asp
        290                 295                 300

Ser Ser Tyr Val Ala Gly Ile Glu Leu Phe Val Asp Gly Gly Leu Thr
305                 310                 315                 320

Gln Val

<210> SEQ ID NO 89
<211> LENGTH: 969
<212> TYPE: DNA
<213> ORGANISM: artificial sequence
<220> FEATURE:
<223> OTHER INFORMATION: Nucleotide Sequence encoding a fusion protein
      comprising the coiled-coil domain TDoT, a factor Xa cleavage site,
      the 3 x GGGS-linker, and the Ralstonia sp. RADH domain

<400> SEQUENCE: 89
atgatcatta acgaaactgc cgatgacatc gtttatcgcc tgacagtcat tatcgatgat      60
cgctacgaat cgctgaaaaa cctgattacc ttacgtgcag atcgcttgga gatgatcatc     120
aatgacaatg tgtccaccat tctcgcgagc attactagta ttgaaggccg tgctagcggc     180
ggtgggtctg gaggcggctc aggtggtggg tcgggatcca tgtatcgtct gctgaataaa     240
accgcagtta ttaccggtgg taatagcggt attggtctgg caaccgcaaa acgttttgtt     300
gccgaaggtg cctatgtttt tattgttggt cgtcgtcgta agaactgga acaggcagca     360 gcagaaattg gtcgtaatgt taccgcagtt aaagccgatg ttaccaaact ggaagatctg     420
gatcgtctgt atgcaattgt tcgtgaacag cgtggtagca ttgatgttct gtttgcaaat     480
agcggtgcca ttgaacagaa aaccctggaa gaaattacac cggaacatta tgatcgcacc     540

```
tttgatgtta atgtgcgtgg tctgattttt accgttcaga aagcactgcc gctgctgcgt      600
gatggtggta gcgttattct gaccagcagc gttgccggtg ttctgggtct gcaggcacat      660
gatacctata gcgcagcaaa agcagcagtt cgtagcctgg cacgtacctg gaccaccgaa      720
ctgaaaggtc gtagcattcg tgttaatgca gttagtccgg gtgcaattga tacccccgatt     780 attgaaaatc aggttagcac ccaggaagaa gcagacgaac tgcgcgcaaa atttgcagca      840
gcaacaccgc tgggtcgtgt tggtcgtccg gaagaactgg cagcagccgt tctgtttctg      900
gcaagtgatg atagcagcta tgttgcaggt attgaactgt tgttgatgg tggtctgacc       960 caggtttaa                                                              969
```

<210> SEQ ID NO 90
<211> LENGTH: 443
<212> TYPE: PRT
<213> ORGANISM: artificial sequence
<220> FEATURE:
<223> OTHER INFORMATION: Fusion protein comprising the coiled-coil
      domain 3HAMP, a factor Xa cleavage site, the 3 x GGGS-linker, and
      the Ralstonia sp. RADH domain

<400> SEQUENCE: 90

```
Met Gly Leu Phe Asn Ala His Ala Val Ala Gln Gln Arg Ala Asp Arg
1               5                   10                  15

Ile Ala Thr Leu Leu Gln Ser Phe Ala Asp Gly Gln Leu Asp Thr Ala
            20                  25                  30

Val Gly Glu Ala Pro Ala Pro Gly Tyr Glu Arg Leu Tyr Asp Ser Leu
        35                  40                  45

Arg Ala Leu Gln Arg Gln Leu Arg Glu Gln Arg Ala Glu Leu Gln Gln
    50                  55                  60

Val Glu Ser Leu Glu Ala Gly Leu Ala Glu Met Ser Arg Gln His Glu
65                  70                  75                  80

Ala Gly Trp Ile Asp Gln Thr Ile Pro Ala Glu Arg Leu Glu Gly Arg
                85                  90                  95

Ala Ala Arg Ile Ala Lys Gly Val Asn Glu Leu Val Ala Ala His Ile
            100                 105                 110

Ala Val Lys Met Lys Val Val Ser Val Val Thr Ala Tyr Gly Gln Gly
        115                 120                 125

Asn Phe Glu Pro Leu Met Asp Arg Leu Pro Gly Lys Lys Ala Gln Ile
    130                 135                 140

Thr Glu Ala Ile Asp Gly Val Arg Glu Arg Leu Arg Gly Ala Ala Glu
145                 150                 155                 160

Ala Thr Ser Ala Gln Leu Ala Thr Ala Ala Tyr Asn Thr Ser Ile Glu
                165                 170                 175

Gly Arg Ala Ser Gly Gly Gly Ser Gly Gly Gly Ser Gly Gly Gly Ser
            180                 185                 190

Gly Ser Met Tyr Arg Leu Leu Asn Lys Thr Ala Val Ile Thr Gly Gly
        195                 200                 205

Asn Ser Gly Ile Gly Leu Ala Thr Ala Lys Arg Phe Val Ala Glu Gly
    210                 215                 220

Ala Tyr Val Phe Ile Val Gly Arg Arg Lys Glu Leu Glu Gln Ala
225                 230                 235                 240

Ala Ala Glu Ile Gly Arg Asn Val Thr Ala Val Lys Ala Asp Val Thr
                245                 250                 255

Lys Leu Glu Asp Leu Asp Arg Leu Tyr Ala Ile Val Arg Glu Gln Arg
            260                 265                 270
```

```
Gly Ser Ile Asp Val Leu Phe Ala Asn Ser Gly Ala Ile Glu Gln Lys
            275                 280                 285

Thr Leu Glu Glu Ile Thr Pro Glu His Tyr Asp Arg Thr Phe Asp Val
        290                 295                 300

Asn Val Arg Gly Leu Ile Phe Thr Val Gln Lys Ala Leu Pro Leu Leu
305                 310                 315                 320

Arg Asp Gly Gly Ser Ile Leu Thr Ser Ser Val Ala Gly Val Leu
                325                 330                 335

Gly Leu Gln Ala His Asp Thr Tyr Ser Ala Ala Lys Ala Ala Val Arg
            340                 345                 350

Ser Leu Ala Arg Thr Trp Thr Thr Glu Leu Lys Gly Arg Ser Ile Arg
        355                 360                 365

Val Asn Ala Val Ser Pro Gly Ala Ile Asp Thr Pro Ile Ile Glu Asn
370                 375                 380

Gln Val Ser Thr Gln Glu Glu Ala Asp Glu Leu Arg Ala Lys Phe Ala
385                 390                 395                 400

Ala Ala Thr Pro Leu Gly Arg Val Gly Arg Pro Glu Glu Leu Ala Ala
                405                 410                 415

Ala Val Leu Phe Leu Ala Ser Asp Asp Ser Ser Tyr Val Ala Gly Ile
            420                 425                 430

Glu Leu Phe Val Asp Gly Gly Leu Thr Gln Val
        435                 440

<210> SEQ ID NO 91
<211> LENGTH: 1332
<212> TYPE: DNA
<213> ORGANISM: artificial sequence
<220> FEATURE:
<223> OTHER INFORMATION: Nucleotide Sequence encoding a fusion protein
      comprising the coiled-coil domain 3HAMP, a factor Xa cleavage
      site, the 3 x GGGS-linker, and the Ralstonia sp. RADH domain

<400> SEQUENCE: 91
atgggcctgt taacgccca tgcagttgcg cagcaacgcg cggatcgcat tgcgactctc      60
ctgcagtcct ttgcggatgg tcagttggac accgccgtgg gtgaagcgcc agcacctggt    120
tacgaacgcc tgtatgactc gcttcgcgcc cttcagcgcc aactgcgcga caacgtgcg     180 gagttacaac aggttgagag cctggaagca ggcttggctg aaatgagtcg gcagcatgaa    240
gcagggtgga ttgaccagac gattccggct gaacggttag agggccgtgc agcacgtatc    300
gccaaaggcg tgaatgagct ggttgctgcg cacattgcgg tgaaaatgaa agtcgtgagc    360
gtagtcaccg cgtatggcca agggaacttc gaaccgctca tggatcgcct gccgggtaag    420
aaagcccaga tcacggaggc cattgatggc gtacgtgaac gcctgcgtgg agctgctgaa    480
gcgacctctg cgcagctggc cacagccgcc tacaatacta gtattgaagg ccgtgctagc    540
ggcggtgggt ctggaggcgg ctcaggtggt gggtcgggat ccatgtatcg tctgctgaat    600
aaaaccgcag ttattaccgg tggtaatagc ggtattggtc tggcaaccgc aaaacgtttt    660
gttgccgaag gtgcctatgt ttttattgtt ggtcgtcgtc gtaaagaact ggaacaggca    720
gcagcagaaa ttggtcgtaa tgttaccgca gttaaagccg atgttaccaa actggaagat    780
ctggatcgtc tgtatgcaat tgttcgtgaa cagcgtggta gcattgatgt tctgtttgca    840
aatagcggtg ccattgaaca gaaaacccct gaagaaatta ccggaacatt atgatcgc     900 acctttgatg ttaatgtgcg tggtctgatt tttaccgttc agaaagcact gccgctgctg    960
cgtgatggtg gtagcgttat tctgaccagc agcgttgccg gtgttctggg tctgcaggca   1020
```

```
catgatacct atagcgcagc aaaagcagca gttcgtagcc tggcacgtac ctggaccacc    1080
gaactgaaag gtcgtagcat tcgtgttaat gcagttagtc cgggtgcaat tgatacccg    1140 attattgaaa atcaggttag cacccaggaa gaagcagacg aactgcgcgc aaaatttgca    1200
gcagcaacac cgctgggtcg tgttggtcgt ccggaagaac tggcagcagc cgttctgttt    1260
ctggcaagtg atgatagcag ctatgttgca ggtattgaac tgtttgttga tggtggtctg    1320
acccaggttt aa                                                        1332
```

```
<210> SEQ ID NO 92
<211> LENGTH: 38
<212> TYPE: DNA
<213> ORGANISM: artificial sequence
<220> FEATURE:
<223> OTHER INFORMATION: Forward primer for amplification of the RADH
      gene; provides a BamHI restriction site at the 5' end of the
      amplification product

<400> SEQUENCE: 92
atatatggat ccatgtatcg tctgctgaat aaaaccgc                              38

<210> SEQ ID NO 93
<211> LENGTH: 36
<212> TYPE: DNA
<213> ORGANISM: artificial sequence
<220> FEATURE:
<223> OTHER INFORMATION: Reverse primer for amplification of the RADH
      gene; provides a SalI restriction site at the 3' end of the
      amplification product

<400> SEQUENCE: 93
atatatgtcg acttaaacct gggtcagacc accatc                                36

<210> SEQ ID NO 94
<211> LENGTH: 37
<212> TYPE: DNA
<213> ORGANISM: artificial sequence
<220> FEATURE:
<223> OTHER INFORMATION: Forward primer for amplification of the pfBAL
      gene; provides a BamHI restriction site at the 5' end of the
      amplification product

<400> SEQUENCE: 94
atatatggat ccatggcgat gattacaggc ggcgaac                               37

<210> SEQ ID NO 95
<211> LENGTH: 33
<212> TYPE: DNA
<213> ORGANISM: artificial sequence
<220> FEATURE:
<223> OTHER INFORMATION: Reverse primer for amplification of the pfBAL
      gene; provides a NotI restriction site at the 3' end of the
      amplification product

<400> SEQUENCE: 95
atatatgcgg ccgcttatgc gaagggtcc atg                                    33

<210> SEQ ID NO 96
<211> LENGTH: 36
<212> TYPE: DNA
<213> ORGANISM: artificial sequence
<220> FEATURE:
<223> OTHER INFORMATION: Forward primer for amplification of the TDot-
      Linker; provides a NdeI restriction site
```

```
<400> SEQUENCE: 96
atatatcata tgatcattaa cgaaactgcc gatgac                                  36

<210> SEQ ID NO 97
<211> LENGTH: 31
<212> TYPE: DNA
<213> ORGANISM: artificial sequence
<220> FEATURE:
<223> OTHER INFORMATION: Reverse primer for amplification of the TDot-
      Linker; provides a BamHI restriction site

<400> SEQUENCE: 97
tatataggat ccaatgctcg cgagaatggt g                                       31

<210> SEQ ID NO 98
<211> LENGTH: 40
<212> TYPE: DNA
<213> ORGANISM: artificial sequence
<220> FEATURE:
<223> OTHER INFORMATION: Forward primer for amplification of a double
      stranded DNA segment containing the ribosome binding site as well
      as a short upstream DNA sequence

<400> SEQUENCE: 98
ctagaaataa ttttgtttaa ctttaagaag gagatataca                              40

<210> SEQ ID NO 99
<211> LENGTH: 38
<212> TYPE: DNA
<213> ORGANISM: artificial sequence
<220> FEATURE:
<223> OTHER INFORMATION: Reverse primer for amplification of a double
      stranded DNA segment containing the ribosome binding site as well
      as a short upstream DNA sequence

<400> SEQUENCE: 99
tatgtatatc tccttcttaa agttaaacaa aattattt                                38
```